US005614499A

United States Patent [19]
Bylund et al.

[11] Patent Number: 5,614,499
[45] Date of Patent: Mar. 25, 1997

[54] PEPTIDE DERIVATIVES AS THROMBIN INHIBITORS

[75] Inventors: Ruth E. Bylund, Västra Frölunda; Ann-Catrine E. Teger-Nilsson, Mölndal, both of Sweden

[73] Assignee: Astra Aktiebolag, Sodertalje, Sweden

[21] Appl. No.: 984,884

[22] Filed: Dec. 2, 1992

[30] Foreign Application Priority Data

Dec. 4, 1991 [SE] Sweden .................. 9103612

[51] Int. Cl.$^6$ .................. A61K 38/05
[52] U.S. Cl. .................. 514/19; 514/18; 530/331; 548/535
[58] Field of Search .................. 514/17–19; 530/331, 530/323; 548/535

[56] References Cited

U.S. PATENT DOCUMENTS

| | | | |
|---|---|---|---|
| 4,568,636 | 2/1986 | Svendsen | 435/13 |
| 5,037,819 | 8/1991 | Han | 514/210 |
| 5,110,812 | 5/1992 | Han | 514/210 |

FOREIGN PATENT DOCUMENTS

| | | | |
|---|---|---|---|
| 0074787 | 3/1983 | European Pat. Off. . | |
| 0192135 | 3/1986 | European Pat. Off. . | |
| 0235692 | 9/1987 | European Pat. Off. . | |
| 0293881 | 12/1988 | European Pat. Off. | C07K 5/00 |
| 0468231 | 1/1992 | European Pat. Off. | C07C 279/12 |
| 2085444 | 4/1982 | United Kingdom . | |
| WO9204371 | 3/1992 | WIPO | C07K 5/08 |
| 9207869 | 5/1992 | WIPO . | |

OTHER PUBLICATIONS

Chemical Abstracts, vol. 99, No. 25, 19 Dec. 1983 (Columbus, Ohio, USA), Bajusz, Sandor et al, "Inhibition of Thrombin with H– and Boc–D–Phe–Pro–Agm," p. 21, Abstract No. 205609.

*Primary Examiner*—David Lukton
*Attorney, Agent, or Firm*—Nixon & Vanderhye

[57] ABSTRACT

The invention relates to new competitive inhibitors of thrombin, pharmaceutical compositions containing the compounds as active ingredients, and the use of the compounds as anticoagulants for prophylaxis and treatment of thromboembolic diseases, according to the formula Formula 1 wherein A represents a methylene group, an ethylene group or a propylene group, which may be substituted or A represents —$CH_2$—O—$CH_2$—, —$CH_2$—S—$CH_2$—, —$CH_2$—SO—$CH_2$—, or A represents —$CH_2$—O—, —$CH_2$—S—, —$CH_2$—SO—, with the heteroatom functionality in position 4;

n is an integer 2 to 6; and

B represents —N($R^6$)—C(NH)—$NH_2$, wherein $R^6$ is H or a methyl group, or

B represents —S—C(NH)—$NH_2$, or —C(NH)—$NH_2$.

30 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i v ) ANTI-SENSE: NO ( v ) FRAGMENT TYPE: N-terminal ( x i ) SEQUENCE DESCRIPTION: SEQ ID NO:1:

```
Ala  Asp  Ser  Gly  Glu  Gly  Asp  Phe  Leu  Ala  Glu  Gly  Gly  Gly  Val  Arg
1              5                        10                       15
Gly  Pro  Arg  Val
               20
```

PEPTIDE DERIVATIVES AS THROMBIN INHIBITORS

DESCRIPTION

This invention relates to new competitive inhibitors of thrombin, their synthesis, pharmaceutical compositions containing the compounds as active ingredients, and the use of the compounds as anticoagulants for prophylaxis and treatment of thromboembolic diseases such as venous thrombosis, pulmonary embolism, arterial thrombosis, in particular myocardial infarction and cerebral thrombosis, general hypercoagulable states and local hypercoagulable states, e.g. following angioplasty and coronary bypass operations.

The invention also relates to novel use of a compound as a starting material in synthesis of a serine protease inhibitor. Furthermore the invention relates to a novel structural fragment in a serine protease inhibitor.

BACKGROUND

Blood coagulation is the key process involved in both haemostasis (i.e. prevention of blood loss from a damaged vessel) and thrombosis (i.e. the pathological occlusion of a blood vessel by a blood clot). Coagulation is the result of a complex series of enzymatic reactions, where one of the final steps is conversion of the proenzyme prothrombin to the active enzyme thrombin.

Thrombin plays a central role in coagulation. It activates platelets, it converts fibrinogen into fibrin monomers, which polymerise spontaneously into filaments, and it activates factor XIII, which in turn crosslinks the polymer to insoluble fibrin. Thrombin further activates factor V and factor VIII in a positive feedback reaction. Inhibitors of thrombin are therefore expected to be effective anticoagulants by inhibition of platelets, fibrin formation and fibrin stabilization. By inhibiting the positive feedback mechanism they are expected to excert inhibition early in the chain of events leading to coagulation and thrombosis.

PRIOR ART

Inhibitors of thrombin based on the amino acid sequence around the cleavage site for the fibrinogen Aα chain were first reported by Blomback et al in J. Clin. Lab. Invest. 24., suppl 107, 59, (1969), who suggested the sequence Phe—Val—Arg (P9—P2—P1, herein referred to as the P3—P2—P1 sequence) to be the best inhibitor.

In U.S. Pat. No. 4,346,078 (Richter Gedeon Vegyeszeti Gyar R T, priority date Oct. 7, 1980) and in Peptides 1983 by Walter de Gruyter & Co, Berlin, pp 643–647, S. Bajusz et al described the thrombin inhibitor H—DPhe—Pro—Agm, a dipeptidyl derivative with an aminoalkyl guanidine in the P1-position.

S. Bajusz et. al. also reported in J. Med. Chem. 1990, 33, 1729–1735 and in EP-A2-0,185,390 (Richter Gedeon Vegyeszeti Gyar R T) (priority date Dec. 21, 1984) that replacing the agmatine with an arginine aldehyde gave a thrombin inhibitor which had much higher potency.

The reason for the increased activity of this thrombin inhibitor is thought possibly to be due to interaction of the aldehyde function with the Ser—OH in the active site of the enzyme forming a hemiacetal. It is not concievable to have the same type of interaction in the dipetide derivative H—DPhe—Pro—Agm since it does not have an amino acid derivative with a carbonyl group in the P1-position.

In other work in the thrombin inhibitor field, inhibitors of serine proteases that are based on electrophilic ketones instead of aldehydes in the P1-position include the following:

E. N. Shaw et al. (Research Corporation) U.S. Pat. No. 4,318,904 (priority date Apr. 25, 1980) describing peptide chloro-methyl ketones e.g. H—DPhe—Pro—Arg—CH$_2$Cl.

M. Szelke and D. M. Jones in EP-A1-0,118,280, (priority date Mar. 4, 1983) describing compounds derived from the P$_3$'—P$_2$' pentapeptide sequence of the fibrinogen Aα chain in which the scissile P$_1$'—P$_1$' peptide bond was replaced with the —CO—CH$_2$-moiety, forming a keto isostere to the corresponding peptides.

M. Kolb et. al. (Merrell-Dow) EP-A2-0,195,212 (Priority date Feb. 4, 1985) describing peptidyl α-keto esters and amides.

B. Imperiali and R. H. Abeles, Biochemistry 1986. 25. 3760 describing peptidyl fluoroalkyl ketones.

D. Schirlin et al. (Merrell-Dow) EP-A1-0,362,002 (priority date Sep. 1, 1988) describing fluoroalkylamide ketones.

P. Bey et al., (Merrell-Dow) EP-A2-0,364,344 (priority date Sep. 1, 1988 ) describing α, β, δ-triketo compounds.

Ueda et al., Biochem. J. 1990, 265, 539 also describing peptidyl fluoroalkyl ketones.

Inhibitors of thrombin based on C-terminal boronic acid derivatives of arginine and isothiouronium analogues thereof have been reported by A. D Kettner et al. (Du Pont) EP-A2-0,293,881 (priority dates Jun. 5, 1987 and Apr. 6, 1988).

An object of the present invention is to provide novel and potent thrombin inhibitors with competitive inhibitory activity towards their enzyme i.e. causing reversible inhibition. A further object is to obtain inhibitors which are orally bio-available and selective in inhibiting thrombin over other serine proteases. Stability, duration of action, and low toxicity at therapeutic dosages are still further objects of the invention.

DISCLOSURE OF THE INVENTION

Compounds

Compounds of the invention relate to the peptide sequence of human fibrinogen Aα chain representing modified sub-sites P$_9$, P$_2$ and P$_1$:

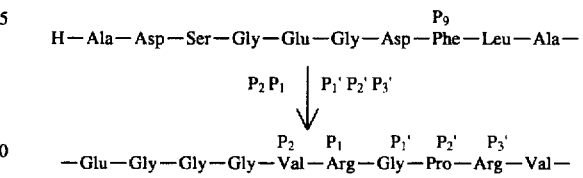

The above compound is identified as SEQ ID NO:1 in the Sequence Listing. According to the invention it has been found that compounds of the general Formula I, either as such or in the form of physiologically acceptable salts, and including stereoisomers, are potent inhibitors of thrombin:

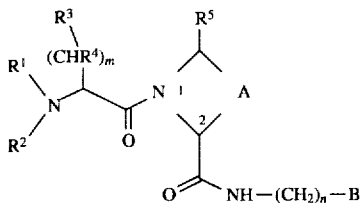

Formula I wherein:

A represents a methylene group, or

A represents an ethylene group and the resulting 5-membered ring may or may not carry one or two fluorine atoms, a hydroxy group or an oxo group in position 4, or may or may not be unsaturated, or A represents $-CH_2-O-$, $-CH_2-S-$, $-CH_2-SO-$, with the heteroatom functionality in position 4, or A represents a n-propylene group and the resulting 6-membered ring may or may not carry in position 5 one fluorine atom, a hydroxy group or an oxo group, carry two fluorine atoms in one of positions 4 or 5 or be unsaturated in position 4 and 5, or carry in position 4 an alkyl group with 1 to 4 carbon atoms, or A represents $-CH_2-O-CH_2-$, $-CH_2-S-CH_2-$, $-CH_2-SO-CH_2-$;

$R^1$ represents H, an alkyl group having 1 to 4 carbon atoms, a hydroxyalkyl group having 2-3 carbon atoms or $R^{11}OOC$—alkyl—, where the alkyl group has 1 to 4 carbon atoms and $R^{11}$ is H or an alkyl group having 1 to 4 carbon atoms or an alkylene group having 2-3 carbon atoms intramolecularly bound alpha to the carbonyl group in $R^1$, or $R^1$ represents $R^{12}OOC$-1,4-phenyl—$CH_2$—, where $R^{12}$ is H or an alkyl group having 1 to 4 carbon atoms, or $R^1$ represents $R^{13}$—NH—CO—alkyl—, where the alkyl group has 1 to 4 carbon atoms and is possibly substituted alpha to the carbonyl with an alkyl group having 1 to 4 carbon atoms and where $R^{13}$ is H or an alkyl group having 1 to 4 carbon atoms or $-CH_2COOR^{12}$ where $R^{12}$ is as defined above, or $R^1$ represents $R^{12}OOC-CH_2-OOC$—alkyl—, where the alkyl group has 1 to 4 carbon atoms and is possibly substituted alpha to the carbonyl with an alkyl group having 1 to 4 carbon atoms and where $R^{12}$ is as defined above, or $R^1$ represents $CH_3SO_2-$, or $R^1$ represents $R^{12}OCOCO-$ where $R^{12}$ is as defined above, or $R^1$ represents $-CH_2PO(OR^{14})_2$, $-CH_2SO_3H$ or $-CH_2-(5-(1H)-tetrazolyl)$ where $R^{14}$ is, individually at each occurrence, H, methyl or ethyl;

$R^2$ represents H or an alkyl group having 1 to 4 carbon atoms or $R^{21}OOC$—alkyl—, where the alkyl group has 1 to 4 carbon atoms and is possibly substituted in the position which is alpha to the carbonyl group, and the alpha substituent is a group $R^{22}-(CH_2)_p-$, wherein p=0–2 and $R^{22}$ is methyl, phenyl, OH, $COOR^{21}$, and $R^{21}$ is H or an alkyl group having 1 to 4 carbon atoms;

m is 0, 1 or 2, $R^3$ represents a cyclohexyl group and $R^4$ represents H, or m is 1 and $R^3$ represents a cyclohexyl or phenyl group and $R^4$ forms an ethylene bridge together with $R^1$, or m is 1 and $R^3$ and $R^4$ each represents a cyclohexyl or phenyl group;

$R^5$ represents H or an alkyl group having 1 to 4 carbon atoms;

n is an integer 2 to 6; and

B represents $-N(R^6)-C(NH)-NH_2$, wherein $R^6$ is H or a methyl group, or

B represents $-S-C(NH)-NH_2$, or $-C(NH)-NH_2$.

An alkyl group may be straight or branched unless specified otherwise. Alkyl groups having 1 to 4 carbon atoms are methyl, ethyl, n-propyl, i-propyl, n-butyl, i-butyl, s-butyl and t-butyl. When unsaturation is referred to, a carbon—carbon double bond is intended. Abbreviations are listed at the end of this specification.

According to a preferred embodiment the invention relates to compounds of Formula I, wherein $R^1$ represents $R^{11}OOC$—alkyl—, where the alkyl group has 1 to 4 carbon atoms and $R^{11}$ is H. Of those compounds, the compounds where A is ethylene and $R^5$ is H or an alkyl group having 1 to 4 carbon atoms, particularly those where $R^5$ is H are preferred.

Of the compound of Formula I, those compounds where $R^3$ is cyclohexyl, m is 1 or 2, particularly m is 1 and $R^4$ is H constitute another preferred subclass.

Another preferred group of compounds are the compounds where A is n-propylene and the resulting 6-membered ring may or may not carry in position 4 an alkyl group with 1 to 4 carbon atoms, and $R^5$ is H or an alkyl group having 1 to 4 carbon atoms, particularly those where $R^5$ is H.

According to another preferred embodiment n is 3.

Compounds of Formula I having S-konfiguration on the α-amino acid in the P2-position are preferred ones, of those compounds also having R-konfiguration on the α-amino acid in the P3-position are particularly preferred ones.

Preferred compounds of the invention are:

| Example No. | Compound |
| --- | --- |
| 1 | H—(R)Cha—Pro—Agm |
| 2 | Me—(R)Cha—Pro—Agm |
| 3 | HO—(CH$_2$)$_3$—(R)Cha—Pro—Agm |
| 4 | HOOC—CH$_2$—(R)Cha—Pro—Agm |
| 5 | $^i$PrOOC—CH$_2$—(R)Cha—Pro—Agm |
| 6 | HOOC—CH$_2$—(Me)(R)Cha—Pro—Agm |
| 7 | HOOC—(R,S)CH(Me)—(R)Cha—Pro—Agm |
| 8 | HOOC—(RorS)CH(Me)—(R)Cha—Pro—Agm/a |
| 9 | HOOC—(RorS)CH(Me)—(R)Cha—Pro—Agm/b |
| 10 | HOOC—(RorS)CH($^n$Pr)—(R)Cha—Pro—Agm/a |
| 11 | HOOC—(RorS)CH($^n$Pr)—(R)Cha—Pro—Agm/b |
| 12 | HOOC—(RorS)CH(Ph)—(R)Cha—Pro—Agm/b |
| 13 | HOOC—(R,S)CH(CH$_2$CH$_2$Ph)—(R)Cha—Pro—Agm |
| 14 | HOOC—(RorS)CH(CH$_2$CH$_2$Ph)—(R)Cha—Pro—Agm/a |
| 15 | HOOC—CH$_2$—CH$_2$—(R)Cha—Pro—Agm |
| 16 | EtOOC—CO—(R)Cha—Pro—Agm |
| 17 | (R,S)Bla—(R)Cha—Pro—Agm |

-continued

| Example No. | Compound |
|---|---|
| 18 | HOOC—(RorS)CH(CH₂CH₂Ph)—(R)Cha—Pro—Agm/b |
| 19 | H—(R)Cha—Pro—Nag |
| 20 | ⁿBu—(R)Cha—Pro—Nag |
| 21 | HO—(CH₂)₃—(R)Cha—Pro—Nag |
| 22 | HOOC—CH₂—(R)Cha—Pro—Nag |
| 23 | EtOOC—CH₂—(R)Cha—Pro—Nag |
| 24 | ⁱPrOOC—CH₂—(R)Cha—Pro—Nag |
| 25 | ⁱBuOOC—CH₂—(R)Cha—Pro—Nag |
| 26 | HOOC—CH₂—OOC—CH₂—(R)Cha—Pro—Nag |
| 27 | H₂N—CO—CH₂—(R)Cha—Pro—Nag |
| 28 | HOOC—CH₂—NH—CO—CH₂—(R)Cha—Pro—Nag |
| 29 | (HOOC—CH₂)₂—(R)Cha—Pro—Nag |
| 30 | HOOC—CH₂—(Me)(R)Cha—Pro—Nag |
| 31 | HOOC—CH₂—(nBu)(R)Cha—Pro—Nag |
| 32 | HOOC—(R,S)CH(Me)—(R)Cha—Pro—Nag |
| 33 | HOOC—(RorS)CH(Me)—(R)Cha—Pro—Nag/a |
| 34 | HOOC—(RorS)CH(Me)—(R)Cha—Pro—Nag/b |
| 35 | EtOOC—(R,S)CH(Me)—(R)Cha—Pro—Nag |
| 36 | HOOC—(RorS)CH(ⁿPr)—(R)Cha—Pro—Nag/a |
| 37 | HOOC—(R)CH(CH₂—OH)—(R)Cha—Pro—Nag |
| 38 | HOOC—(R,S)CH(Ph)—(R)Cha—Pro—Nag |
| 39 | HOOC—(S)CH(CH₂CH₂Ph)—(R)Cha—Pro—Nag |
| 40 | HOOC—(R)CH(CH₂CH₂Ph)—(R)Cha—Pro—Nag |
| 41 | HOOC—CH₂—CH₂—(R)Cha—Pro—Nag |
| 42 | EtOOC—CH₂—CH₂—(R)Cha—Pro—Nag |
| 43 | HOOC—(CH₂)₃—(R)Cha—Pro—Nag |
| 44 | EtOOC—(CH₂)₃—(R)Cha—Pro—Nag |
| 45 | HOOC—CO—(R)Cha—Pro—Nag |
| 46 | MeOOC—CO—(R)Cha—Pro—Nag |
| 47 | (R,S)Bla—(R)Cha—Pro—Nag |
| 48 | HOOC—(R,S)CH(CH₂COOH)—(R)Cha—Pro—Nag |
| 49 | MeOOC—(R,S)CH(CH₂COOMe)—(R)Cha—Pro—Nag |
| 50 | HOOC—Ph-4-CH₂—(R)Cha—Pro—Nag |
| 51 | (HO)₂P(O)—CH₂—(R)Cha—Pro—Nag |
| 52 | EtO(HO)P(O)—CH₂—(R)Cha—Pro—Nag |
| 53 | (EtO)₂P(O)—CH₂—(R)Cha—Pro—Nag |
| 54 | HOOC—CH₂—(R)Cha—Pro—Mag |
| 55 | H—(R,S)Pro(3-Ph)—Pro—Agm |
| 56 | H—(R,S)Pro(3-(trans)Ch)—Pro—Agm |
| 57 | HOOC—CH₂—(R,S)Pro(3-(trans)Ph)—Pro—Agm |
| 58 | HOOC—CH₂—(R,S)Pro(3-(trans)Ph)—Pro—Nag |
| 59 | HOOC—CH₂—(R)Cha—Pic—Agm |
| 60 | HOOC—CH₂—(Me)(R)Cha—(R,S)Pic—Agm |
| 61 | HOOC—(R,S)CH(Me)—(R)Cha—Pic—Agm |
| 62 | HOOC—(RorS)CH(Me)—(R)Cha—Pic—Agm/a |
| 63 | HOOC—(RorS)CH(Me)—(R)Cha—Pic—Agm/b |
| 64 | HOOC—CH₂—CH₂—(R)Cha—Pic—Agm |
| 65 | H—(R)Cha—Pic—Nag |
| 66 | Me—(R)Cha—(R,S)Pic—Nag |
| 67 | HOOC—CH₂—(R)Cha—Pic—Nag |
| 68 | MeOOC—CH₂—(R)Cha—Pic—Nag |
| 69 | ⁱPrOOC—CH₂—(R)Cha—Pic—Nag |
| 70 | HOOC—CH₂—(Me)(R)Cha—(RorS)Pic—Nag/b |
| 71 | HOOC—(R,S)CH(Me)—(R)Cha—(R,S)Pic—Nag |
| 72 | HOOC—(RorS)CH(Me)—(R)Cha—(RorS)Pic—Nag/c |
| 73 | HOOC—(RorS)CH(Me)—(R)Cha—(RorS)Pic—Nag/d |
| 74 | HOOC—CH₂—CH₂—(R)Cha—Pic—Nag |
| 75 | HOOC—CH₂—(R)Cha—(R,S)Mor—Agm |
| 76 | HOOC—CH₂—(R)Cha—(RorS)Mor—Nag |
| 77 | H—(R)Cha—Aze—Nag |
| 78 | HOOC—CH₂—(R)Cha—Aze—Nag |
| 79 | H—(R)Cha—Pro(5-(S)Me)—Nag |
| 80 | HOOC—CH₂(R)Cha—Pro(5-(S)Me)—Nag |
| 81 | HOOC—CH₂—(R)Cha—(RorS)Pic(4,5-dehydro)—Nag/b |
| 82 | HOOC—CH₂—(R)Cha—Pic(4-(S)Me)—Nag |
| 83 | HOOC—CH₂—(R)Cha—(R)Pic(4-(R)Me)—Nag |
| 84 | HOOC—CH₂—(R)Cgl—Pic—Nag |
| 85 | H—(R)Hoc—Pro—Nag |
| 86 | HOOC—CH₂—(R)Hoc—Pro—Nag |
| 87 | HOOC—CH₂—(R)Hoc—Pic—Nag |
| 88 | HOOC—CH₂—(R)Dph—Pic—Nag |
| 89 | HOOC—CH₂—(R)Dch—Pic—Nag |
| 90 | HOOC—CH₂—(R)Cha—Pro(5-(R,S)Me)—Nag |
| 91 | H—(R)Cha—Pic(4-(R)Me)—Nag |
| 92 | HOOC—CH₂—(R)Cha—Pic(4-(R)Me)—Nag |
| 93 | HOOC—CH₂—(R)Cha—Pic(6-(S)Me)—Nag |

Of those compounds, the compounds having Example Nos. 4, 6, 9, 22, 30, 34, 59, 63, 67, 73, 80 and 82 are particularly preferred, and of those the following compounds are most preferred:

| | |
|---|---|
| 30 | HOOC—CH$_2$—(Me)(R)Cha—Pro—Nag |
| 34 | HOOC—(RorS)CH(Me)—(R)Cha—Pro—Nag/b |
| 67 | HOOC—CH$_2$—(R)Cha—Pic—Nag |

The most preferred compound among compounds of Formula I is HOOC—CH$_2$(R)Cha—Pic—Nag.

In the above tables of compounds, the letters /a, /b, /c and /d refer to a substantially pure stereoisomer at the carbon atom denoted "RorS". The stereoisomer can be identified for each compound with reference to the experimental part herein. "R,S" refers to a mixture of stereoisomers.

In a further embodiment the invention relates to novel use of a compound of the formula:

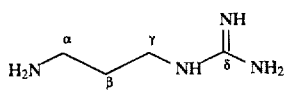

as a starting material in synthesis of a serine protease inhibitor, and in particular in synthesis of a thrombin inhibitor. It can be used as such or having the guanidino group either mono protected at the δ-nitrogen or diprotected at the δ-nitrogens or the γ, δ-nitrogens, preferably with a protective group such as benzyloxy carbonyl. Protection of the noragmatine derivatives is carried out by methods known in the art for guanidino compounds. This compound is named "noragmatine" or "Nag" herein. The compound has been previously disclosed inter alia as a hair bleaching accelerator in GB 1,599,324 (Henkel, priority date Feb. 5, 1977). The structural fragment of the formula

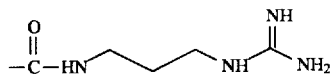

has however not been previously disclosed as a structural element in a pharmaceutically active compound. As such structural element the "noragmatine" fragment renders a serine protease inhibitor, and in particular a thrombin inhibitor valuable.

Medical and Pharmaceutical Use

In a further embodiment the invention relates to treatment, in a human or animal organism, of conditions where inhibition of thrombin is required. The compounds of the invention are expected to be useful in particular in animals including man in treatment or prophylaxis of thrombosis and hypercoagulability in blood and tissues. It is furthermore expected to be useful in situations where there is an undesirable excess of the thrombin without signes of hypercoagulability. Disease states in which the compounds have a potential utility, in treatment and/or prophylaxis, include venous thrombosis and pulmonary embolism, arterial thrombosis, such as in myocardial infarction, unstable angina, thrombosis-based stroke and peripheral arterial thrombosis. Further, the compounds have expected utility in prophylaxis of atherosclerotic diseases such as coronary arterial disease, cerebral arterial disease and peripheral arterial disease. Further, the compounds are expected to be useful together with thrombolytics in thrombotic diseases, in particular myocardial infarction. Further, the compounds have expected utility in prophylaxis for re-occlusion after thrombolysis, percutaneous trans-luminal angioplasty (PTCA) and coronary bypass operations. Further, the compounds have expected utility in prevention of re-thrombosis after microsurgery. Further, the compounds are expected to be useful in anticoagulant treatment in connection with artificial organs and cardiac valves. Further, the compounds have expected utility in anticoagulant treatment in haemodialysis and disseminated intravascular coagulation.

A further expected utility is in rinsing of catheters and mechanical devises used in patients in vivo, and as an anticoagulant for preservation of blood, plasma and other blood products in vitro.

Pharmaceutical Preparations

The compounds of the Formula I will normally be administered by the oral, rectal, dermal, nasal or parenteral route in the form of pharmaceutical preparations comprising the active ingredient either as a free base or a pharmaceutical acceptable non-toxic acid addition salt, e.g. the hydrochloride, hydrobromide, lactate, acetate, citrate, p-toluenesulfonate, trifluoroacetate and the like in a pharmaceutically acceptable dosage form.

The dosage form may be a solid, semisolid or liquid preparation prepared by per se known techniques. Usually the active substance will constitute between 0.1 and 99% by weight of the preparation, more specifically between 0.1 and 50% by weight for preparations intended for parenteral administration and between 0.2 and 75% by weight for preparations suitable for oral administration.

Suitable daily doses of the compounds of the invention in therapeutical treatment of humans are about 0.001–100 mg/kg body weight at peroral administration and 0.001–50 mg/kg body weight at parenteral administration.

Preparation

A further objective of the invention is the mode of preparation of the compounds. The compounds of Formula I may be prepared by coupling of an N-terminally protected amino acid or dipeptide or a preformed, N-terminally alkylated protected dipeptide to a compound

wherein n is as defined with Formula I and X is an unprotected or protected guanidino group or a protected amino group, or a group transferable into an amino group, where the amino group is subsequently transferred into a guanidino group.

The coupling is accordingly done by one of the following methods:

METHOD I

Coupling of an N-terminally protected dipeptide, prepared by standard peptide coupling, with either a protected- or unprotected amino guanidine or a straight chain alkylamine carrying a protected or masked amino group at the terminal end of the alkyl chain, using standard peptide coupling, shown in the formula

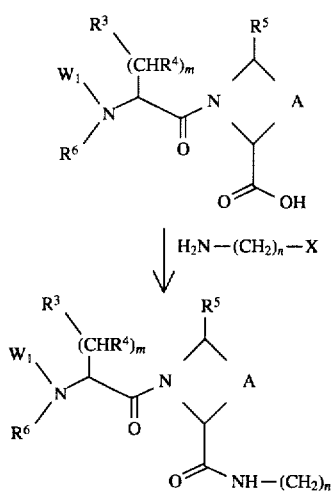

wherein $R^3$, $R^4$, $R^5$, n, m and A are as defined in Formula I, $R^6$ is H or alkyl, $W_1$ is an amino protecting group such as tertiarybutoxy carbonyl and benzyloxy carbonyl and X is —NH—C(NH)NH$_2$, —NH—C(NH)NH—W$_2$, —N(W$_2$)—C(NH)NH—W$_2$, —NH—C(NW$_2$)NH—W$_2$ or —NH—W$_2$, where W$_2$ is an amine protecting group such as tertiarybutoxy carbonyl or benzyloxy carbonyl, or X is a masked amino group such as azide, giving the protected peptide. The final compounds can be made in any of the following ways, depending on the nature of the X- group used: Removal of the protecting group(s) (when X=—NH—C(NH)NH$_2$, —N(W$_2$)—C(NH)NH—W$_2$, —NH—C(NW$_2$)NH—W$_2$ or —NH—C(NH)NH—W$_2$), or a selective deprotection of the $W_1$- group (e.g when X=—NH—C(NH)NH—W$_2$, —N(W$_2$)—C(NH)NH—W$_2$, —NH—C(NW$_2$)NH—W$_2$, W$_2$ in this case must be orthogonal to $W_1$) followed by alkylation of the N-terminal nitrogen and deprotection or a selective deprotection/unmasking of the terminal alkylamino function (X=NH—W$_2$, W$_2$ in this case must be orthogonal to $W_1$ or X=a masked aminogroup, such as azide) followed by a guanidation reaction, using standard methods, of the free amine and deprotection of the $W_1$-group.

METHOD II

Coupling of an N-terminally protected amino acid, prepared by standard methods, with either a protected- or unprotected amino guanidine or a straight chain alkylamine carrying a protected or masked amino group at the terminal end of the alkyl chain, using standard peptide coupling, shown in the formula

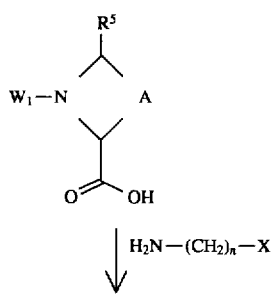

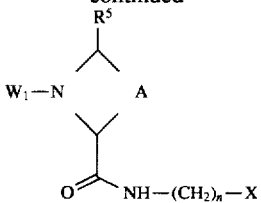

wherein $W_1$, A, $R^5$ and X are as defined above followed by deprotection of the $W_1$-group and coupling with the N-terminal amino acid, in a protected form, leading to the protected peptide described in Method I or III, depending on the choice of the substitution pattern on the nitrogen of the N-terminal amino acid used in the coupling. The synthesis is then continued according to Method I or Method III to give the final peptides.

METHOD III

Coupling of a preformed N-terminally alkylated and protected dipeptide, prepared by standard peptide coupling, with either a protected or unprotected amino guanidine or a straight chain alkylamine carrying a protected or masked aminogroup at the terminal end of the alkyl chain, using standard peptide coupling, shown in the formula

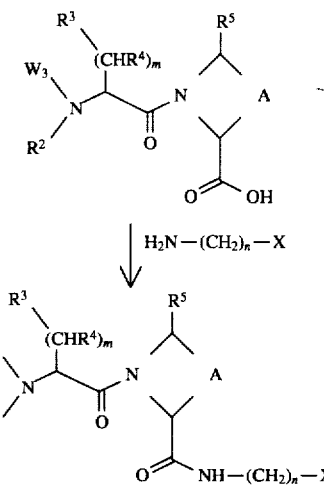

wherein $R^2$, $R^3$, $R^4$, $R^5$, n, m, A and X are defined as above provided that $R^2$ is other than H and $W_3$ is an acyl protecting group such as trifluoroacyl.

The final compounds can be made in any of the following ways depending on the nature of the X-group used: Removal of protecting groups (when X=NH—C(NH)NH$_2$, NH—C(NH)NH—W$_2$, N(W$_2$)—C(NH)NH—W$_2$, NH—C(NW$_2$)NH—W$_2$ or NH—W$_2$) or a selective deprotection/unmasking of the terminal alkylamino function (X=NH—W$_2$, W$_2$ in this case must be orthogonal to W$_3$ or X=a masked amino group such as azide) followed by a guanidation deprotection of the W$_3$ group.

DETAILED DESCRIPTION OF THE INVENTION

The following description is illustrative of aspects of the invention.

EXPERIMENTAL PART

Synthesis of the compounds of the invention is illustrated in Schemes I to VI appended hereto.

General Experimental Procedures

The $^1H$ NMR and $^{13}C$ NMR measurements were performed on BRUKER AC-P 300 and BRUKER AM 500 spectrometers, the former operating at a $^1H$ frequency of 500.14 MHz and a $^{13}C$ freguency of 125.76 MHz and the latter at $^1H$ and $^{13}C$ freguency of 300.13 MHz and 75.46 MHz respectively.

The samples were 10–50 mg dissolved in 0.6 ml of either of the following solvents; $CDCl_3$ (isotopic purity>99.8%, Dr. Glaser AG Basel), $CD_3OD$ (isotopic purity>99.95%, Dr. Glaser AG Basel) or $D_2O$ (isotopic purity>99.98%, Dr. Glaser AG Basel).

The $^1H$ and $^{13}C$ chemical shift values in $CDCl_3$ and $CD_3OD$ are relative to tetramethylsilane as an external standard. The $^1H$ chemical shifts in $D_2O$ are relative to the sodium salt of 3-(trimethylsilyl)-$d_4$-propanoic acid and the $^{13}C$ chemical shifts in $D_2O$ are referenced relative to 1,4-dioxane (67.3 ppm), both as external standard. Calibrating with an external standard may in some cases cause minor shift differences compared to an internal standard, however, the difference in $^1H$ chemical shift is less than 0.02 ppm and in $^{13}C$ less than 0.1 ppm.

The $^1H$ NMR spectrum of peptide sequences containing a proline residue frequently exhibits two sets of resonances. This corresponds to the existence of to contributing conformers with respect to the rotation around the amide bond, where proline is the N-part of the amide bond. The conformers are named cis and trans. In our compounds the sequences (R)Cha—Pro— and —(R)Cha—Pic— often give rise to a cis-trans equilibrium with one conformer as the preponderant conformer (>90%). In those cases only the $^1H$ chemical shifts of the major rotamer is reported.

Thin-Layer Chromatography was carried out on commercial Merck Silicagel $60F_{254}$ coated glass or aluminium plates. Visualization was by a combination of UV-light, followed by spraying with a solution prepared by mixing 372 ml of EtOH(95%), 13.8 ml of concentrated $H_2SO_4$, 4.2 ml of concentrated acetic acid and 10.2 ml of p-methoxy benzaldehyde or phosphomolybdic acid reagent (5–10 w.t % in EtOH(95%)) and heating.

Flash chromatography was carried out on Merck Silicagel 60 (40–63 mm, 230–400 mesh) under pressure of $N_2$.

Reversed phase high-performance liquid chromatography (in the Examples referred to as RPLC) was performed on a Waters M-590 instrument equipped with three reverse phase Kromasil 100,C8 columns (Eka-Nobel) having different dimensions for analytical (4.6 mm×250 mm), semipreparative (1"×250 mm) and preparative (2"×500 mm) chromatography detecting at 226 nm.

Freeze-drying was done on a Leybold-Heraeus, model Lyovac GT 2, apparatus.

Protection Procedures

Boc—(R)Cha—OH

To a solution of H—(R)Cha—OH, 21.55 g (125.8 mmol), in 130 ml 1M NaOH and 65 ml THF was added 30 g (137.5 mmol) of $(Boc)_2O$ and the mixture was stirred for 4.5 h at room temperature. The THF was evaporated and an additional 150 ml of water was added. The alkaline aqueous phase was washed twice with EtOAc, then acidified with 2M $KHSO_4$ and extracted with 3×150 ml of EtOAc. The combined organic phase was washed with water, brine and dried $(Na_2SO_4)$. Evaporation of the solvent afforded 30.9 g (90.5%) of the title compound as a white solid.

Z—(R)Cha—OH

The same procedure as described in Bodanszky M. and Bodanszky A. "The Practice of Peptide Synthesis", Springer-Verlag, 1984, p. 12, was used starting from H—(R)Cha—OH.

Boc—(Me)Phe—OH

Prepared in the same way as Boc—(R)Cha—OH from Me—(R)Phe—OH.

Boc—(R,S)Pro(3-(trans)Ph)—OH

To a well stirred solution of 2.0 g (8.8 mmol, 1 eq.) H—(R,S)Pro(3-(trans)Ph)—OH×HCl (Prepared as described in J. Org. Chem., 55, p. 270–75, 1990 and J. Org. Chem., 39, 1710–1716, 1974), in 17.6 ml of 1N NaOH, 12 ml of $H_2O$ and 12 ml of THF at +5° C. was added 2.33 g $(Boc)_2O$ (10.7 mmol, 1.2 eq.). The reaction was allowed to reach room temperature and the stirring was continued for an additional 18 h. The organic solvent was evaporated and 50 ml of $H_2O$ was added to the residue. The basic water phase was washed with 2×50 ml of EtOAc and acidified with 2M $KHSO_4$ (pH about 1). The acidic water phase was extracted with 4×75 ml of EtOAc and the combined organic phase was washed with 1×40 ml of $H_2O$, 1×40 ml of brine and dried $(MgSO_4)$. Evaporation of the solvent gave 2.0 g (78%) of pure product as a white solid.

1H-NMR ($CDCl_3$, 500 MHz, mixture of two rotamers): δ 1.4 and 1.5 (2s, 9H), 2.0–2.1 (m, 1H), 2.3–2.4 (m, 1H), 3.45–3.88 (m, 3H), 4.3 and 4.45 (2d, 1H), 7.2–7.4 (m, 5H).

Boc—(R,S)Pro(3-Ph)—OH

Prepared as above starting from a cis/trans mixture of H—(R,S)Pro(3-Ph)—OH.

Boc—(R)Dph—OH

Prepared according to the method described by K. Hsich et.al. in J. Med. Chem., 32, p. 898 (1989) from H—(R)Dph—OH.

Boc—(R)Hop—OH

Prepared by the same procedure as described for Boc—(R)Cha—OH starting from H—(R)Hop—OH.

$^1$H-NMR (300 MHz, $CDCl_3$): δ 1.45 (s, 9H), 2.00 (m, 1H), 2.22 (m, 1H), 2.75 (bt, 2H), 4.36 (bs, 1H), 5.05 (bs, 1H), 7.15–7.33 (m, 5H).

Deprotection Procedures (a) The protected peptide was dissolved in EtOH (95%) and hydrogenated over 5% Pd/C at atmospheric pressure in the presence of an excess of TFA or HOAc (>2 eq.) for about 1–4 h. The catalyst was filtered off, the solvent evaporated and the final peptide (TFA or HOAc salt) was isolated as a white powder after freeze drying ($H_2O$).

(b) The same as in (a) except that EtOH/$H_2O$ (ca:5/1) was used as solvent.

(c) The same procedure as in (a) but MeOH was used as solvent.

(d) The same as in (a) but 2M HCl was used as acid to give the HCl-salt.

(e) Hydrolysis of esters, an illustrative example:

EtOOC—$CH_2$—(R)Cha—Pro—Nag×2 HOAc (0.4 mmol) was dissolved in 1.5 ml of MeOH and 1.2 ml (1.2 mmol) of 1M NaOH was added at room temperature. After 3 h the methanol was evaporated and an excess HOAc was added to the residue and the mixture was freeze dried and purified by RPLC ($CH_3CN$/0.1M $NH_4OAc$ (70/30)). The pure product was obtained as a powder in 73% yield after freeze drying from water.

(f) Cleavage of t-butyl esters, an illustrative example:

The t-butyl ester was dissolved in an excess of TFA. After stirring for 2 h at room temperature the TFA was evaporated. Purification by treatment with activated charcoal in water-ethanol was followed by freeze drying from water giving the desired compounds.

Preparation of Starting Materials

H—Pic—OEt×HCl

L-Pipecolinic acid, 4.0 g (0.031 mol), was slurried in 100 ml of abs. ethanol and HCl (g) was briefly bubbled through until a clear solution was obtained. It was cooled in an ice bath and 17 ml of thionyl chloride was added dropwise over 15 min.

The ice bath was removed and the mixture was refluxed for 2.5 h. The solvent was evaporated and the product was obtained as its hydrochloride salt in a quantitative yield.

$^1$H-NMR (300 MHz, D$_2$O): δ 1.33 (t, 3H), 1.8–2.1 (m, 5H), 2.3–2.5 (m, 1H), 3.1–3.3 (m, 1H), 3.5–3.7 (m, 1H), 4.14 (dd, 1H), 4.44 (q, 2H).

H—Pic—OMe×HCl

Prepared in the same way as described for H—Pic—OEt× HCl by replacing EtOH with MeOH.

H—Aze—OEt×HCl

Prepared in the same way as described for H—Pic—OEt× HCl from H—Aze—OH.

H—Pic(4-(S)Me)—OEt×HCl

Prepared in the same way as described for H—Pic—OEt× HCL from H—Pic(4-(S)Me)—OH (purchased from Synthelec, Lund, Sweden).

H—(R)Pic(4-(R)Me)—OEt×HCl

Prepared in the same way as described for H—Pic—OEt× HCl from H—(R)Pic(4-(R)Me)OH (purchased from Synthelec, Lund, Sweden).

H—(R)Dph—OH

Prepared by the general method given by A. Evans et. al. in JACS, 112, 4011 (1990).

H—(R,S)Pic(4,5-dehydro)—OEt H—(R,S)Pic(4,5-dehydro)—OH, 3.05 g (18.1 mmol) (Prepared according to the procedure by Burgstahler et. al. J. Org. Chem, 25, 4, p. 489–92 (1960), was dissolved in 75 ml EtOH/HCl (saturated) and the mixture was refluxed for 5 hours. The solvent was evaporated and the remining residue was dissolved in water, made alkaline with sodium hydroxide (aq) and extracted three times with ethylacetate. Drying (Na$_2$SO$_4$) and carefull evaporation gave 2,05 g (71%) of the title compound.

$^1$H-NMR (CDCl$_3$): δ 1.28 (t, 3H), 1.88 (bs, NH) 2.2–2.4 (m, 2H), 3.45 (bs, 2H), 3.57 (dd, 1H), 4.21 (q, 2H), 5.68–5.82 (m, 2H).

Boc—(R)Cgl—OH

Boc—(R)Pgl—OH was hydrogenated over 5% Rh/Al$_2$O$_3$ in MeOH at 5 Mpa. Filtration and evaporation of the solvent gave the title compound which was used without further purification.

$^1$H-NMR (300 MHz,CDCl$_3$): δ 0.9–1.7 (m, 20H), 4.0–4.2 (m, 1H), 5.2 (d, 1H).

Boc—(R)Dch—OH

Boc—(R)Dph—OH, 0.75 g (2.2 mmol), was dissolved in 25 ml of MeOH and a catalytic amount of 5% Rh/Al$_2$O$_3$ was added. The mixture was hydrogenated at 5 Mpa, 50° C. for 40 h, filtered and evaporated to give 0.72 g (93%) of the thitle compound.

$^1$H-NMR (CDCl$_3$): δ 0.9–2.0 (m, 32H), thereof 1.45 (bs, 9H), 4.55 (bd) and 4.9 (bd); two rotamers integrating for a total of 1H, 5.7–6.1 (broad, NH).

H—(R)Pro(5-(S)Me)-OMe

Prepared according to the procedure given by B. Gopalan et.al. in J. Org. Chem., 51, 2405, (1986).

H—Mor—OH

Prepared according to the method of K. Nakajima. et al. Bull. Chem. Soc. Jpn., 51 (5), 1577–78, 1978 and ibid 60, 2963–2965, 1987.

H—Mor—OEt×HCl

Prepared in the same way as H—Pic—OEt×HCl from H—Mor—OH.

Boc—(R)Cha—OSu

Boc—(R)Cha—OH (1 eq.), HOSu (1.1 eq) and DCC or CME—CDI (1.1 eq) were dissolved in acetonitrile (about 2.5 ml/mmol acid) and stirred at room temperature over night. The precipitate formed during the reaction was filtered off, the solvent evaporated and the product dried in vacuo. (When CME—CDI was used in the reaction the residue, after evaporation of the CH$_3$CN, was dissolved in EtOAc and the organic phase washed with water and dried. Evaporation of the solvent gave the title compound).

$^1$H-NMR (500 MHz, CDCl$_3$, 2 rotamers ca: 1:1 ratio) δ 0.85–1.1 (m, 2H), 1.1–1.48 (m, 4H), 1.5–1.98 (m, 16H; thereof 1.55 (bs, 9H)), 2.82 (bs, 4H), 4.72 (bs, 1H, major rotamer), 4.85 (bs, 1H, minor).

Boc—(Me)(R)Cha—OSu (i) Boc—(Me)(R)Cha—OH

A solution of 11,9 g (42.6 mmol) Boc—(Me)(R)Phe—OH in 150 ml MeOH was hydrogenated over 5% Rh/Al$_2$O$_3$ at 0,28 Mpa for 24 h. Filtration of the catalyst and evaporation of the solvent gave the product as a white solid (95% yield) wich was used in the next step without further purification.

$^1$H-NMR (500 MHz, CDCl$_3$, mixture of two rotamers ca: 1/1). δ 0.8–1.1 (m, 2H), 1.1–1.9 (m, 20H, thereof 1.47 and 1.45 (s, 9H)), 2.82 and 2.79 (s, total 3H), 4.88 and 4.67 (m, total 1H).

(ii) Boc—(Me)(R)Cha—OSu

Prepared in the same way as described for Boc—(R)Cha—OSu— from Boc—(Me)(R)Cha—OH.

Boc—(R)Cha—Pro—OSu (i) Boc—(R)Cha—Pro—OH

H—(S)Pro—OH (680 mmol) was dissolved in 0.87M sodium hydroxide (750 ml). Boc—(R)Cha—OSu (170 mmol) dissolved in DMF (375 ml) was added dropwise during 20 min. The reaction mixture was stirred at room temperature for 20 h. The mixture was acidified (2M KHSO$_4$) and extracted three times with ethyl acetate. The organic layers were combined and washed three times with water and once with brine. After drying over sodium sulphate and evaporation of the solvent, the syrupy oil was dissolved in diethyl ether, the solvent evaporated and finally the product dried in vacuo to yield Boc—(R)Cha—Pro—OH as a white powder in almost quantitative yield.

$^1$H-NMR (500 MHz, CDCl$_3$, minor rotamer 10%) δ 0.8–1.05 (m, 2H), 1.05–1-55 (m, 15H; thereof 1.5 (bs, 9H)), 1.55–1.8 (m, 5H), 1.8–2.15 (m, 3H), 2.47 (m, 1H), 3.48 (m, 1H), 3.89 (m, 1H), 4.55 (m, 2H), 5.06 (m, 1H); minor rotamer signals 2.27 (m, 1H), 3.58 (m, 1H), 4.33 (m, 1H), 5.0 (m, 1H)

(ii) Boc—(R)Cha—Pro—OSu

Prepared in the same way as described for Boc—(R)Cha—OSu— from Boc—(R)Cha—Pro—OH.

$^1$H-NMR (500 MHz, CDCl$_3$, 2 rotamers, 5:1 ratio) δ 0.78–1.05 (m, 2H), 1.05–1.83 (m, 20H; thereof 1.43 (bs, 9H)), 1.83–2.26 (m, 3H), 2.32 (m, 1H), 2.72–2.9 (m, 4H), 3.2 (m, 1H, minor rotamer), 3.52 (m, 1H, major), 3.68 (m, 1H, minor rotamer), 3.89 (m, 1H, major), 4.31 (bq, 1H, minor rotamer), 4.56 (bq, 1H, major), 4.71 (bt, 1H, major rotamer), 4.93 (bt, 1H, minor), 5.22 (bd, 1H, major rotamer), 5.44 (bd, 1H, minor).

Z—(R)Cha—Pro—OSu

Prepared in the same way as Boc—(R)Cha—Pro—OSu from Z—(R)Cha—OH.

Boc—(R)Cha—Pic—OSu (i) Boc—(R)Cha—Pic—OEt

Boc—(R)Cha—OH, 6.3 g (0.023 mol), was dissolved in 150 ml of CH$_2$Cl$_2$. The solution was cooled in an ice bath and 6.3 g (0.047 mol) of N-hydroxybenzotriazole and 11.2 g (0.0265 mol) of CME—CDI were added. The ice bath was removed after 15 min and the reaction mixture was stirred for 4 h at room temperature. The solvent was evaporated and the residue dissolved in 150 ml of DMF and cooled in an ice bath. H—Pic—OEt×HCl, 4.1 g (0.021 mol) was added and the pH adjusted to approximately 9 by addition of N-methylmorpholine. The ice bath was removed after 15 min and the reaction mixture was stirred for 3 days. The solvent was evaporated and the residue was dissolved in ethyl acetate and washed with dilute KHSO$_4$ (aq), NaHCO$_3$ (aq) and water. The organic layer was dried (Na$_2$SO$_4$) and evaporated to give 7.7 g (89%) of Boc—(R)Cha—Pic—OEt which was used without further purification.

$^1$H-NMR (500 MHz, CDCl$_3$, 2 rotamers, 3:1 ratio ) δ 0.7–1.0 (m, 2H), 1.1–1.9 (m, 29H; thereof 1.28 (t, 3H)), 1.45 (bs, 9H), 2.01 (bd, 1H, major rotamer), 2.31 (bd, 1H), 2.88 (bt, 1H, minor), 3.30 (bt, 1H, major), 3.80 (bd, 1H, major), 4.15–4.3 (m, 2H), 4.5–4.7 (m, 2H, minor), 4.77 (bq, 1H, major), 4.90 (bd, 1H, minor), 5.28 (bd, 1H, major), 5.33 (bd, 1H, major).

(ii) Boc—(R)Cha—Pic—OH

Boc—(R)Cha—Pic—OEt, 5.6 g (0.014 mol), was mixed with 100 ml of THF, 100 ml of water and 7 g of LiOH. The mixture was stirred at room temperature overnight. The THF was evaporated and the aqueous solution was acidified with KHSO$_4$ (aq) and extracted three times with ethyl acetate. The combined organic phase was washed with water, dried (Na$_2$SO$_4$) and evaporated to give 4.9 g (94%) of Boc—(R)Cha—Pic—OH which was used without further purification. The compound can be crystallized from diisopropyl ether/hexane.

$^1$H-NMR (500 MHz, CDCl$_3$, 2 rotamers, 3.5:1 ratio) δ 0.8–1.1 (m, 2H), 1.1–2.1 (m, 27H; thereof 1.43 (s, 9H, major rotamer), 1.46 (s, 9H, minor)), 2.33 (bd, 1H), 2.80 (bt, 1H, minor), 3.33 (bt, 1H, major), 3.85 (bd, 1H, major), 4.57 (bd, 1H, minor), 4.68 (m, 1H, minor), 4.77 (bq, 1H, major), 5.03 (bs, 1H, minor), 5.33 (bd, 1H, major), 5.56 (m, 1H, major).

(iii) Boc—(R)Cha—Pic—OSu

Boc—(R)Cha—Pic—OH (1 g, 2.6 mmol) was dissolved in DMF (15 ml) at room temperature and then cooled to −18° C., a temperature which was maintained during the additions of the reactants. Hydroxy succinimid (0.60 g, 5.2 mmol) was added and the reaction mixture was stirred for a few minutes until the crystals were dissolved. Dicyclohexyl carbodiimid (0.56 g, 2.7 mmol) dissolved in DMF (10 ml) and precooled was added dropwise to the rection mixture.

After a few minutes at −18° C. the reaction mixture was put into a water bath at 20° C. for 2 h under stirring. The solvent was evaporated, ethyl acetate (40 ml) was added and the precipitated urea was filtered off.

The organic phase was washed once with water, twice with 0.3 M KHSO$_4$, twice with diluted NaHCO$_3$, once with water, once with brine and dried (Na$_2$SO$_4$). The solvent was evaporated and the product dried in vacuo to yield 1.16 g (93%) of the product. According to $^1$H-NMR the product contained two diastereoisomers (epimers in Pic, S/R) in a ratio of 95/5.

$^1$H-NMR (300 MHz, CDCl$_3$, major diastereomer) δ 0.7–2.0 (m, 27H; thereof 1.46 (bs, 9H)), 2.29 (bd, 1H), 2.85 (bs, 4H), 3.40 (m, 1H), 4.5–4.8 (m, 1H), 5.1–5.4 (m, 1H), 5.70 (bd, 1H, major).

Boc—(R)Cha—Mor—OSu

Prepared in the same way as Boc—(R)Cha—Pic—OSu from H—Mor—OEt×HCl except that CH$_3$CN was used as solvent insted of DMF in the formation of the OSu-ester.

Boc—(Me)(R)Cha—Pro—OSu

Prepared in the same way as Boc—(R)Cha—Pro—OSu from Boc—(Me)—(R)Cha—OH.

Boc—(Me)(R)Cha—Pic—OSu

Prepared in the same way as Boc—(R)Cha—Pic—OSu from Boc—(Me)(R)Cha—OH.

Boc—(R,S)Pro(3-Ph)—Pro—OSu

Prepared in the same way as Boc—(R)Cha—Pro—OSu from Boc—(R,S)Pro(3-Ph)—OH.

Boc—(R,S)Pro(3-(trans)Ph)—Pro—OSu (i) Boc—(R,S)Pro(3-(trans)Ph)—Pro—OBn

To a slurry of 1.0 g of Boc—(R,S) Pro(3-(trans)Ph)—OH (3.43 mmol, 1 eq.), 1.04 g of H—Pro—OBn×HCl (4.29 mmol, 1.25 eq.), 0.04 g of HOBt (0.24 mmol, 0.07 eq. ) in 15 ml DMF was added 1.83 g of CME—CDI (4.29 mmol, 1.25 eq.) and 0.525 ml of NMM (4.73 mmol, 1.38 eq.) at room temperature. After stirring an additional 4 days the solvent was evaporated and the residue taken up in 200 ml EtOAc. The organic phase was washed with 2×40 ml of H$_2$O, 2×25 ml of 1M KHSO$_4$, 2×25 ml of 1M NaOH, 2×25 ml of H$_2$O and dried (MgSO$_4$). Evaporation of the solvent and flash chromathography (CH$_2$Cl$_2$/MeOH, 97/3) gave the pure product (44% yield) as a ca: 1:1 mixture of diastereomers.

(ii) Boc—(R,S)Pro(3-(trans)Ph)—Pro—OH

The benzyl ester from the previous step was removed by hydrogenation over 5% Pd/C in EtOH at atmospheric pressure for 4 h. Filtration and evaporation gave the pure product as a ca: 1:1 mixture of diastereomers in quantitative yield.

$^1$H-NMR (CDCl$_3$, 500 MHz, two diastereomers each consisting of two rotamers): δ 1.3–2.4 (m+4s from the Boc groups, total 14H), 2.5–2.9 (m, total 1H), 3.2–3.9 (m, total 5H), 4.3–4.65 (m, total 2H), 7.2–7.5 (m, 5H).

(iii) Boc—(R,S)Pro(3-(trans)Ph)—Pro—OSu

Prepared according to the procedure described for Boc—(R)Cha—OSu from Boc—(R,S)Pro(3-(trans)Ph)—Pro—OH.

Boc—(R,S)Pro(3-(trans)Ch)—Pro—OSu (i) Boc—(R,S)Pro(3-(trans)Ch)—Pro—OH

Boc—(R,S)Pro(3-(trans)Ph)—Pro—OH was hydrogenated over 5% Rh/Al$_2$O$_3$ in methanol together with a small amount of HOAc for 7 days at 0,34 Mpa. Filtration of the catalyst, evaporation of the solvent and flash chromatograpy (CH$_2$Cl$_2$/MeOH, 94/6) gave the pure product as a white solid (mixture of two diastereomers).

(ii) Boc—(R,S)Pro(3-(trans)Ch)—Pro—OSu

Prepared according to the procedure described for Boc—(R)Cha—OSu from Boc—(R,S)Pro(3-(trans)Ch)—Pro—OH.

Boc—(R)Hoc—Pro—OH (i) Boc—(R)Hoc—OH

Boc—(R)Hop—OH, 3.2 g (11.46 mmol) was dissolved in methanol (75 ml). Rhodium on activated aluminium oxide (Rh/Al$_2$O$_3$), 0,5 g was added and the mixture stirred in hydrogen atmosphere at 0.41 MPa for 18 h. The catalyst was filtered off through celite and the solvent evaporated giving the product in almost quantitative yield.

$^1$H-NMR (500 MHz, CDCl$_3$): δ 0.90 (m, 2H), 1.08–1.33 (m, 6H), 1.43 (s, 9H), 1.60–1.74 (m, 6H), 1.88 (bs, 1H), 4.27 (bs, 1H).

(ii) Boc—(R)Hoc—OSu

Prepared in the same way as described for Boc—(R)Cha—OSu from Boc—(R)Hoc—OH.

(iii) Boc—(R)Hoc—Pro—OH

Prepared in the same way as described for Boc—(R)Cha—Pro—OH from Boc—(R)Hoc—OSu.

$^1$H-NMR (500 MHz, CDCl$_3$): δ 0.80–0.94 (m, 2H), 1.05–1.36 (m, 7H), 1.36–1.48 (bs, 9H), 1.48–1.78 (m, 7H), 1.98–2.14 (m, 2H), 2.34 (m, 1H), 3.48 (m, 1H), 3.85 (m, 1H), 4.43 (m, 1H), 4.52 (bd, 1H), 5.26 (bd, 1H), signals of a minor rotamer appears at: δ 1.92, 2.25, 3.58, 4.20 and 4.93.

Boc—(R)Hoc—Pic—OH (i) Boc—(R)Hoc—Pic—OMe

Prepared the same way as described for Boc—(R)Cha—Pic—OEt from Boc—(R)Hoc—OH and H—Pic—OMe×HCl.

(ii) Boc—(R)Hoc—Pic—OH

Prepared in the same way as described for Boc—(R)Cha—Pic—OH from Boc—(R)Hoc—Pic—OMe.

$^1$H-NMR (500 MHz, CDCl$_3$): δ 0.82–0.97 (m, 2H), 1.10–1.36 (m, 7H), 1.36–1.50 (bs, 9H), 1.50–1.82 (m, 11H), 2.35 (bd, 1H) 3.28 (bt. 1H), 3.85 (bd, 1H) 4,63 (m, 1H), 5.33 (bs, 1H), 5.44 (bd, 1H), signals of a minor rotameter appears at: δ 1.88, 2.80, 4.25, 4.55 and 4.97.

Boc—(R)Cha—Aze—OH

Prepared in the same way as described for Boc—(R)Cha—Pic—OH from H—Aze—OEt×HCL.

Boc—(R)Cha—Pic(4-(S)Me)—OH

Prepared in the same way as described for Boc—(R)Cha—Pic—OH from H—Pic(4-(S)Me)—OEt×HCl except that CH$_2$Cl$_2$ was used as solvent.

Boc—(R)Cha—(R)Pic(4-(R)Me)—OSu (i) Boc—(R)Cha—(R)Pic(4-(R)Me)—OEt

Prepared in the same way as described for Boc—(R)Cha—Pic—OEt from H—(R)Pic(4-(R)Me)—OEt×HCl.

(ii) Boc—(R)Cha—(R)Pic(4-(R)Me)—OH

Prepared by using the deprotection (e) on the prduct (i) above.

(iii) Boc—(R)Cha—(R)Pic(4-(R)Me)OSu

Prepared in the same way as described for Boc—(R)Cha—Pic—OSu from Boc—(R)Cha—(R)Pic(4-(R)Me)—OH.

Boc—(R)Cha—(R,S)Pic(4,5-dehydro)—OH

Prepared according to the procedure described for Boc—(R)Cha—Pic—OH from H—(R,S)Pic(4,5-dehydro)—OEt.

Boc—(R)Cgl—Pic—OH (i) Boc—(R)Cgl—Pic—OMe

Pivaloyl chloride (1.000 mL, 8.1 mmol) was added to a solution of Boc—(R)Cgl—OH (2.086 g, 8.1 mmol) and triethyl amine (1.13 mL, 8.1 mmol) in toluene (25 mL) and DMF (5 mL). A mixture of H—Pic—OMe×HCl (1.46 g, 8.1 mmol) and triethyl amine (1.13 mL, 8.1 mmol) in DMF (20 mL) was subsequently added at ice bath temperature. The reaction mixture was slowly allowed to warm up to room temperature and after 24 h it was diluted with water and extracted with toulene. After washing with 0.3M KHSO$_4$, 10% Na$_2$CO$_3$ and brine the solvent was removed in vacuo to give 2.52 g (81%) of colorless oil which was used without further purification.

$^1$H-NMR (500 MHz, CDCl$_3$, 2 rotamers, 5:1 ratio) δ 0.8–1.8 (m, 25H), 2.25 (d, 1H), 2.75 (t, 1H, minor rotamer), 3.3 (t, 1H), 3.7 (s, 3H), 3.85 (d, 1H), 4.3 (t, 1H, minor rotamer), 4.5–4.6 (m, 1H), 5.25 (d, 1H), 5.30 (d, 1H).

(ii) Boc—(R)Cgl—Pic—OH

Prepared according to the procedure for hydrolysis of Boc—(R)Cha—Pic—OEt using the product from (i) above. The product was crystallized from di-isopropyl ether and hexane.

$^1$H-NMR (500 MHz, CDCl$_3$, 2 rotamers, 5:1 ratio) δ 0.8–1.8 (m, 25H), 2.3 (d, 1H), 2.8 (t, 1H, minor rotamer), 3.3 (t, 1H), 3.9 (d, 1H), 4.4 (t, 1H, minor), 4.5–4.6 (m, 1H), 5.1 (s, 1H, minor rotamer), 5.3 (d, 1H), 5.40 (d, 1H).

Boc—(R) Dph—Pic—OH

Prepared in the same way as described for Boc—(R)Cha—Pic—OH from Boc—(R) Dph—OH.

Boc—(R)Dch—Pic—OH

Prepared in the same way as described for Boc—(R)Cha—Pic—OH from Boc—(R)Dch—OH.

Boc-(R)Cha—Pro(5-(S)Me)—OH

Prepared in the same way as described for Boc—(R)Cha—Pic—OH from H—Pro (5-(S)Me)—OMe.

Boc—Nag(Z)

(i) N-Bensyloxycarbonyl-O-methyl isourea

To a stirred solution of concentrated aqueous NaOH (2.8 L, 50% w/w, 19.1M, 53 mol) and water (32 L) at 18° C. was added in two portions O-methylisourea hemisulphate (1.7 kg, 94%, 13.0 mol) and O-methylisourea hydrogensulphate (1.57 kg, 99%, 9.0 mol). The reaction mixture was cooled to 3°–5° C. Benzyl chloroformiate (3.88 kg, 92%, 20.9 mol) was added over a 20 minutes period under cooling and vigorous stirring. The reaction temperature went from 3° to 8° C. during the addition of Z—Cl. The addition funnel was rinsed with 5 liters of water which was added to the reactor. The reaction mixture was stirred at 0°–3° C. for 18 h, filtered and the crystals was washed with cooled (3° C.) water (10 L). Vacuum drying 25° C., 10–20 mbar) for 48 h gave 3.87 kg (89%) of the title compound as a white crystalline powder.

(ii) Boc—Nag(Z)

To a stirred solution Boc—NH—(CH$_2$)$_3$—NH$_2$×HCl (prepared according to Mattingly P. G., Synthesis, 367 (1990)) (3.9 kg, 18.5 mol) in iso-propanol (24 kg) at 60°–70° C. was added in portions over a 30 minutes period KHCO$_3$ (4.2 kg, 42 mol). A slow evolution of CO$_2$ (g) occurs. The mixture was stirred for another 30 minutes followed by addition in portions over a 30 minutes period N-bensyloxycarbonyl-O-methyl isourea (3.74 kg, 18.0 mol). The reaction mixture was stirred at 65°–70° C. for 16 h, cooled to 20° C. and filtered. The precipitate was washed with iso-propanol (10+5 L). The combined filtrates was concentrated at reduced pressure keeping the heating mantle not warmer than 65°–70° C. When approximately 45 liters was distilled off EtOAc (90 L) was added. The reaction mixture was cooled to 20°–25° C., washed with water (10 and 5 L) and brine (5 L), and dried with $Na_2SO_4$ (2 kg). After stirring the rection mixture was filtered and the filter cake was washed with EtOAc (11 and 7 L). The combined filtates were concentrated at reduced pressure keeping the heating mantle not warmer than 40°–50° C. When approximately 90 liters of EtOAc was distilled off, toluene (25 L) was added and the evaporation continued. After collection of approximately another 18 liters of destillate, toulene (20 L) was added under vigorous stirring and the resulting mixture was cooled to −1° to 0° C. and gently stirred over night (17 h). The crystal slurry was filtered and the product was washed with cooled toluene (10 and 5 L).

Vacuum drying (10–20 mbar, 40° C.) for 24 h gave 4.83 kg (13.8 mol, 76%) of Boc—Nag(Z).

$^1$H-NMR (300 MHz, $CDCl_3$): δ 1.41 (s, 9H), 1.6–1.7 (m, 2H), 3.0–3.3 (m, 4H), 4.8–5.0 (bs, 1H), 5.10 (s, 2H), 7.2–7.4 (m, 5H).

Boc—Agm(Z)

(i) Boc—Agm

To a slurry of 14.95 g (65.5 mmol, 1 eq.) of agmatine sulphate (Aldrich), 13.7 ml of $Et_3N$ (98.25 mmol, 1.5 eq.), 165 ml of $H_2O$ and 165 ml of THF was added 21.5 g (98.25 mmol, 1.5 eq.) of $(Boc)_2O$ during 5 minutes at room temperature. The mixture was stirred vigorously over night, evaporated to dryness and the residue was washed with 2×100 ml of $Et_2O$ to give Boc—Agm as a white powder which was used without further purification in the next step.

(ii) Boc—Agm(Z)

To a cold (+5° C.) slurry of the crude Boc—Agm from the previous step (ca: 65.5 mmol) in 180 ml of 4N NaOH and 165 ml of THF was added 24 ml (169 mmol, 2.5 eq) of benzyl chloroformate during 10 minutes. After stirring at room temperature for 4 h methanol (150 ml) was added and the stirring was continued for an additional 20 h at room temperature. The organic solvent was evaporated and 200 ml of $H_2O$ was added to the residue. The basic water phase was extracted with 1×300 ml and 2×200 ml of EtOAc. The combined organic phases was washed with $H_2O$ (2×100 ml), brine (1×100 ml) and dried ($MgSO_4$). Evaporation of the solvent and flash chromathography ($CH_2Cl_2$/MeOH, a stepwise gradient of 97/3, 95/5 and 9/1 was used) gave 14.63 g (58%) of pure Boc—Agm(Z) as a white powder.

$^1$H-NMR ($CDCl_3$, 500 MHz): δ 1.35–1.40 (m, 2H), 1.45 (s, 9H), 1.5–1.6 (m, 2H), 3.0–3.2 (m, 4H), 4.65 (bs, 1H), 5.1 (s, 2H), 7.25–7.40 (m, 5H).

$^{13}$C-NMR ($CDCl_3$, 75.5 MHz): δ 25.44, 27.36, 28.21, 65.83, 79.15, 127.47, 127.66, 128.14, 137.29, 156.47, 161.48, 163.30.

Boc—NH—$(CH_2)_3$—$N_3$

Prepared according to the method described by Mattingly P. G., in Synthesis 1990, 367.

Z—NH—$(CH_2)_2$—$NH_2$

To a cold solution of 6 g ethylene diamine (0.1 mol) and 22 ml triethyl amine in 20 ml of chloroform was added 2.5 g of Z—OSu dissolved in 5 ml of chloroform. The mixture was allowed to reach room temperature and left over night under stirring. Filtration, evaporation of the solvent and flash chromatography ($CH_2Cl_2$/MeOH($NH_3$-saturated), 95/5) gave 0.9 g (46%) of the title compound.

$^1$H-NMR (300 MHz, $CDCl_3$): δ 1.27 (s, 2H), 2.85 (t, 2H), 3.24 (q, 2H), 5.14 (s, 2H), 7.22–7.40 (m, 5H).

Agm×HCl

Prepared from Agm×$H_2SO_4$ (Aldrich) by exchanging the hydrogen sulphate ion for chloride on an ion exchange column.

H—Nag(Z)×2 HCl

Prepared by bubbling HCl(e) into a solution of Boc—Nag(Z) in EtOAc followed by evaporation of the solvent.

BnOOC—$CH_2$—NH—CO—$CH_2$—Br

To a solution of p—TsOH×H—Gly—OBn (5 mmol) and triethyl amine (5 mmol) in 10 ml of $CH_2Cl_2$ was added 2-bromoacetic acid (5 mmol) dissolved in 10 ml of $CH_2Cl_2$ and dicyclohexyl carbodiimide (5 mmol). The mixture was stirred at room temperature over night and filtered. The organic phase was washed twice with 0.2M $KHSO_4$, 0.2M NaOH, brine and dried. Evaporation and flash chromatography ($CH_2Cl_2$/MeOH, 95/5) gave a quantitative yield of the desired compound.

$^1$H-NMR (300 MHz, $CDCl_3$): δ=3.89 (s, 2H), 4.05–4.11 (d, 2H), 5.19 (s, 2H), 7.06 (bs, 1H), 7.3–7.4 (m, 5H).

BnOOC—$CH_2$—OCO—$CH_2$—Br

A mixture of 2.8 g (0.020 mmol) bromoacetic acid, 4.2 g (0.020 mmol) of benzyl bromoacetate and 2.0 g (0.020 mmol) of trietylamine in 25 ml of EtOAc was refluxed for 3 h. It was diluted with more EtOAc and cooled. The solution was washed with dilute HCl and thereafter with $NaHCO_3$(aq) and finally with water. Drying ($Na_2SO_4$) and evaporation followed by flash chromatography (heptane/etylacetate, 75/25) gave the title compound in 26% yield.

$^1$H-NMR (500 MHz, $CDCl_3$): δ 3.95 (s, 2H), 4.75 (s, 2H), 5.23 (s, 2H), 7.35–7.45 (m, 5H).

BnO—$(CH_2)_3$—OTf

Propanediol monobenzyl ether (0.83 g, 5 mmol) was dissolved in dry pyridine (0.6 g, 7 mmol) and dichloromethane (20 ml) and cooled to −15° C. Triflic anhydride, precooled to −15° C., was added and the reaction mixture stirred for 45 min under which the temperature was allowed to rize to 15° C. The solvent was evaporated and the product dissolved in hexane/ethyl acetate 4:1 (10 ml) and filtered through silica. Finally the solvent was evaporated and the product dried in vacuo to yield 0.95 g (64%) of 1-benzyloxy 3-trifluoromethanesulfonylpropane which was used directly (see Example 21).

$^1$H-NMR (500 MHz, $CDCl_3$): δ 2.12 (m, 2H), 3.6 (t, 2H), 4.51 (s, 2H), 4.72 (t, 2H), 7.22–7.42 (m, 5H).

BnO—$(CH_2)_2$—CHO

Prepared by Swern oxidation (described by D. Swern et al., J. Org. Chem., 1978, 2480–82) of BnO-$(CH_2)_3$—OH.

$^1$H-NMR (300 MHz, $CDCl_3$): δ 2.63 (dr, 2H), 3.80 (t, 2H), 4.51 (s, 2H), 7.30 (m, 5H), 9.76 (bt, 1H).

Br—(S)CH($CH_2$OBn)—COOBn (i) Br—(S)CH($CH_2$OBn)—COOH

O-Benzylserine (3.9 g, 19 mmol) in water (10 ml) was added to a solution of sodium bromide (11 g, 107 mmol) in water (20 ml) and sulphuric acid (2 g, 20 mmol). The reaction mixture was cooled to −10° C. and $NaNO_2$ (1.73 g, 25 mmol) was added under vigorous stirring. Another portion of water was added to the thick mixture followed, after a few minutes, by $H_2SO_4$ (1 g, 10 mmol). The mixture was stirred at ambient temperature over night after which it was extracted twice with EtOAc (100 ml). The combined organic phase was washed twice with water and once with brine and dried ($Na_2SO_4$). Evaporation of the solvent gave 3.7 g (75%) of the title compound as a yellow oil which was pure enough to use directly in the next step.

(ii) Br—(S)CH(CH$_2$OBn)—COOBn

To a solution of the crude product from (i) above (2.6 g, 10 mmol) in dry benzene (25 ml) was added oxalyl chloride (2.6 g, 20.5 mmol) and molecular sieves (4 Å, 1 g). The mixture was stirred at ambient temperature under an atmosphere of Argon for 18 h. The molecular sieves was removed by filtration and the solvent evaporated. The slightly yellow residue was dissolved in CH$_3$CN (10 ml) and benzyl alcohol (1 g, 9.2 mmol) was added. The mixture was stirred at ambient temperature for 5 h. The solvent was evaporated and the residue dissolved in Et$_2$O and washed once with 1M NaOH, water, brine and dried (Na$_2$SO$_4$) Evaporation of the solvent followed by flash chromatography (CH$_2$Cl$_2$/MeOH, 95/5) gave 1.8 g (67%) of the desired compound.

$^1$H-NMR (500 MHz, CDCl$_3$): δ 3.82 (dd, 1H), 3.99 (dd, 1H), 4.38 (dd, 1H), 4.56 (s, 2H), 5.23 (s, 2H), 7.23–7.46 (m, 5H).

WORKING EXAMPLES

Example 1

H—(R)Cha—Pro—Agm×2 HOAc (i) Boc—(R)Cha—Pro—Agm×HOAc

Boc—(R)Cha—Pro—OSu (1.7 mmol) and agmatine dihydrochloride (2.0 mmol, 1.18 eq) was dissolved in DMF/H$_2$O 95:5 (35 ml). Triethylamine was added to adjust the pH to about 10 and the solution was stirred at room temperature for 2 days. The solution was evaporated (5 mm Hg/60° C.) until dryness and the crude product was purified by RPLC (CH$_3$CN/NH$_4$OAc (0.1M), 38:62). The desired compound was obtained as a white powder after freeze-drying.

$^1$H NMR (500 MHz, CDCl$_3$/DMSO-d$_6$ 5:2, Two rotamers, 9:1 δ (major rotamer): 0.75–0.90 (m, 2H), 1.1–2.05 (m, 19H), 1.35 (s, 9H) 2.98–3.14 (m, 4H), 3.37 (q, 1H), 3.76 (m, 1H), 4.20 (m, 1H), 4.33 (dd, 1H), 6.30 (d, 1H), 7.05–7.80 (broad m, 5H), 8.67 (broad d, 1H).

Exchange broadened signals of the minor rotamer are unambiguously observed at δ 3.44 (m, 1H), 3.62 (m, 1H), 4.10 (m, 1H), 4.64 (m, 1H), 5.56 (d, 1H), 9.08 (m, 1H).

(ii) H—(R)Cha—Pro—Agm×2 HOAc

A solution of Boc—(R)Cha—Pro—Agm (0.2 mmol) in TFA (2 ml) was stirred at room temperature for 4.5 h. The solvent was evaporated and the remaining oil was subjected to RPLC (CH$_3$CN/NH$_4$OAc (0.1M), 25:75). The diacetate salt was obtained as a white powder after repeated freeze-drying.

$^1$H NMR (500.13 MHz, D$_2$O): δ 0.80 –0.95 (m, 2H), 1.00–1.21 (m, 3H), 1.32 (m, 1H), 1.40–1.78 (m, 12H), 1.83–2.00 (m, 2H), 1.90 (s, acetate), 2.20(m, 1H), 3.06–3.14(m. 4H), 3.50(m, 1H), 3.67 (m, 1H), 4.20–4.30 (m, 2H).

$^{13}$C NMR (75.6 MHz, D$_2$O): guanidine: δ 157.4; carbonyl carbons: δ 169.9, 174.5.

Example 2

Me—(R)Cha—Pro—Agm×2 HOAc (i) Boc—(Me) (R)Cha—Pro—Agm

To a solution of 479.6 mg (1 mmol, 1 eq.) of Boc—(Me)(R)Cha—Pro—OSu and 500 ml of NMM in 16 ml DMF/H$_2$O (15/1) was added 166.5 mg (1.2 mmol, 1.2 eq.) of Agm×HCl at room temperature. The reaction was stirred an additional 70 h and the solvent was evaporated to give a crude product as an oil. This was used without purification in the next step.

(ii) Me—(R)Cha—Pro—Agm×2 HOAc

The crude oil from the previous step was dissolved in 10 ml TFA/CH$_2$Cl$_2$ (1:4) at room temperature. After stirring for 2 h 25 min the solvent was evaporated and the crude product was purified with RPLC (CH$_3$CN/NH$_4$OAc(0.1M), 35/65) to give the desired product as a white powder after freeze-drying.

$^1$H-NMR (500 MHz, D$_2$O): δ 0.93–1.05 (m, 2H), 1.10–1.29 (m, 3H), 1.33–1.43 (m, 1H), 1.50–1.80 (m, 12H), 1.88–2.10 (m, 2H, 1.92 (s, acetate), 2.27–2.36 (m, 1H), 2.68 (s, 3H), 3.15–3.23 (m, 3H), 3.24–3.31 (m, 1H), 3.57–3.66 (m, 1H), 3.76–3.83 (m, 1H), 4.28 (t, 1H), 4.39 (dd, 1H).

$^{13}$C-NMR (125.76 MHz, D$_2$O): guanidine: δ 157.24; carbonyl carbons: δ 174.03, 168.24.

Example 3

HO—(CH$_2$)$_3$—(R)Cha—Pro—Agm×2 HCl (i) Boc—(R)—Cha—Pro—Agm(Z)

Boc—Agm(Z) (1 eq) was dissolved in TFA/CH$_2$Cl$_2$ (1:4, ca: 6 ml/mmol) and stirred at room temperature for ca: 2 h. The solvent was evaporated and the product dissolved together with Boc—(R)Cha—Pro—OSu (1 eq) in DMF (ca: 1 ml/mmol), the pH was adjusted with NMM to ca: 9 and the mixture was stirred at room temperature for 20 h. The solvent was evaporated in vacuo, the crude product dissolved in CH$_2$Cl$_2$ and washed three times with water and once with brine. After drying (sodium sulphate) the solvent was evaporated and the product flash chromatographed (CH$_2$Cl$_2$/MeOH) affording Boc—(R)Cha—Pro—Agm(Z) as a white powder.

(ii) H—(R)Cha—Pro—Agm(Z)

Boc—(R)Cha—Pro—Agm(Z) was dissolved in TFA/CH$_2$Cl$_2$ (1:4, ca: 6 ml/mmol) and stirred at room temperature for 2 h. The solvent was evaporated, the product dissolved in 0.2M NaOH (20 ml/mmol) and extracted twice with dichloromethane. The organic layers were combined and washed with brine, dried (sodium sulphate) and the solvent evaporated to yield H—(R)Cha—Pro—Agm(Z) as a white powder.

(iii) BnO—(CH$_2$)$_3$—(R)Cha—Pro—Agm(Z)

H—(R)Cha—Pro—Agm(Z) (1 mmol) was dissolved in methanol (10 ml). Triethylammonium hydrochloride (1 mmol), sodium cyanoborohydride (0.7 mmol) and thereafter BnO—(CH$_2$)$_2$—CHO (1.05 mmol) were added and the reaction mixture stirred at room temperature over night. The solvent was evaporated and the crude product was dissolved in ethyl acetate, washed twice with water, once with brine and dried over sodium sulphate. The solvent was evaporated and the crude product was purified by flash chromatography (EtOAc/MeOH).

(iv) HO—(CH$_2$)$_3$—(R)Cha—Pro—Agm×2 HCl

Prepared by using deprotection procedure (d) on the product (iii) above.

$^1$H-NMR (500 MHz, D$_2$O): δ 0.72 (m, minor rotamer), 0.84 (m, minor rotamer), 0.87–1.03 (m, 2H) , 1.03-1-26 (m, 3H), 1.28–1.40 (bs, 1H), 1.44–1.80 (m, 11H), 1.80–1.95 (bs, 3H), 1.95–2.10 (bs, 2H), 2.28 (m, 1H), 3.04 (m, 1H), 3.08–3.27 (m, 5H), 3.58 (bs, 1H), 3.67 (bs, 2H), 3.78 (m, 1H), 4.12 (bd, minor rotamer), 4.30 (m, 1H), 4.37 (m, 1H).

$^{13}$C-NMR (125 MHz, D$_2$O): guanidine: δ 157.26; carbonyl carbons: δ 174.06, 168.36.

Example 4

HOOC—CH₂—(R)Cha—Pro—Agm×HOAc

General Procedure for the alkylation of the N-terminal.

This procedure is described in more general terms and will be referred to in the Examples below together with the alkylating agent used in each specific Example.

The peptide to be alkylated (1 eq) and the alkylating agent (1.1–1.2 eq) were dissolved in acetonitrile (ca 10 ml/mmol). Potassium carbonate (2.0–2.2 eq) was added and the reaction mixture stirred at 50°–60° C. until the starting material was consumed (TLC, usually 1–5 h). Filtration, evaporation of the solvent and flash chromatography (CH₂Cl₂/MeOH, CH₂Cl₂/MeOH(NH₃-saturated) or EtOAc/MeOH, ca 9/1) gave the alkylated product after evaporation of the solvent.

(i) BnOOC—CH₂—(R)Cha—Pro—Agm(Z)

Prepared from H—(R)Cha—Pro—Agm(Z) (See Example 3) and Br—CH₂COOBn according to the procedure described above.

(ii) HOOC—CH₂—(R)Cha—Pro—Agm×HOAc

Prepared by using the deprotection procedure (b) on the product (i) above.

¹H-NMR (300 MHz, MeOD): δ 0.9–1.1 (m, 2H), 1.1–2.3 (m, 19H) 1.95 (s, acetate), 3.1–3.2 (m, 4H), 3.2–3.65 (m, 3H), 3.85 (m, 1H), 4.0 (bt, 1H), 4.35 (dd, 1H).

¹³C-NMR (75 MHz, D₂O): guanidine: δ 157.55; carbonyl carbons: δ 168.71, 171.37 and 174.3.

Example 5

ⁱPr—OOC—CH₂—(R)Cha—Pro—Agm×HOAc

Alkylation as in Example 4 using H—(R)Cha—Pro—Agm(Z) (See Example 3) and Br—CH₂COOⁱPr followed by deprotection procedure (b) gave the title compound.

¹H-NMR (500 MHz, MeOD): δ 0.85–1.05 (m, 2H), 1.1–1.35 (m, 9H; thereof 1.23 (d, 3H), 1.25 (d, 3H)), 1.35–2.02 (m, 14H) 1.92 (s, acetate), 2.08 (m, 1H), 2.2 (m, 1H), 3.07–3.45 (m, 6H), 3.55 (m, 1H), 3.7–3.8 (m, 2H), 4.3 (dd, 1H), 5.05 (m, 1H).

¹³C-NMR (125 MHz, D₂O): guanidine: δ 157.39; carbonyl carbons: δ 171.10, 172.76 and 174.44.

Example 6

HOOC—CH₂—(Me)(R)Cha—Pro—Agm×2 TFA (i) Me—(R)Cha—Pro—Agm(Z)

Prepared from Boc—(Me)(R)Cha—Pro—OSu in the same way as described for H—(R)Cha—Pro—Agm(Z) in Example 3.

(ii) HOOC—CH₂—(Me)(R)Cha—Pro—Agm×2 TFA

Alkylation as in Example 4 using Me—(R)Cha—Pro—Agm(Z) and Br—CH₂COOBn followed by deprotection procedure (b) gave the title compound.

¹H-NMR (300 MHz, D₂O): δ 0.9–1.35 (m, 6H), 1.5–2.2 (m, 14H), 2.25–2.45 (m, 1H), 3.12 (s, 3H), 3.15–3.35 (m, 4H), 3.6–3.75 (m, 1H), 3.8–3.95 (m, 1H), 4.22 (apparent bs, 2H), 4.45 (m, 1H), 4.6 (bt, 1H).

¹³C-NMR (75.47 MHz, D₂O): guanidine: δ 157.52; carbonyl carbons: δ 173.86, 168.79, 167.38.

Example 7

HOOC—(R,S)CH(Me)—(R)Cha—Pro—Agm×HOAc

Alkylation as in Example 4 using H—(R)Cha—Pro—Agm(Z) (See Example 3) and Br—CH(Me)COOBn followed by deprotection procedure (a) gave the title compound as a mixture of two diastereomers.

Example 8

HOOC—(RorS)CH(Me)—(R)Cha—Pro—Agm/a×HOAc

Obtained by separating the diastereomers formed in Example 7 using RPLC (CH₃CN/NH₄OAc (0.1M), 1/4). This diastereomer came out first of the two from the column.

¹H-NMR (500 MHz, D₂O; 2 rotamers ca: 5:1 ratio): δ 0.74 (m, minor rotamer), 1.01 (m, 2H), 1.10–1.33 (m, 3H), 1.48–1.88 (m, 15H; thereof 1.51 (d, 3H)), 1.92–2.12 (m, 3H) 1.96 (s, acetate), 2.30 (m, 1H), 3.20 (m, 3H), 3.38 (m, 1H), 3.47 (q, minor rotamer), 3.53–3.68 (m, 2H), 3.73 (m, 1H), 4.20 (d, minor rotamer), 4.33 (m, 1H), 4.38 (m, 1H), 4.51 (d, minor rotamer).

¹³C-NMR (125 MHz, D₂O): guanidine: δ 157.38; carbonyl carbons: δ 174.11, 173.45, 168.64.

Example 9

HOOC—(RorS)CH(Me)—(R)Cha—Pro—Agm/b×HOAc

The diastereomer that came out after the first one from the column in the separation in Example 8 is the title compound above.

¹H-NMR (500 MHz, D₂O, 2 rotamers ca 9:1 ratio): δ 0.88 (m, minor rotamer), 1.05 (m, 2H), 1.12–1.33 (m, 3H), 1.42 (bs, 1H), 1.50–1.88 (m, 15H; thereof 1.55 (d, 3H)), 1.93–2.13 (m, 3H) 1.95 (s, acetate), 2.30 (m, 1H), 2.40 (m, minor rotamer), 3.22 (t, 2H), 3.28 (t, 2H), 3.64 (m, 1H), 3.70 (q, 1H), 3.98 (t, minor rotamer), 4.35 (t, 1H), 4.41 (dd, 1H).

Example 10

HOOC—(RorS)CH(ⁿPr)—(R)Cha—Pro—Agm/a×HOAc

Alkylation as in Example 4 using H—(R)Cha—Pro—Agm(Z) (See Example 3) and Br—CH(ⁿPr)COOEt and deprotection procedure (e) followed by deprotection procedure (b) gave HOOC—(R,S)CH(ⁿPr)—(R)Cha—Pro—Agm. The title compound was obtained by separating the diastereomers by RPLC (CH₃CN/NH₄OAc (0.1M), 1/4) and freeze drying (H₂O) after evaportion of the solvent. This diastereomer came out first of the two from the column.

¹H-NMR (300 MHz, MeOD): δ 0.8–1.1 (m, 5H; thereof 0.92 (t, 3H)), 1.1–2.1 (m, 22H) 1.95 (s, acetate), 2.2 (m, 1H), 3.1–3.35 (m, 5H), 3.48 (m, 1H), 3.88 (m, 1H), 4.0 (m, 1H), 4.4 (dd, 1H).

¹³C-NMR (75 MHz, D₂O): guanidine: δ 157.50; carbonyl carbons: δ 168.55 and 174.16.

Example 11

HOOC—(RorS)CH(ⁿPr)—(R) Cha—Pro—Agm/b×HOAc

The other diastereomer from the separation in Example 10 which came out after the first one from the column is the title compound above.

¹H-NMR (500 MHz, MeOD): δ 0.85–1.05 (m, 5H; thereof 0.95 (t, 3H)) 1.1–2.08 (m, 22H) 1.9 (s, acetate), 2.14 (m, 1H), 3.1–3.4 (m, 5H), 3.45 (m, 1H), 3.62 (m, 1H), 3.80 (m, 1H), 4.34 (dd, 1H).

¹³C-NMR (75 MHz, D₂O): guanidine: δ 157.53; carbonyl carbons: δ 169.01 and 174.27.

Example 12

HOOC—(RorS)CH(Ph)—(R)Cha—Pro—Agm/bxHOAc (i) ᵗBuOOC—(RorS)CH(Ph)—(R)Cha—Pro—Agm(Z)

A mixture of H—(R)Cha—Pro—Agm(Z) (See Example 3) (0.55 mmol), tert.butyl-(R,S)phenyl bromoacetate (0.66 mmol), K₂CO₃ (1.4 mmol) in CH₃CN (10 ml) was stirred at room temperature for 28 h and an additional 5 h at 60° C. The diastereomeric mixture (ca: 3:1, according to NMR) was filtered and evaporated. The remaining oil was twice subjected to flash chromatography (CH₂Cl₂/MeOH, 92/8), which resulted in a complete separation of the two diastereomers ($R_f$=0.36 (minor isomer) and 0.27 (major isomer), respectively).

¹H NMR of major isomer (500.13 MHz, CDCl₃): δ 0.79 (quart,1H), 0.90 (quart,1H), 1.06–1.70 (m, H), 1.37 (s,9H), 1.85–2.03 (m, 3H), 2.20 (m, 1H), 3.10–3.24 (m, 3H), 3.25–3.38 (m, 2H), 3.42 (m, 1H), 3.53 (m, 1H), 4.30 (s, 1H), 4.49 (dd, 1H), 5.08 (s, 2H), 7.19–7.40 (m, 10H); broad NH signals are observed in the region 6.7–8.6.

(ii) HOOC—(RorS)CH(Ph)—(R)Cha—Pro—Agm/bx HOAc

The major isomer (50 mmol) and thioanisole (0.5 mmol) dissolved in TFA was kept at room temperature for 8 h. After evaporation (0.1 mm Hg) for 5 h, the remaining oil was purified on RPLC (CH₃CN/NH₄OAc (0.1M), 2:3) to give the title compound after evaporation of the solvent and freeze-drying.

¹H NMR (500.13 MHz, MeOD): δ 0.85–1.01 (m, 2H), 1.13–1.38 (m, 4H), 1.53–2.05 (m, 14H), 1.92 (s, acetate) 2.18 (m, 1H), 3.08–3.26 (m, 3H), 3.32–3.45 (m, 2H), 3.64 (m, 1H), 3.93 (t, 1H), 4.37 (dd, 1H), 4.43 (s,1H), 7.28–7.50 (m, 5H).

¹³C NMR (125.6 MHz, MeOD): guanidine: δ 158.7; carbonyl carbons: δ 173.8, 174.7, 177.0.

Example 13

HOOC—(R,S)CH(CH₂CH₂Ph)—(R)Cha—Pro—Agmx HOAc

Alkylation as in Example 4 using H—(R)Cha—Pro—Agm(Z) (See Example 3) and Br—CH(CH₂—CH₂—Ph)COOEt and deprotection procedure (a) followed by deprotection procedure (e) gave HOOC—(R,S)CH(CH₂—CH₂—Ph)—(R)Cha—Pro—Agm.

Example 14

HOOC—(RorS)CH(CH₂CH₂Ph)—(R)Cha—Pro—Agm/ax2 TFA

The title compound was obtained by separating the diastereomers obtained in Example 13 by RPLC (CH₃CN/NH₄OAc (0.1M), 2/3) and freeze drying (H₂O/TFA) after evaportion of the solvent. This diastereomer came out first of the two from the column is the title compound above.

¹H-NMR (500 MHz, MeOD): δ 0.93–1.11. (m, 2H), 1.24 (m, 1H), 1.29–1.40 (m, 2H), 1.52–1.85 (m, 11H), 1.89–2.11 (m, 4H), 2.14–2.32 (m, 3H), 2.83 (t, 2H), 3.14 (t, 2H), 3.24 (t, 2H), 3.50 (q, 1H), 3.70 (m, 1H), 4.00 (t, 1H), 4.36–4.42 (m, 2H), 7.17–7.31 (m, 5H).

¹³C-NMR (125 MHz, MeOD): guanidine: δ 158.66; carbonyl carbons: δ 168.08, 171.53, 174.16.

Example 15

HOOC—CH₂—CH₂—(R)Cha—Pro—AgmxHOAc (i) BnOOC—CH₂—CH₂—(R)Cha—Pro—Agm(Z)

Benzyl acrylate (1.1 eq) and H—(R)Cha—Pro—Agm(Z) (See Example 3) (1 eq) were dissolved in ethanol (20 ml/mmol) and stirred at room temperature for 20 h. The solvent was evaporated and the crude product purified by flash chromatography (CH₂Cl₂/MeOH(NH₃-saturated), 95/5). Finally the solvent was evaporated and the product dried in vacuo.

¹H-NMR (500 MHz, CDCl₃): δ 0.7–0.95 (m, 2H), 1.0–1.5 (m, 10H), 1.5–1.75 (m, 5H), 1.75–1.92 (m, 2H), 2.0 (m, 1H), 2.17 (bs, 1H), 2.45 (m, 2H), 2.63 (m, 1H), 2.79 (m, 1H), 2.97–3.25 (m, 4H), 3.33 (m, 2H), 3.52 (bt, 1H), 4.45 (bd, 1H), 4.95–5.12 (m, 4H), 7.13–7.4 (m, 10H).

(ii) HOOC—CH₂—CH₂—(R)Cha—Pro—AgmxHOAc

Prepared by using the deprotection procedure (a) on the product (i) above.

¹H-NMR (500 MHz, D₂O): δ 0.88 (m, 2H), 1.00–1.23 (m, 3H), 1.33 (bs, 1H), 1.42–1.72 (m, 11H), 1.78–2.00 (m, 3H) 1.94 (s, acetate), 2.18 (m, 1H), 2.52 (m, 2H), 3.03–3.20 (m, 6H), 3.50 (m, 1H), 3.72 (m, 1H), 4.23 (m, 1H), 4.30 (m, 1H).

¹³C-NMR (125 MHz, D₂O): guanidine: δ 157.25; carbonyl carbons: δ 178.07, 173.96, 168.24.

Example 16

EtOOC—CO—(R)Cha—Pro—AgmxHOAc (i) EtOOC—CO—(R)Cha—Pro—Agm(Z)

To a cold (–10° C.) solution of H—(R)Cha—Pro—Agm(Z) (See Example 3) (0.46 g, 0.89 mmol) and NMM (199 mg, 1.97 mmol) in 10 ml of THF was added Cl—CO—COOEt (134 mg, 0.98 mmol) dissolved in 3 ml of THF. The mixture was keept at –10° C. for one hour after which it was stirred at room temperature for another hour. The solvent was evaporated and the residue was dissolved in ethyl acetate. The organic phase was washed twice with water and dried (Na₂SO₄). Evaporation of the solvent and crystallization from EtOAc gave 0.275 g (50%) of the title compound as white crystals.

(ii) EtOOC—CO—(R)Cha—Pro—AgmxHOAc

Prepared by using the deprotection procedure (b) on the product (i) above.

¹H-NMR (300 MHz, MeOD): δ 0.9–2.25 (m, 24H; thereof 1.17 (t, 3H)) 1.90 (s, acetate), 3.1–3.25 (m, 4H), 3.5–3.65 (m, 3H; thereof 3.59 (q,2H)), 3.88 (m, 1H), 4.35 (m, 1H), 4.69 (dd, 1H).

¹³C-NMR (75.5 MHz, MeOD): guanidine: δ 157.56 and carbonyl carbons: δ 159.21, 160.74, 172.81, 174.56.

Example 17

(R,S)Bla—(R)Cha—Pro—Agmx2 TFA

Alkylation as in Example 4 using H—(R)Cha—Pro—Agm(Z) (See Example 3) and α-bromo butyrolacton followed by deprotection procedure (a) gave the title compound as a mixture of two diastereomers.

¹H-NMR (500 MHz, D₂O, mixture of diastereomers ca: 1/1): δ 0.93–1.06 (m, 2H), 1.09–1.30 (m, 3H), 1.37–1.49 (m, 1H), 1.50–1.87 (m, 11H), 1.89–2.10 (m, 3H), 2.24–2.36 (m, 1H), 2.44–2.56 (m, 1H), 2.72–2.85 (m, 1H), 3.10–3.30 (m, 4H), 3.56–3.65 (m, 1H), 3.75–3.84 (m, 1H), 4.2–5.0 (m, 5H, partially hidden by the H-O-D signal).

¹³C-NMR (125.76 MHz, D₂O) guanidine: δ 157.34 (peaks overlapping); carbonyl carbons: δ 174.34, 173.90, 173.62, 167.88, 167.58 (two peaks are overlapping).

Example 18

HOOC—(RorS)CH(CH₂CH₂Ph)—(R)Cha—Pro—Agm/ bx2 TFA

The title compound was obtained by treating the diastereomer in Example 13 by the same way as described in Example 14. This diastereomer came out after the first one from the column.

¹H-NMR (500 MHz, MeOD): δ 0.95–1.06 (m, 2H), 1.14–1.40 (m, 4H), 1.48–1.84 (m, 11H), 1.87–2.30 (m, 6H), 2.72–2.90 (m, 2H), 3.12–3.32 (m, 4H), 3.52 (m, 1H), 3.72 (m, 1H), 4.04 (dd, 1H), 4.27 (t, 1H), 4.37 (dd, 1H), 7.17–7.32 (m, 5H).

¹³C-NMR (125 MHz, MeOD): guanidine: δ 158.68; carbonyl carbons: δ 168.14, 171.46, 174.03.

Example 19

H—(R)Cha—Pro—Nag×2 HOAc (i) Z—(R)Cha—Pro—NH—(CH₂)₃—NH(Boc)

To a solution of Z—(R)Cha—Pro—OSu (1 mmol) in 1 ml of DMF at 0° C. was added H₂N—(CH₂)₃—NH(Boc) (See Preparation of starting material) dissolved in 1 ml of DMF and the pH was adjusted to ca: 9 with NMM. The reaction was stirred at room temperature for 3 days after wich it was poured out on water. The aqueous phase was extracted four times with EtOAc. The combined organic phase was washed twice with 0.3M KHSO₄, 0.2M NaOH, brine and dried. Evaporation and flash chromatography (EtOAc/petroleum ether, 4/1) gave the title compond in 59% yield.

(ii) Z—(R)Cha—Pro—NH—(CH₂)₃—NH₂

Z—(R)Cha—Pro—NH—(CH₂)₃—NH(Boc) (0.6 mmol) was dissolved in CH₂Cl₂ (8 ml). TFA (2 ml) was added and the reaction mixture was stirred for 1 h. The solvent was evaporated and the residue was dissolved in CH₂Cl₂, washed twice with 0.2M NaOH and dried (Na₂SO₄). Evaporation of the solvent gave the amine in 93% yield.

¹H-NMR (500 MHz, CDCl₃): δ 0.79–1.03 (m, 2H), 1.05–1.75 (m, 15H), 1.84–2.08 (m, 4H), 2.36 (m, 1H), 2.66 (m, 2H), 3.25 (m, 2H), 3.43 (q, 1H), 3.85 (m, 1H), 4.45 (m, 1H), 4.56 (d, 1H) 5.09 (m, 2H), 5.35 (d, 1H), 7.30–7.45 (m, 5H).

(iii) Z—(R)Cha—Pro—Nag×HOAc

Z—(R)Cha—Pro—NH—(CH₂)₃—NH₂ (0.55 mmol, 1 eq) was dissolved in DMF (2 ml) and the pH adjusted with triethylamine to 8–9. 3,5-Dimethyl-1-pyrazolylformamidinium nitrate (0.55 mmol, 1 eq) dissolved in DMF (1 ml) was added and the reaction mixture stirred at room temperature for three days. The solvent was evaporated, the crude product freeze-dried (H₂O) and purified with RPLC (CH₃CN/NH₄OAc (0.1M), 4/6) to give the title compound in 93% yield after evaporation of the solvent and freeze-drying (H₂O).

(iv) H—(R)Cha—Pro—Nag×2 HOAc

Prepared by using the deprotection procedure (a) on the product (iii) above.

¹H-NMR (500 MHz, D₂O): δ 0.82–1.03 (m, 2H), 1.03–1.28 (m, 3H) 1.35 (m, 1H), 1.53–1.82 (m, 9H), 1.82–2.05 (m, 3H) 1.89 (s, acetate), 2.24 (m, 1H), 3.15 (t, 2H), 3.23 (q, 2H), 3.55 (m, 1H), 3.72 (m, 1H), 4.27–4.34 (m, 2H).

¹³C-NMR (125 MHz, D₂O): guanidine: δ 157.37; carbonyl carbons: δ 169.81, 174.52.

Example 20

ⁿBu—(R)Cha—Pro—Nag×2 HOAc (i) H—(R)Cha—Pro—Nag(Z)

Prepared from Boc—(R)Cha—Pro—OSu and Boc—Nag(Z) in the same way as described for H—(R)Cha—Pro—Agm(Z) in Example 3.

¹H-NMR (500 MHz, CDCl₃ ): δ 0.8–1.03 (m, 2H), 1.10–1.50 (m, 6H), 1.60–1.83 (m, 8H), 1.87–2.20 (m, 3H), 3.15 (m, 1H), 3.25 (m, 2H), 3.42 (m, 2H), 3.63 (dd, 1H), 3.70 (m, 1H), 4.36 (bs, 1H), 5.07 (s, 2H), 7.22–7.43 (m, 5H).

(ii) ⁿBu—(R)Cha—Pro—Nag(Z)

H—(R)Cha—Pro—Nag(Z) (0.5 g, 1 mmol) was dissolved in methanol (10 ml). Triethylammonium hydrochloride (0.1 g, 1 mmol), sodium cyanoborohydride (44 mg, 0.7 mmol) and thereafter butyric aldehyde (76 mg, 1.05 mmol) were added and the reaction mixture stirred at room temperature for 20 h. The solvent was evaporated and the crude product was dissolved in ethyl acetate, washed twice with water, once with brine and dried over sodium sulphate. The solvent was evaporated and the crude product was purified by flash chromatography (EtOAc/EtOH/Et₃N, 88/10/2). Finally the solvent was evaporated and the product dried in vacuo to yield 0.22 g (40%) of ⁿBu—(R)Cha—Pro—Nag(Z).

¹H-NMR (500 MHz, CDCl₃): δ 0.82–1.0 (m, 5H; thereof 0.88 (t, 3H)), 1.08–1.49(m, 10H), 1.58–1.8 (m, 7H), 1.88–2.22 (m, 3H), 2.4 (m, 1H), 2.5 (m, 1H), 3.05 (bs, 1H), 3.3 (m, 1H), 3.4–3.53 (m, 3H), 3.73 (m, 1H), 4.42 (bs, 1H), 5.1 (s, 2H), 7.25–7.43 (m, 5H).

(iii) ⁿBu—(R)Cha—Pro—Nag×2 HOAc

Prepared by using the deprotection procedure (a) on the product (ii) above.

¹H-NMR (300 MHz, D₂O): δ 0.94 (t, 2H), 1.10–1.31 (m, 3H), 1.38 (m, 3H), 1.55–1.88 (m, 11H), 1.88–2.15 (m, 3H) 1.95 (s, acetate), 2.34 (m, 1H), 2.95 (m, 1H), 3.08 (m, 1H), 3.24 (t, 2H), 3.30 (m, 2H), 3.66 (m, 1H), 3.82 (m, 1H), 4.32 (t, 1H), 4.41 (dd, 1H).

¹³C-NMR (125 MHz, D₂O): guanidine: δ 157.40; carbonyl carbons: δ 180.39, 174.28, 168.55.

Example 21

HO—(CH₂)₃—(R)Cha—Pro—Nag×2 TFA (i) BnO—(CH₂)₃—(R)Cha—Pro—Nag(Z)

1-Benzyloxy 3-trifluoromethanesulfonylpropane (See Prep. of Starting Materials) (0.5 g, 1 mmol) and H—(R)Cha—Pro—Nag(Z) (See Example 20) were dissolved in tetrahydrofurane (10 ml). Potassium carbonate (0.28 g, 2 mmol) was added and the reaction mixture was stirred at room temperature for two hours. The solvent was evaporated and the crude product extracted with ethyl acetate/water. The organic phase was washed once with aqueous sodium hydrogen carbonate, once with water and once with brine. After drying over sodium sulphate the solvent was evaporated and the crude product flash chromatographed (CH₂CH₂/MeOH(NH₃-saturated), 95:5). Finally the solvent was evaporated and the product dried in vacuo to yield 0.29 g (45%) of the title compound.

$^1$H-NMR (500 MHz, CDCl₃): δ 0.77–1.03 (m, 2H), 1.03–2.18 (m, 19H), 2.52 (m, 1H), 2.64 (m, 1H), 3.03 (bs, 1H), 3.1–3.6 (m, 7H), 3.66 (m, 1H), 4.41 (bs, 1H), 4.46 (s, 2H), 5.08 (s, 2H), 7.2–7.4 (m, 5H), 7.55 (m, 1H).

(ii) HO—(CH₂)₃—(R)Cha—Pro—Nag×2 TFA

Prepared by using the deprotection procedure (a) on the product (i) above.

$^1$H-NMR (500 MHz, D₂O): δ 1.00 (bs, 2H), 1.10–1.32 (m, 3H), 1.40 (bs, 1H), 1.55–2.15 (m, 14H), 2.30 (m, 1H), 3.05–3.35 (m, 6H), 3.57–3.75 (m, 3H), 3.81 (bs, 1H), 4.35 (bs, 1H), 4.42 (bs, 1H).

Example 22

HOOC—CH₂—(R)Cha—Pro—Nag×HOAc (i) H—(R)Cha—Pro—NH—(CH₂)₃—N₃

Prepared in the same way as H—(R)Cha—Pro—Agm(Z) (See Example 3) starting from Boc—(R)Cha—Pro—OSu and Boc—NH—(CH₂)₃—N₃ (replacing Boc—Agm(Z)).

(ii) EtOOC—CH₂—(R)Cha—Pro—NH—(CH₂)₃—NH₂×HOAc

Alkylation as in Example 4 using H—(R)Cha—Pro—NH—(CH₂)₃—N₃ and EtOOC—CH₂—Br followed by deprotection procedure (a) to reduce the azide gave the title compound.

(iii) EtOOC—CH₂—(R)Cha—Pro—Nag×HOAc

The same procedure as described in Example 19 (iii) for Z—(R)Cha—Pro—Nag was used to accomplish the guanidation of the amine from (ii) above. The title compound was obtained in a pure form after RPLC (CH₃CN/NH₄OAc (0.1M), 3/7) evaporation of the solvent and freeze drying (H₂O).

(iv) HOOC—CH₂—(R)Cha—Pro—Nag×HOAc

Prepared by using the deprotection procedure (e) on the product (iii) above.

$^1$H-NMR (500 MHz, D₂O): δ 0.99 (m, 2H), 1.09–1.30 (m, 3H), 1.44 (m, 1H), 1.59–2.09 (m, 12H) 1.92 (s, acetate), 2.29 (m, 1H), 3.20 (t, 2H), 3.28 (m, 2H), 3.52–3.63 (m, 3H), 3.76 (m, 1H), 4.38 (dd, 1H), 4.42 (t, 1H).

$^{13}$C-NMR (125 MHz, D₂O): guanidine: δ 157.43; carbonyl carbons: δ 168.72, 171.36, 174.35.

Example 23

EtOOC—CH₂—(R)Cha—Pro—Nag×HOAc

Prepared according to example 22 (iii).

$^1$H-NMR (300 MHz, D₂O): δ 1.07 (m, 2H), 1.17–1.59 (m, 7H; thereof 1.38 (t, 3H)), 1.60–2.24 (m, 12H) 2.04 (s, acetate), 2.39 (m, 1H), 3.31 (t, 2H), 3.39 (t, 2H), 3.63–3.90 (m, 4H), 4.12 (t, 1H), 4.36 (q, 2H), 4.46 (dd, 1H).

$^{13}$C-NMR (75 MHz, D₂O): guanidine: δ 157.37; carbonyl carbons: δ 173.73, 175.09, 175.70.

Example 24

$^i$PrOOC—CH₂—(R)Cha—Pro—Nag×HOAc

Alkylation as in Example 4 using H—(R)Cha—Pro—Nag(Z) (See Example 20) and Br—CH₂COO$^i$Pr followed by deprotection procedure (b) gave the title compound.

$^1$H-NMR (500 MHz, MeOD): δ 0.85–1.05 (m, 2H), 1.1–2.15 (m, 22H; thereof 1.23 (d, 3H), 1.25 (d, 3H)), 1.92 (s, acetate), 2.2 (m, 1H), 3.10–3.35 (m, 5H), 3.4 (m, 1H), 3.55 (m, 1H), 3.65–3.8 (m, 2H), 4.28 (dd, 1H), 5.03 (m, 1H).

$^{13}$C-NMR (125 MHz, D₂O): guanidine: δ 157.39; carbonyl carbons: δ 170.40, 172.00 and 174.50.

Example 25

$^t$BuOOC—CH₂—(R)Cha—Pro—Nag×2 TFA

Alkylation as in Example 4 using H—(R)Cha—Pro—Nag(Z) (See Example 20) and Br—CH₂COO$^t$Bu followed by deprotection procedure (b) gave the title compound.

$^1$H-NMR (300 MHz, MeOD): δ 0.9–1.15 (m, 2H), 1.15–2.15 (m, 25H; thereof 1.55 (bs, 9H)), 2.3 (m, 1H), 3.15–3.45 (m, 4H), 3.55 (m, 1H), 3.7–3.95 (m, 3H), 4.3–4.4 (m, 2H).

$^{13}$C-NMR (75 MHz, D₂O): guanidine: δ 157.55; carbonyl carbons: δ 166.55, 168.13 and 174.33.

Example 26

HOOC—CH₂—OOC—CH₂—(R)Cha—Pro—Nag× HOAc (i) BnOOC—CH₂—OOC—CH₂—(R)Cha—Pro—Nag(Z)

H—(R)Cha—Pro—Nag(Z) (See Example 20), 0.20 g (0.40 mmol), was mixed with 0.115 g (0.40 mmol) of benzyloxycarbonylmethyl bromoacetate, 55 mg of K₂CO₃ (0.40 mmol) and 5 ml of CH₃CN. The mixture was stirred at room temperature for 6 h. The solvent was evaporated and the crude product chromatographed (CH₂Cl₂/MeOH, 9/1) to give 0.20 g (71%) of the desired compound after evaporation of the solvent.

(ii) HOOC—CH₂—OOC—CH₂—(R)Cha—Pro—Nag× HOAc

Prepared by using the deprotection procedure (a) on the product (i) above.

$^1$H-NMR (500 MHz, MeOD): δ 0.85–1.1 (m, 2H), 1.1–1.6 (m, 8H), 1.6–2.15 (m, 10H) 1.99 (s, acetate), 2.23 (m, 1H), 3.1–3.4 (m, 4H), 3.45–3.65 (m, 4H), 3.7–3.9 (m, 3H), 4.34 (m, 1H), 4.48 (dd, 2H).

$^{13}$C-NMR (125 MHz, MeOD), guanidine: δ 158.8; carbonyl carbons: δ 176.1, 175.2, 174.9, 173.1.

Example 27

H₂N—CO—CH₂—(R)Cha—Pro—Nag×HOAc

Alkylation as in Example 4 using H—(R)Cha—Pro—Nag(Z) (See Example 20) and Cl—CH₂CONH₂, in the presence of a catalytic (10 mol %) amount of KI in the reaction, followed by deprotection procedure (a) gave the title compound.

$^1$H-NMR (500 MHz, D₂O): δ 1.02 (m, 2H), 1.12–1.34 (m, 3H), 1.46 (m, 1H), 1.61–2.13 (m, 9H) 1.99 (s, acetate), 2.34 (m, 1H), 3.25 (t, 2H), 3.33 (t, 2H), 3.60–3.82 (m, 4H), 4.22 (t, 1H), 4.41 (dd, 1H).

$^{13}$C-NMR (75 MHz, D₂O,): guanidine: δ 157.5; carbonyl carbons: δ 168.94, 169.40, 174.43.

Example 28

HOOC—CH₂—NH—CO—CH₂—(R)Cha—Pro—Nag×2 TFA

Alkylation as in Example 4 using H—(R)Cha—Pro—Nag(Z) (See Example 20) and Br—CH₂CONHCH₂COOBn (See Prep. of starting materials) followed by deprotection procedure (a) gave the title compound.

¹H-NMR (500 MHz, MeOD): δ 1.01 (m, 2H), 1.15–1.38 (m, 3H), 1.47 (m, 1H), 1.64–2.13 (m, 12H), 2.27 (m, 1H), 3.17–3.26 (m, 3H), 3.37 (m, 1H), 3.51 (m, 1H), 3.83 (m, 1H), 3.88 (s, 2H), 3.93–4.06 (m, 2H), 4.35–4.45 (m, 2H).

¹³C-NMR (75 MHz, MeOD): guanidine: δ 158.71; carbonyl carbons: δ 166.94, 168.35, 172.44, 174.17.

Example 29

(HOOC—CH₂)₂—(R)Cha—Pro—NagxHOAc (i) (EtOOC—CH₂)₂—(R)Cha—Pro—NH—(CH₂)₃—NH₂xHOAc

Alkylation as in Example 4 using H—(R)Cha—Pro—NH—(CH₂)₃—N₃ (See Example 22) and Br—CH₂COOEt (10 eq. was used to accomplish the dialkylation) followed by deprotection procedure (a) gave the title compond.

(ii) (EtOOC—CH₂)₂—(R)Cha—Pro—NagxHOAc

The same procedure as described in Example 19 (iii) for Z—(R)Cha—Pro—Nag was used to accomplish the guanidation of the amine above. Purification of the compound was made with RPLC (CH₃CN/NH₄OAc (0.1M), 4:6)

(iii) (HOOC—CH₂)₂—(R)Cha—Pro—NagxHOAc

The hydrolysis of the ester groups was made according to deprotection procedure (e) using a double amount of NaOH. The final compond was obtained pure after RPLC (CH₃CN/NH₄OAc (0.1M), 2:8), evaporation of the solvent and freeze drying (H₂O).

¹H-NMR (300 MHz, D₂O): δ 0.92–1.49 (m, 6H), 1.60–2.54 (m, 10H) 2.05 (s, acetate), 3.25–3.50 (m, 4H), 3.65–4.03 (m, 6H; thereof 3.95 (s, 4H)), 4.49 (m, 1H), 4.71 (m, 1H; partly hidden by the H-O-D peak).

¹³C-NMR (75 MHz, D₂O): guanidine: δ 157.64; carbonyl carbons: δ 168.62, 171.39, 174.30.

Example 30

HOOC—CH₂—(Me)(R)Cha—Pro—Nagx2 TFA (i) Me—(R)Cha—Pro—Nag(Z)

Prepared from Boc—(Me)(R)Cha—Pro—OSu and Boc—Nag(Z) in the same way as described for H—(R)Cha—Pro—Agm(Z) in Example 3.

(ii) HOOC—CH₂—(Me)(R)Cha—Pro—Nagx2 TFA

Alkylation as in Example 4 using Me—(R)Cha—Pro—Nag(Z) and Br—CH₂COOBn followed by deprotection procedure (b) gave the title compound.

¹H-NMR (500 MHz, D₂O): δ 0.8–1.06 (m, 2H), 1.08–1.27 (m, 4H), 1.55–2.10 (m, 12H), 2.30 (m, 1H), 3.04 (s, 3H), 3.14–3.33 (m, 4H), 3.63 (m, 1H), 3.81 (m, 1H), 4.13 (apparent bs, 2H), 4.38 (br.dd, 1H), 4.56 (bt, 1H).

¹³C-NMR (125.76 MHz, D₂O): guanidine: 157.40; carbonyl carbons: δ 174.05, 168.83, 167.44.

Example 31

HOOC—CH₂—("Bu)(R)Cha—Pro—Nagx2 TFA

Alkylation as in Example 4 using "Bu-(R)Cha—Pro—Nag(Z)(See Example 20) and Br—CH₂COOBn followed by deprotection procedure (a) gave the title compound.

¹H-NMR (500 MHz, D₂O): δ 0.78–0.88 (m, 3H), 0.88–1.02 (m, 2H), 1.02–1.23 (m, 4H), 1.23–1.38 (m, 2H), 1.45–1.84 (m, 11H), 1.84–2.10 (m, 3H), 2.24 (m, 1H), 3.05–3.18 (m, 3H), 3.18–3.38 (m, 3H), 3.57 (m, 1H), 3.77 (m, 1H), 4.05–4.25 (m, 2H), 4.32 (m, 1H), 4.50 (m, 1H).

¹³C-NMR (125 MHz, D₂O): guanidine: δ 159.17; carbonyl carbons: δ 175.66, 171.13, 169.31.

Example 32

HOOC—(R,S)CH(Me)—(R)Cha—Pro—NagxHOAC

Alkylation as in Example 4 using H—(R)Cha—Pro—Nag(Z) (See Example 20) and Br—CH(Me)COOBn followed by deprotection procedure (a) gave the title compound as a mixture of two diastereomers.

Example 33

HOOC—(RorS)CH(Me)—(R)Cha—Pro—Nag/axHOAc

Obtained by separating the diastereomers formed in Example 32 using RPLC (CH₃CN/NH₄OAc (0.1M), 1/4) followed by evaporation of the solvent. This diastereomer came out first of the two from the column.

¹H-NMR (300 MHz, D₂O, 2 rotamers ca: 9:1 ratio): δ 0.78 (m, minor rotamer), 1.07 (m, 2H), 1.17–1.42 (m, 3H), 1.48–1.64 (m, 4H; thereof 1.56 (d, 3H)), 1.64–1.95 (m, 9H), 1.95–2.20 (m, 3H) 2.00 (s, acetate), 2.37 (m, 1H), 3.28 (t, 2H), 3.38 (t, 2H), 3.53 (m, minor rotamer), 3.63 (m, 2H), 3.77 (m, 1H), 4.24 (d, minor rotamer), 4.35–4.50 (m, 2H), 4.60 (d, minor rotamer).

Example 34

HOOC—(RorS)CH(Me)—(R)Cha—Pro—Nag/bxHOAc

The title compound was obtained by using the same procedure as described in Example 33 on the compound formed in Example 32. This diastereomer came out after the first one from the column.

¹H-NMR (300 MHz, D₂O, 2 rotamers ca: 9:1 ratio): δ 0.95 (m, minor rotamer), 1.12 (m, 2H), 1.22–1.40 (m, 3H), 1.40–1.67 (m, 4H; thereof 1.60 (d, 3H)), 1.67–2.00 (m, 9H), 2.00–2.25 (m, 3H) 2.03 (s, acetate), 2.40 (m, 1H), 3.25–3.48 (m, 4H), 3.66–3.84 (m, 2H), 3.93 (m, 1H), 4.38 (m, 1H), 4.50 (m, 1H), 4.93 (m, minor rotamer).

¹³C-NMR (75.5 MHz, D₂O): δ 157.42; carbonyl carbons: δ 168.05, 171.99, 174.04.

Example 35

EtOOC—(R,S)CH(Me)—(R)Cha—Pro—Nagx2 TFA

Prepared in the same way as described for Example 22 using EtOOC—CH(Me)—Br instead of Br—CH₂—COOEt in the alkylation.

¹H-NMR (500 MHz, MeOD, 2 diastereomers ca: 2.5:1 ratio and 4 rotamers): δ 0.88–2.43 (m, 25H), 3.1–4.55 (m, 11H).

¹³C-NMR (75 MHz, MeOD): guanidine: δ 158.65; carbonyl carbons: δ 174.33, 170.66, 168.20.

Example 36

HOOC—(RorS)CH(nPr)—(R)Cha—Pro—Nag/axHOAc

Alkylation as in Example 4 using H—(R)Cha—Pro—Nag(Z) (See Example 20) and Br—CH("Pr) COOEt and deprotection procedure (e) followed by deprotection procedure (b) gave HOOC—(R,S)CH("Pr)—(R)Cha—Pro—Agm. The title compound was obtained by separating the diastereomers (this diastereomer came out first of the two from the column) by RPLC (CH$_3$CN/NH$_4$OAc (0.1M), 1/4) and freeze drying (H$_2$O) after evaportion of the solvent.

$^1$H-NMR (500 MHz, MeOD): δ 0.85 –1.05 (m, 5H; thereof 0.95 (t, 3H)), 1.1–2.05 (m, 20H) 1.95 (s, acetate), 2.18 (m, 1H), 3.15–3.3 (m, 4H), 3.35 (m, 1H), 3.46 (m, 1H), 3.85 (m, 1H), 4.04 (m, 1H), 4.38 (dd, 1H).

$^{13}$C-NMR (125 MHz, MeOD): guanidine: δ 158.73; carbonyl carbons: δ 171.63, 174.43 and 176.78.

Example 37

HOOC—(R)CH(CH$_2$—OH)—(R)Cha—Pro—Nag×2 TFA

Alkylation as in Example 4 using H—(R)Cha—Pro—Nag(Z) (See Example 20) and Br—(S)CH(CH$_2$—OBn)—COOBn followed by deprotection procedure (a) gave the title compound.

$^1$H-NMR (300 MHz, D$_2$O): δ 0.75–1.56 (m, 7H), 1.56–2.30 (m, 11H), 2.40 (m, 1H), 3.15–3.55 (m, 4H), 3.55–4.60 (m, 7H).

Example 38

HOOC—(R,S)CH(Ph)—(R)Cha—Pro—Nag×2 TFA

Alkylation as in Example 4 using H—(R)Cha—Pro—Nag(Z) (See Example 20) and Br—CH(Ph)COO$^t$Bu and deprotection procedure (a) followed by (f) gave the title compound as a mixture of two diastereomers.

$^1$H-NMR (300 MHz, MeOD): δ 0.8–1.1 (m, 2H), 1.1–2.18 (m, 16H), 2.26 (m, 1H), 3.04–3.35 (m, 5H), 3.45 (m, 1H), 3.7 (m, 1H), 4.35 (m, 1H), 4.85 (s, 1H, one isomer), 5.05 (s, 1H, the other isomer), 7.4–7.6 (m, 5H), 7.75 (bt, 1H).

$^{13}$C-NMR (75 MHz, D$_2$O): guanidine: δ 158.68; carbonyl carbons: δ 174.39, 174.15 and 170.5, 170.06 and 168.32, 167.78.

Example 39

HOOC—(S)CH(CH$_2$CH$_2$Ph)—(R)Cha—Pro—Nag× HOAc

Alkylation as in Example 21 using H—(R)Cha—Pro—Nag(Z)(See Example 20) and TfO—(R)CH(CH$_2$CH$_2$Ph)—COOEt and deprotection procedure (e) followed by (a) gave the title compound.

$^1$H-NMR (300 MHz, MeOD): δ 0.77–1.05 (m, 2H), 1.05–1.35 (m, 5H), 1.35–2.16 (m, 14H) 1.88 (s, acetate), 2.71 (t, 2H), 3.07–3.53 (m, 7H), 3.73 (m, 1H), 4.32 (m, 1H), 7.03–7.25 (m, 5H).

$^{13}$C-NMR (75 MHz, MeOD): guanidine: δ 158.71; carbonyl carbons: δ 174.15, 177.31, 182.61.

Example 40

HOOC—(R)CH(CH$_2$CH$_2$Ph)—(R)Cha—Pro—Nag× HOAc

Alkylation as in Example 4 using H—(R)Cha—Pro—Nag(Z) (See Example 20) and Br—CH(CH$_2$CH$_2$Ph)COOEt followed by deprotection procedure (a) and (e) gave HOOC—(R,S)CH(CH$_2$—CH$_2$—Ph)—(R)Cha—Pro—Nag. The title compound was obtained by separating the two diastereomers with RPLC (CH$_3$CN/NH4OAc (0.1M), 2/3) and freeze drying (H$_2$O) after evaportion of the solvent.

$^1$H-NMR (300 MHz, MeOD): δ 0.97 (m, 2H), 1.10–1.41 (m, 3H), 1.43–2.30 (m, 16H) 1.96 (s, acetate), 2.70 (m, 2H), 3.06–3.26 (m, 3H), 3.28–3.66 (m, 3H), 3.84 (m, 1H), 4.14 (bt, 1H), 4.39 (dd, 1H), 7.11–7.28 (m, 5H).

$^{13}$C-NMR (75 MHz, MeOD): guanidine: δ 158.66

Example 41

HOOC—CH$_2$—CH$_2$—(R)Cha—Pro—Nag×HOAc (i) EtOOC—CH$_2$—CH$_2$—(R)Cha—Pro—NH—(CH$_2$)$_3$-NH$_2$

Alkylation as described in Example 15 using H—(R)Cha—Pro—NH—(CH$_2$)$_3$—N$_3$ instead of H—(R)Cha—Pro—Agm(Z) followed by deprotection procedure (a) gave the title compound.

(ii) Et—OOC—CH$_2$—CH$_2$—(R)Cha—Pro—Nag× HOAc

Guanidation of the amine above in the same way as described in Example 19 for Z—(R)Cha—Pro—Nag gave the title compound (ii).

(iii) HOOC—CH$_2$—CH$_2$—(R)Cha—Pro—Nag×HOAc

Prepared by using the deprotection procedure (e) on the product (ii) above.

$^1$H-NMR (500 MHz, D$_2$O): δ 1.12 (m, 2H), 1.22–1.48 (m, 3H), 1.54 (bs, 1H), 1.70–2.37 (m, 12H) 2.14 (s, acetate), 2.53 (m, 1H), 2.70 (bs, 2H), 3.15 (t, 1H), 3.25–3.55 (m, 5H), 3.75 (m, 1H), 3.93 (m, 1H), 4.43 (t, 1H), 4.52 (m, 1H).

Example 42

EtOOC—CH$_2$—CH$_2$—(R)Cha-Pro-Nag x HOAc

Prepared according to Example 41 (ii).

$^1$H-NMR (500 MHz, D$_2$O): δ 0.97 (m, 2H), 1.11–1.39 (m, 7H; thereof 1.30 (t,3H)), 1.50 (t, 2H), 1.62–1.76 (m, 5H), 1.76–2.14 (m, 5H) 1.93 (s, acetate), 2.29 (m, 1H), 2.62 (t, 2H), 2.77–2.94 (m, 2H), 3.23 (t, 2H), 3.32 (t, 2H), 3.60–3.87 (m, 3H), 4.20 (q, 2H), 4.36 (dd, 1H).

$^{13}$C-NMR (125 MHz, D$_2$O): guanidine: δ 157.39; carbonyl carbons: δ 182.05, 175.13, 175.02.

Example 43

HOOC—(CH$_2$)$_3$—(R)Cha-Pro-Nag x 2 HOAc (i) Et-OOC—CH=CH—CH$_2$—(R)Cha-Pro-Nag(Z)

H-(R)Cha-Pro-Nag(Z) (See Example 20) (1 eq) and ethyl 3-bromocrotonate (1.1 eq) were dissolved in acetonitrile (15 ml/mmol). Potassium carbonate was added and the reaction mixture stirred at room temperature for 2 h. After filtration and evaporation of the solvent, the crude product was purified by flash chromatography (CH$_2$Cl$_2$/MeOH). Finally the solvent was evaporated and product dried in vacuo.

$^1$H-NMR (500 MHz, CDCl$_3$): δ 0.73–1.0 (m, 2H), 1.0–1.4 (m, 8H; thereof 1.33 (t, 3H)), 1.43–2.15 (m, 12H), 2.96 (bs, 1H), 3.12 (dd, 1H), 3.16–3.48 (m, 6H), 3.56 (m, 1H), 4.15 (q, 2H), 4.35 (bs, 1H), 5.03 (s, 1H), 6.0 (d, 1H), 6.85 (dr, 1H), 7.05 (bs, 1H), 7.17–7.37 (m, 5H), 7.5 (bs, 1H).

(ii) EtOOC—(CH$_2$)$_3$—(R)Cha-Pro-Nag x 2 TFA

Prepared by using the deprotection procedure (a) on the product (i) above.

(iii) HOOC—(CH$_2$)$_3$—(R)Cha-Pro-Nag x 2 HOAc

Prepared by using the deprotection procedure (e) on the product (ii) above.

$^1$H-NMR (500 MHz, D$_2$O): δ 1.02 (bs, 2H), 1.08–1.32 (m, 3H), 1.42 (bs, 1H), 1.55–2.15 (m, 14H) 1.92 (s, acetate), 2.33 (bs, 3H), 3.00 (bs, 1H), 3.07 (bs, 1H), 3.18–3.40 (m, 4H), 3.62 (bs, 1H), 3.82 (bs, 1H), 4.33 (bs, 1H), 4.40 (bs, 1H).

$^{13}$C-NMR (125 MHz, D$_2$O): guanidine: δ 157.42; carbonyl carbons: δ 181.87, 174.34, 168.64.

Example 44

EtOOC—(CH$_2$)$_3$—(R)Cha-Pro-Nag x 2 TFA

Prepared according to Example 43 (ii).

$^1$H-NMR (300 MHz, MeOD/D$_2$O): δ 0.63–1.30 (m, 9H; thereof 1.02 (t, 3H)), 1.30–1.97 (m, 14H), 2.06 (bs, 1H), 2.28 (m, 2H), 2.72–3.20 (m, 6H), 3.36 (m, 1H), 3.60 (m, 1H), 3.94 (m, 2H), 4.06 (m, 1H), 4.17 (m, 1H).

$^{13}$C-NMR (75 MHz, MeOD/D$_2$O): guanidine: δ 158.10; carbonyl carbons: δ 175.40, 174.23, 168.54.

Example 45

HOOC-CO-(R)Cha-Pro-Nag x HOAc (i) EtOOC-CO-(R)Cha-Pro-Nag(Z)

H-(R)Cha-Pro-Nag(Z), 0.50 g (0.97 mmol) was dissolved in 0.54 ml triethyl amine and 8 ml of CH$_2$Cl$_2$. Ethyl oxalylchloride, 0.146 g (1.07 mmol) dissolved in 2 ml of CH$_2$Cl$_2$ was added while the temperature rose from 22°–28° C. and the reaction was stirred at room temperature for 2 h. The organic phase was washed twice with water, dried (Na$_2$SO$_4$) and flash chromathographed (EtOAc/EtOH(99%), 9/1) to give 92 mg (15 %) of the title compund.

(ii) HOOC-CO-(R)Cha-Pro-Nag x HOAc

Using the deprotection procedure (b) followed by (e) gave the title compound.

$^1$H-NMR (300 MHz, MeOD): δ 0.88–1.14 (m, 2H), 1.15–1.5 (m, 4H), 1.5–2.3 (m, 13H) 1.9 (s, acetate), 3.1–3.43 (m, 4H), 3.6 (m 1H), 4.05 (m, 1H), 4.43 (dd, 1H), 4.5 (m, 1H).

$^{13}$C-NMR (75 MHz, D$_2$O): guanidine: δ 157.57; carbonyl carbons: δ 165.94, 173.95, 174,85 and 181.22.

Example 46

MeOOC-CO-(R)Cha-Pro-Nag x HOAc (i) MeOOC-CO-(R)Cha-Pro-Nag(Z)

The methyl ester was obtained by transesterification of EtOOC-CO-(R)Cha-Pro-Nag(Z) (See Example 45) on the column during flash chromatography when EtOAc/MeOH(9:1) was used as eluent. Yield 55%.

(ii) MeOOC-CO-(R)Cha-Pro-Nag x HOAc

Prepared by using the deprotection procedure (b) on the product (i) above.

$^1$H-NMR (300 MHz, MeOD): δ 0.9–1.1 (m, 2H), 1.1–2.3 (m, 17H) 1.9 (s, acetate), 3.12–3.4 (m, 4H), 3.52–3.67 (m, 2H), 3.9 (s, 3H), 4.35 (m, 1H), 4.65 (m, 1H).

$^{13}$C-NMR (75 MHz, D$_2$O): guanidine: δ 157.52; carbonyl carbons: δ 159.11, 161.20 173.17 and 174.90.

Example 47

(R,S)Bla-(R)Cha-Pro-Nag x 2 TFA

Alkylation as in Example 4 using H-(R)Cha-Pro-Nag(Z) (See Example 20) and α-bromo butyrolacton followed by deprotection procedure (a) gave the title compound as a mixture of two diastereomers.

$^1$H-NMR (300 MHz, D$_2$O, mixture of diastreomers): δ 1.0–1.43 (m, 5H), 1.45–1.60 (br.s, 1H), 1.64–2.28 (m, 12H), 2.31–2.50 (m, 1H), 2.80–2.98 (m, 1H), 3.23–3.46 (m, 4H), 3.66–3.79 (m, 1H), 3.82–3.96 (m, 1H), 4.33–5.08 (m, 5H, partially hidden by the H-O-D signal).

Example 48

HOOC-(R,S)CH(CH$_2$COOH)-(R)Cha-Pro-Nag x HOAc (i) BnOOC-(R,S)CH (CH$_2$COOBn)-(R)Cha-Pro-Nag(Z)

H-(R)Cha-Pro-Nag(Z) (See Example 20), 0.21 g (0.42 mmol), and 0.12 g (0.42 mmol) of dibenzyl maleate were dissolved in 10 ml of CH$_3$CN. The mixture was refluxed over night, evaporated and flash chromatographed (CH$_2$Cl$_2$/MeOH, 94/6). Evaporation of the solvent gave the desired compound in 22% yield.

(ii) HOOC-(R,S)CH(CH$_2$COOH)-(R)Cha-Pro-Nag x HOAc

Prepared by using the deprotection procedure (a) on the product (i) above.

$^1$H-NMR (500 MHz, MeOD): δ 0.9–2.4 (m, 19H), 2.00 (s, acetate) 2.7–3.0 (m, 2H), 3.1–3.6 (m, 5H), 3.75–3.9 (m, 2H), 4.2–4.5 (m, 2H).

Example 49

MeOOC-(R,S)CH(CH$_2$COOMe)-(R)Cha-Pro-Nag x HOAc (i) MeOOC-(R,S)CH(CH$_2$COOMe)-(R)Cha-Pro-Nag(Z)

H-(R)Cha-Pro-Nag(Z) (See Example 20), 0.21 g (0.42 mmol), and 0.24 g (1.7 mmol) of dimethyl maleate were dissolved in 15 ml of MeOH. The mixture was refluxed over night, evaporated and flash chromatographed (CH$_2$Cl$_2$/MeOH, 9/1). Evaporation of the solvent gave the desired compound in 45% yield.

(ii) MeOOC-(R,S)CH(CH$_2$COOMe)-(R)Cha-Pro-Nag x HOAc

Prepared by using the deprotection procedure (c) on the product (i) above.

$^1$H-NMR (500 MHz, MeOD): δ 0.85–1.1 (m, 2H), 1.15–2.3 (m, 17H), 1.91 (s, acetate), 2.6–2.8 (m, 2H), 3.1–3.5 (m, 5H), 3.5–3.8 (m, 10H; thereof 4 singlets 3.66, 3.68, 3.71, 3.73), 4.29 (m, 1H).

Example 50

HOOC-Ph-4—CH$_2$—(R)Cha-Pro-Nag x 2 TFA (i) $^t$BuOOC-Ph-4—CH$_2$—(R) Cha-Pro-NH- (CH$_2$)$_3$-N$_3$

H-(R)Cha-pro-NH-(CH$_2$)$_3$-N$_3$ (See Example 22), 0.39 g (1.1 mmol) and 0.33 g (1.2 mmol) of tertiarybutyl p-bromomethylbenzoate were dissolved in 10 ml of CH$_3$CN and 0.19 g (2.4 mmol) of K$_2$CO$_3$ was added. The mixture was refluxed over night and evaporated. The crude product was flash chromatographed (CH$_2$Cl$_2$/MeOH, 92:8) to give 0.50 g (84%) of the title compond.

(ii) $^t$BuOOC-Ph-4—CH$_2$—(R)Cha-Pro-NH-(CH$_2$)$_3$-NH$_2$

To a solution of 0.60 g (1.8 mmol) of bis-phenylthio stannane, 0.20 g (1.8 mmol) of thiophenol and 0.18 g (1.8 mmol) of triethyl amine in 50 ml of CH$_2$Cl$_2$ at 0° C. was added 0.50 g (0.92 mmol) of $^t$BuOOC-Ph-4—CH$_2$—(R)Cha-pro-NH—(CH$_2$)$_3$—N$_3$. The mixture was stirred at 0° C. for 30 min. and at room temperature for 4 h. It was then diluted with CH$_2$Cl$_2$ and washed with aqueous sodium bicarbonate and subsequently 3 times with 2% H$_2$O$_2$. The organic layer was extracted with dilute HCl. The combined acidic water phase was washed with EtOAc and subsequently made alkaline with NaOH(aq). The aqueous layer was extracted twice with ethyl acetate. The combined organic layer was dried ($Na_2SO_4$) and evaporated. Flash chromatography ($CH_2Cl_2$MeOH($NH_3$-saturated), 8:2) gave 0.12 g (26%) of the title compound.

(iii) HOOC-Ph-4—$CH_2$—(R)Cha-Pro-Nag x 2 TFA

Guanidation of the amine above in the same way as described in Example 19 for Z-(R)Cha-Pro-Nag followed by deprotection procedure (f) gave the title compound.

$^1$H-NMR (500 MHz, MeOD): δ 0.9–1.5 (m, 7H), 1.4–1.9 (m, 9H), 1.95–2.1 (m, 2H), 2.16 (m, 1H), 2.32 (m, 1H), 3.2–3.3 (m, 3H), 3.41 (pentet, 1H), 3.53 (m, 1H), 3.77 (m, 1H), 4.2–4.3 (m, 3H), 4.42 (dd, 1H), 7,15 (d, 2H), 8.10 (d, 2H).

$^{13}$C-NMR (125 MHz, MeOD), guanidine: δ 160.8; carbonyl carbons: δ174.3, 168.9, 168.2.

Example 51

$(HO)_2P(O)$—$CH_2$—(R)Cha-Pro-Nag x HOAc $(EtO)_2PO$—$CH_2$—(R)Cha-Pro-Nag(Z) (See Example 53), 60 mg (92 mmol), was dissolved in 3 ml of $CH_3CN$. Trimethylsilyl bromide, 0.15 ml, was added and the mixture was left at room temperature for 21 h. After evaporation and NMR analysis it was found that some ester remained. The crude material was again dissolved in 3 ml of $CH_3CN$ and 0.15 ml of trimethylsilyl bromide was added. After 5 h the mixture was evaporated and purified with RPLC ($CH_3CN$/$NH_4OAc$ (0.1M), 30:70) to give the final compound after filtration, evaporation and freeze drying in 8% yield.

$^1$H-NMR (500 MHz, MeOD): δ 0.8–1.1 (m, 2H), 1.15–1.4 (m, 4H), 1.5–1.9 (m, 10H), 1.9–2.1 (m, 4H) 1.96 (s, acetate), 2.20 (m, 1H), 2.95 (m, 1H), 3.0–3.2 (m, 3H), 3.4–3.5 (m, 2H), 4.09 (m, 1H), 4.39 (bd, 1H), 4.59 (m, 1H).

$^{13}$C-NMR (125 MHz, MeOD): guanidine: δ 158.6; carbonyl carbons: δ 174.2, 170.6

Example 52

EtO(HO)P(O)—$CH_2$—(R)Cha-Pro-Nag x 2 HOAc (i) (EtO) (HO) PO—$CH_2$—(R)Cha-Pro-Nag(Z).

$(EtO)_2PO$—$CH_2$—(R)Cha-Pro-Nag(Z) (See Example 53), 50 mg (77 mmol) was dissolved in 2 ml of EtOH and 2 ml 2M NaOH. The mixture was stirred over night and evaporated. The crude material was purified with RPLC ($CH_3CN$/$NH_4OAc$ (0.1M), 30:70) to give the title compound after filtration and evaporation of the solvent.

(ii) (EtO) (HO)PO—$CH_2$—(R)Cha-Pro-Nag x 2 HOAc

Prepared by using deprotection procedure (c) on the product (i) above.

$^1$H-NMR (500 MHz, MeOD): δ 0.9–1.1 (m, 2H), 1.15–1.35 (m, 6H; thereof 1.28 (t, 3H)), 1.35–1.5 (m, 2H), 1.5–1.6 (m, 1H), 1.65–1.8 (m, 6H), 1.9–2.1 (m, 3H) 1.95 (s, acetate), 2.19 (m, 1H), 2.8–3.0 (m, 2H), 3.1–3.25 (m, 2H), 3.27 (m, 1H), 3.36 (m, 1H), 3.48 (m, 1H), 3.9–4.05 (m, 4H), 4.36 (bd, 1H).

$^{13}$C-NMR (125 MHz, MeOD): guanidine: δ 158.6; carbonyl carbons: δ 175.0, 174.7

Example 53

$(EtO)_2P(O)$—$CH_2$—(R)Cha-Pro-Nag x HOAc (i) $(EtO)_2PO$—$CH_2$—(R)Cha-Pro-Nag(Z).

H-(R)Cha-Pro-Nag(Z) (See Example 20), 0.2 g (0.40 mmol), was dissolved in 5 ml of THF and 0.11 g (0.80 mmol) of potassium carbonate and 0.12 g (0.40 mmol) diethyl triflylmethylphosphonate were added. The mixture was stirred at room temperature for 2 h. The reaction was worked up with water and extraction of the aqueous layer three times with EtOAc. The combined organic layer was dried ($Na_2SO_4$) and evaporated to yield 0.14 g (53%) of the title compound.

(ii) $(EtO)_2PO$—$CH_2$—(R)Cha-Pro-Nag x HOAc

Prepared by using the deprotection procedure (c)on the product (i) above.

$^1$H-NMR (500 MHz, MeOD): δ 0.85–1.05 (m, 2H), 1.15–1.3 (m, 5H), 1.34 (t, 6H), 1.5–1.85 (m, 8H), 1.9–2.05 (m, 3H) 1.91 (s, acetate), 2.10 (m, 1H), 2.22 (m, 1H), 2.90 (dd, 1H), 3.05 (dd, 1H), 3.1–3.3 (m, 3H), 3.42 (m, 1H), 3.53 (m, 1H), 3.71 (dd, 1H), 3.82 (m, 1H), 4.1–4.2 (m, 4H), 4.28 (dd, 1H).

$^{13}$C-NMR (125 MHz, MeOD), guanidine: δ 158.7; carbonyl carbons: δ 176.1, 175.1.

Example 54

HOOC—$CH_2$—(R)Cha-Pro-Mag x HOAc (i) H-(R) Cha-Pro-NH—$(CH_2)_2$—NH(Z)

Prepared from Boc-(R)Cha-Pro-OSu and $H_2N$—$(CH_2)_2$—NH(Z) in the same way as described for H-(R)Cha-Pro-Agm(Z) in Example 3.

(ii) EtOOC—$CH_2$—(R)Cha-Pro-NH—$(CH_2)_2$—$NH_2$ x HOAc

Alkylation as in Example 4 followed by deprotection procedure (a) gave the title compound.

(iii) HOOC—$CH_2$—(R)Cha-Pro-Mag x HOAc

Guanidation of the amine above in the same way as described in Example 19 for Z-(R)Cha-Pro-Nag followed by deprotection procedure (e) gave the title compound after purification by RPLC ($CH_3CN$/$NH_4OAc$ (0.1M), ¼) and freeze drying($H_2O$).

$^1$H-NMR (300 MHz, $D_2O$): δ 0.90–1.18 (m, 2H), 1.19–1.43 (m, 3H), 1.52 (m, 1H), 1.63–2.20 (m, 10H) 2.06 (s, acetate), 2.31–2.47 (m, 1H), 3.44 (m, 2H), 3.50 (m, 2H), 3.60–3.75 (m, 3H), 3.85 (m, 1H), 4.46–4.54 (m, 2H).

$^{13}$C-NMR (75 MHz, $D_2O$): guanidine: δ 157.82; carbonyl carbons: δ 168.80, 171.41, 174.81.

Example 55

H-(R,S)Pro(3-Ph)-Pro-Agm x 2 TFA

Prepared from Boc-(R,S)Pro(3-Ph)-Pro-OSu (See Prep. of starting materials) in the same way as described for H-(R)Cha-Pro-Agm(Z) in Example 3 followed by deprotection procedure (b).

$^1$H-NMR (500 MHz, $D_2O$, mixture of two diastereomers with unknown relative stereochemistry): δ 1.0–1.8 (m, 7H), 2.0–2.5 (m, 3H), 2.8–4.3 (m, 10H), 4.56 (d, 1H, major), 4.90 (d, 1H, major), 7.2–7.5 (m, 5H).

$^{13}$C-NMR (125.76 MHz, $D_2O$): guanidine: δ 157.36 (minor and major); carbonyl carbons: δ 174.1 (major), 174.0 (minor), 167.8 (major), 167.0 (minor).

Example 56

H-(R,S)Pro(3-(trans)Ch)-Pro-Agm x 2 TFA

Prepared from Boc-(R,S)Pro(3-(trans)Ch)-Pro-OSu (See

Prep. of starting materials) in the same way as described for H-(R)Cha-Pro-Agm(Z) in Example 3 followed by deprotection procedure (b).

$^1$H-NMR (500 MHz, D$_2$O, mixture of two diastereomers, ratio, 1.8/1): δ 0.95–1.32 (m 5H), 1.35–1.46 (m, 1H), 1.50–1.92 (m, 10H), 1.93–2.15 (m, 4H), 2.23–2.43 (m, 2H), 3.15–3.30 (m, 4H), 3.35–3.50 (m, 2H), 3.57–3.68 (m, 1H), 3.74–3.82 (m, 1H), 4.34–4.41 (m, 1H), 4.51 (d, 1H, minor), 4.48 (d, 1H, major).

$^{13}$C-NMR (125.76 MHz, D$_2$O): guanidine: δ 157.36 (minor and major), carbonyl carbons: δ 174.34 (major), 174.07 (minor), 168.94 (minor and major).

Example 57

HOOC—CH$_2$—(R,S)Pro(3-(trans)Ph)-Pro-Agm x 2 TFA (i) H-(R,S) Pro(3-(trans) Ph)-Pro-Agra(Z)

Prepared from Boc-(R,S)Pro(3-(trans)Ph)-Pro-OSu (See Prep. of starting materials) in the same way as described for H-(R)Cha-Pro-Agm(Z) in Example 3.

(ii) HOOC—CH$_2$—(R,S)Pro(3-(trans)Ph)-Pro-Agm x 2 TFA

Alkylation as in Example 4 using Br—CH$_2$COOBn followed by deprotection procedure (b) gave the title compound as a mixture of two diastereomers.

$^1$H-NMR (500 MHz, MeOD, mixture of two diastereomers, ratio ca: 1.1/1): δ 1.40–1.80 (m, 6H), 1.85–2.05 (m, 1H), 2.10–2.30 (m, 1H), 2.50–2.65 (m, 2H), 3.10–3.40 (m, 6H), 3.50–3.70 (m, 2H), 3.9–4.40 (m, 4H), 4.63 (d, 1H, major), 4.67 (d, 1H, minor), 7.30–7.60 (m, 5H).

$^{13}$C-NMR (125.76 MHz, D$_2$O): guanidine: δ 157.52 (both isomers); carbonyl carbons: δ 173.87, 173.73, 169.12, 168.94, 167.21, 167.00.

Example 58

HOOC—CH$_2$—(R,S)Pro(3-(trans)Ph)-Pro-Nag x 2 TFA (i) H-(R,S)Pro(3-(trans)Ph)-Pro-Nag (Z)

Prepared from Boc-(R,S)Pro(3-(trans)Ph)-Pro-OSu (See Prep. of starting materials) and Boc-Nag(Z) in the same way as described for H-(R)Cha-Pro-Agm(Z) in Example 3.

(ii) HOOC—CH$_2$—(R,S)Pro(3-(trans)Ph)-Pro-Nag x 2 TFA

Alkylation as in Example 4 using Br—CH$_2$COOBn followed by deprotection procedure (b) gave the title compound as a mixture of two diastereomers.

$^1$H-NMR (500 MHz, MeOD, mixture of two diastereomers, ratio ca: 1.5/1): δ 1.40–1.85 (m, 4H), 1.90–2.00 (m, 1H), 2.10–2.30 (m, 1H), 2.45–2.70 (m, 2H), 3.08–3.46 (m, 6H), 3.57–3.70 (m, 2H), 3.90–4.0 (m, 1H), 4.32–4.40 (m, 1H), 4.04 and 4.29 (AB-quartet, 2H, major), 4.16 and 4.37 (AB-quartet, 2H, minor), 4.60 (d, 1H, major), 4.64 (d, 1H, minor), 7.3–7.6 (m, 5H).

$^{13}$C-NMR (125.76 MHz, D$_2$O): guanidine: δ 157.48 (both isomers); carbonyl carbons: δ 173.90, 173.71, 169.01, 168.94, 167.07 (both isomers).

Example 59

HOOC—CH$_2$—(R)Cha-Pic-Agm x 2 TFA (i) H-(R)Cha-Pic-Agm(Z)

Prepared from Boc-(R)Cha-Pic-OSu (See Prep. of starting materials) in the same way as described for H-(R)Cha-Pro-Agm(Z) in Example 3.

(ii) HOOC—CH$_2$—(R)Cha-Pic-Agmx 2 TFA

Alkylation as in Example 4 using Br—CH$_2$COOBn followed by deprotection procedure (a) gave the title compound.

$^1$H-NMR (300 MHz, MeOD): δ 1.02 (m,2H), 1.13–2.00 (m, 20H), 2.24 (bd, 1H), 3.12–3.45 (m, 5H), 3.71 (bd, 1H), 3.87 (s, 2H), 4.65 (bt, 1H), 5.06 (m, 1H).

$^{13}$C-NMR (75 MHz, D$_2$O): guanidine: δ 157.47; carbonyl carbons: δ 169.42, 170.03, 172.71.

Example 60

HOOC—CH$_2$—(Me)(R)Cha-(R,S)Pic-Agmx HOAc (i) Me-(R)Cha-(R,S)Pic-Agm(Z)

Prepared from Boc-(Me)(R)Cha-Pic-OSu in the same way as described for H-(R)Cha-Pro-Agm(Z) in Example 3.

(ii) HOOC—CH2—(Me)(R)Cha-(R,S)Pic-Agm x HOAc

Alkylation as in Example 4 using Br—CH$_2$COOBn followed by deprotection procedure (b) gave the title compound.

Comment: An epimerization of Pic occured somewhere during the synthesis.

The $^1$H-NMR spectrum is complex consisting of two diastereomers ca: 1:1 ratio and rotamers thereof.

$^1$H-NMR (500 MHz, MeOD): δ 0.75–2.15 (several m, 20H) 1.95 (bs, acetate), 2.2–2.7 (6H, two distinct sets of signals are observed in the ratio of ca: 1:1; thereof 2.35 and 2.55 (s, 3H)), 3.0–3.5 (m, 6H), 3.9–4.17 (m, 2H; thereof 4.14 (dd)), 4.4–4.5 (m, 1H), 4.97–5.15 (two bdd, 1H).

$^{13}$C-NMR (75MHz, D$_2$O): guanidine: δ 157.50; carbonyl carbons: δ 169.65, 170.01, 170.54, 172.67, 172.89.

Example 61

HOOC-(R,S)CH(Me)-(R)Cha-Pic-Agm x TFA

Alkylation as in Example 4 using H-(R)Cha-Pic-Agm(Z) (See Example 59) and Br—CH(Me)COOBn followed by deprotection procedure (a) gave the title compound as a mixture of two diastereomers.

Example 62

HOOC-(RorS)CH(Me)-(R)Cha-Pic-Agm/a x 2 TFA

Obtained by separating the diastereomers formed in Example 61 using RPLC (CH$_3$CN/NH$_4$OAc (0.1M), ⅓) followed by evaporation of the solvent and freeze-drying from H$_2$O/TFA. This diastereomer came out first of the two from the column.

$^1$H-NMR (300 MHz, D$_2$O, 2 rotamers ca: 5:1 ratio): δ 0.70 (m, minor rotamer), 0.75–1.0 (m, 2H), 1.0–1.28 (m, 3H) , 1.28–1.83 (m, 20H; thereof 1.57 (d, 3H)), 2.14 (bd, 1H), 2.92 (t, minor rotamer), 3.03–3.32 (m, 5H), 3.59 (bd, 1H), 3.85 (q, minor rotamer), 3.98 (q, 1H), 4.30–4.50 (m, minor rotamer), 4.54 (m, 1H), 4.95 (s, 1H).

$^{13}$C-NMR (75 MHz, D$_2$O): guanidine: δ 157.39; carbonyl carbons: δ 172.26 (2 carbons), 169.92.

Example 63

HOOC-(RorS)CH(Me)-(R)Cha-Pic-Agm/b x 2 TFA

The title compound was obtained by using the same procedure as described in Example 62 on the compound formed in Example 61. This diastereomer came out after the first one from the column.

¹H-NMR (500 MHz, D₂O, 2 rotamers ca: 5:1 ratio): δ 0.72 (m, minor rotamer), 0.82 (m, minor rotamer), 0.97 (m, 2H), 1.0–1.23 (m, 3H), 1.23–1.40 (m, 2H), 1.40–1.83 (m, 18H; thereof 1.63 (d, 3H)), 2.11 (d, 1H) , 2.17 (d, minor rotamer), 2.92 (t, minor rotamer), 3.05–3.25 (m, 4H), 3.29 (t, 1H), 3.74 (d, 1H), 4.02 (q, 1H), 4.34 (d, minor rotamer), 4.41 (dd, minor rotamer), 4.52 (t, 1H), 4.95 (s, 1H).

¹³C-NMR (125 MHz, D₂O): guanidine: δ 154.68; carbonyl carbons: δ 169.81, 169.60, 167.36.

Example 64

HOOC—CH2—CH2—(R)Cha-Pic-Agm x 2 TFA

Prepared from H-(R)Cha-Pic-Agm(Z) (See Example 59) in the same way as described for HOOC—CH₂—CH₂—(R)Cha-pro-Agm in Example 15 using 1.2 eq. of benzylacrylate instead of 1.1 eq.

¹H-NMR (500 MHz, D₂O, 2 rotamers ca: 4:1 ratio): δ 0.70–0.90 (m, minor rotamer), 0.90–1.0 (m, 2H), 1.05–1.25 (m, 3H), 1.30–1.45 (m, 2H), 1.45–1.85 (m, 15H), 2.1 (bd, 1H), 2.2 (bd, minor rotamer), 2.75 (t, 2H), 2.95 (t, minor rotamer),3.1–3.4 (m, 7H), 3.75 (bd, 1H), 4.55 (t, 1H), 4.95 (m, 1H).

¹³C-NMR (75 MHz, D₂O): guanidine: δ 157.48; carbonyl carbons: δ 170.10, 172.58, 174.75.

Example 65

H-(R)Cha-Pic-Nag x 2 TFA (i) Boc-(R)Cha-Pic-Nag(Z)

(ia) Prepared by starting from Boc-(R)Cha-Pic-OSu by using the same procedure as described for Boc-(R)Cha-Pro-Agm(Z) in Example 3.

(ib) Prepared by starting from Boc-(R)Cha-Pic-OH

Diphenylphosphoryl azide (0.432 ml, 2 mmol) was added to a stirred solution of Boc-(R)Cha-Pic-OH (765 mg, 2 mmol) in 5 ml DMF at –10 ° C. After 10 minutes H-Nag(Z) x 2 HCl (600 mg, 2.1 mmol, see Preparation of Starting Materials) in 5 ml DMF and triethylamine (615 mg, 4.4 mmol) was added. The reaction mixture was kept in an ice bath for 3 h and then at room temperature for 12 h after which it was poured out in water. Extraction of the water phase with EtOAc followed by drying (MgSO₄) of the organic phase and evaporation of the solvent in vacuo gave 1.18 g (96%) of the product as a mixture of diastereomers (Epimers in Pic) in a ratio of 97:3 (RS/RR).

(ic) Starting from Boc-(R)Cha-Pic-OH

EDC hydrochloride (4.2 g, 21.9 mmol) was added at –15° C. to a stirred solution of Boc-(R)Cha-Pic-OH (8 g, 20.9 mmol), DMAP (10.6 g, 88 mmol) and H-Nag-(Z) x 2 HCl (6.3 g, 19.5 mmol, see Preparation of Starting Materials) in acetonitrile. The reaction mixture was allowed to warmup to +15° C. during 16 h. The solvent was removed in vacuo an the residue was dissolved in ethyl acetate. Washing with water, 0.3M KHSO₄, 0.3M NaHCO₃, water and brine followed by drying (Na₂SO₄) and evaporation of the solvent gave 11.9 g (92.5%) of the product as a mixture of diastereomers (Epimers in Pic) in a ratio of 98/2 (RS/RR).

¹H-NMR (500 MHz, CDCl₃): δ 0.85–2.0 (m,29H; thereof 1.40 (bs, 9H)), 2.46 (bd, 1H), 3.1–3.4 (m, 5H), 3.92 (bd, 1H), 4.53 (bq, 1H), 5.10 (s, 2H), 5.22 (bs, 1H), 5.29 (bd, 1H), 6.7–7.2 (b, 3H), 7.25–7.45 (m, 5H).

¹³C-NMR (125 MHz, CDCl₃): guanidine δ 156.9; carbonyl carbons: δ 173.6, 170.3, 163.7, 161.7.

(ii) H-(R)Cha-Pic-Nag(Z)

Prepared in the same way as described for H-(R)Cha-Pro-Agm(Z) in Example 3, starting from Boc-(R)Cha-Pic-Nag(Z).

¹H-NMR (500 MHz, CDCl₃): δ 0.8–2.0 (m, 22H), 2.24 (bd, 1H), 3.1–3.4 (m, 5H), 3.72 (bd, 1H), 3.84 (bq, 1H), 5.05 (bd, 1H), 5.08 ( s, 2H), 7.3–7.5 (m, 5H).

(iii) H-(R)Cha-Pic-Nag x 2 TFA

Prepared by using the deprotection procedure (a) on the product (ii) above.

¹H-NMR (500 MHz, MeOD): δ 0.9–1.1 (m, 2H), 1.2–2.0 (m, 18H), 2.32 (bd, 1H), 3.20 (t, 2H), 3.30 (t, 2H), 3.36 (m, 1H), 3.69 (bd, 1H), 4.49 (dd, 1H), 5.05 (bd, 1H).

¹³C-NMR (125 MHz, MeOD): guanidine: δ 158.7; carbonyl carbons: δ 172.7, 171.4

Example 66

Me-(R)Cha-(R,S)Pic-Nag x 2 TFA (i) Me-(R)Cha-(R,S)Pic-Nag(Z)

Prepared in the same way as described for H-(R)Cha-Pro-Agm(Z) in Example 3 staring from Boc-(Me)(R)Cha-Pic-OSu and BocNag(Z). An epimerization of Pic occured during the synthesis and the product was obtained as mixture of two diastereomers.

(ii) Me-(R)Cha-(R,S)Pic-Nag x 2 TFA

Prepared by using deprotection procedure (b).

The ¹H-NMR spectrum is complex consisting of two diastereomers ca: 4:1 ratio and rotamers thereof.

¹H-NMR (500 MHz, MeOD): δ 0.8–1.08 (m, 2H), 1.15–2.4 (several m, 19H), 2.6–2.75 and 2.9–2.95 (several s, 3H) 3.1–3.6 (several m, 5H), 3.75–4.1 (several m, 1H) 4.4–4.7 (several m, 1H), 5.05–5.15 (two dd, 1H).

¹³C-NMR (125 MHz, D₂O): guanidine: δ 154.84; carbonyl carbons: δ 167.60 and 169.99.

Example 67

HOOC—CH₂—(R)Cha-Pic-Nag (i) BnOOC—CH₂—(R)Cha-pic-Nag(Z)

Alkylation as in Example 4 using H-(R)Cha-Pic-Nag(Z) (See Example 65) and Br—CH₂COOBn gave the title compund.

¹H-NMR (500 MHz, CDCl₃): δ 0.8–1.0 (m, 2H), 1.1–1.7 (m, 19H), 1.79 (bd, 1H), 2.3–2.5 (m, 2H; thereof 2.38 (bd, 1H)), 3.00 (bt, 1H), 3.1–3.4 (m, 5H; thereof 3.38 (d, 1H)) 3.58 (d, 1H), 3.6–3.7 (m, 2H), 5.06 (dd, 2H), 5.07 (s, 2H), 5.16 (bs, 1H), 6.7–7.1 (b, 1H), 7.15 (bs, 1H), 7.2–7.4 (m, 10H).

¹³C-NMR (125 MHz, CDCl₃) guanidine and carbonyl carbons: δ 176.0, 173.6, 170.8, 163.8, 161.7.

(iia) HOOC—CH₂—(R)Cha-pic-Nag x 2 HCl

Deprotection procedure (a) followed by purification with RPLC using CH₃CN/0.1M NH₄OAc, ⅓ as eluent, evaporation at 40°–500° C. and freeze drying gave the title compund as the acetate. Treatment with a 20-fold excess of hydrochloric acid, evaporation and renewed freeze drying gave the bis-hydrochloride of the desired compound.

¹H-NMR (500 MHz, D₂O, mixture of two rotamers): δ 0.7–2.0 (m, 20H), 2.17 (bd, 1H), 2.95 (t, minor rotamer), 3.17 (t, 2H), 3.25–3.35 (m, 3H), 3.72 (bd, 1H), 3.86 (dd, minor rotamer), 3.90 (s, 2H), 4.72 (t, 1H), 4.99 (bs, 1H).

¹³C-NMR (75 MHz, D₂O); guanidine δ 157.4; carbonyl carbons δ 169.9, 170.2, 173.0.

(iib) HOOC—CH₂—(R)Cha-pic-Nag x 2 HBr

BnOOC—CH₂—(R)Cha-Pic-Nag(Z) was dissolved in ⁱPr-OH/H₂O (95/5) and hydrogenated over 5% Pd/C at atmospheric pressure in the presence of HBr (2.2 eq.). The catalyst was filtered off and the solvent evaporated to give a yellow oil (Alternatively, the acid can be added after hydrogenation and filtration). Crystallisation from ⁱPr-OH (or EtOH)/EtOAc (1/1) gave the title compound as a white crystalline powder.

¹H-NMR (500 MHz, D₂O, mixture of two rotamers): δ 1.15–2.0 (m, 20H), 2.30 (bd, 1H), 3.30 (m, 2H), 3.40–3.50 (m, 3H), 3.85–3.90 (m, 1H), 3,95 (apparent s, 2H), 4.75–4.85 (m, 1H, partially hidden by the H-O-D line), 5.10 (bs, 1H).

¹³C-NMR (125 MHz, D₂O): guanidine: δ 157.6; carbonyl carbons: δ 169.7, 170.2, 173.0.

Example 68

MeOOC—CH₂—(R)Cha-Pic-Nag x 2 TFA

The methyl ester MeOOC—CH₂—(R)Cha-Pic-Nag(Z) was obtained by trans esterification of ⁱPrOOC—CH₂—(R)Cha-Pic-Nag(Z) (See Example 69) on the column during flash chromatography when CH₂Cl₂/MeOH was used as eluent. The title compound was obtained by the deprotection procedure (a).

¹H-NMR (500 MHz, MeOD): δ 0.95–1.15 (m, 2H), 1.2–1.6 (m, 6H), 1.65–2.0 (m, 13H), 2.25 (bd, 1H), 3.21 (t, 2H), 3.30 (t, 2H), 3.37 (m, 1H), 3.71 (m, 1H), 3.83 (s, 3H), 3.97 (dd, 2H), 4.67 (bt, 1H), 5.05 (bs, 1H).

¹³C-NMR (125 MHz, MeOD), guanidine: δ 158.0; carbonyl carbons: δ 173.0, 171.1, 168.3.

Example 69

ⁱPrOOC—CH₂—(R)Cha-Pic-Nag x 2 TFA

Alkylation as described in Example 4 using H-(R)Cha-Pic-Nag(Z) (See Example 65) and Br—CH₂—COOⁱPr followed by deprotection procedure (a) gave the title compound.

¹H-NMR (500 MHz, MeOD): δ 0.95–1.1 (m, 2H), 1.15–1.6 (m, 12H; thereof 1.25 (d, 3H), 1.28 (d, 3H)), 1.65–1.95 (m, 12H), 2.28 (bd, 1H), 3.21 (t, 2H), 3.30 (t,2H), 3.36 (m, 1H), 3.93 (dd, 2H), 4.67 (t, 1H), 5.04 (bs, 1H), 5.11 (pentet, 1H).

¹³C-NMR (125 MHz, MeOD), guanidine: δ 157.9; carbonyl carbons: δ 173.1, 171.0, 168.3.

Example 70

HOOC—CH₂—(Me)(R)Cha-(RorS)Pic-Nag/b x 2 TFA

Alkylation as described in Example 4 using Me-(R)Cha-(R,S)Pic-Nag(Z) (See Example 66) and Br—CH₂—COOBn followed by deprotection procedure (b) gave HOOC—CH₂—(Me)(R)Cha-(R,S)Pic-Nag. The two diastereomers where separated by RPLC (CH₃CN/NH₄OAc, 1:3) followed by freeze-drying from H₂O/TFA. This diastereomer came out last of the two from the column.

¹H-NMR (500 MHz, MeOD): δ 0.9–1.1 (m, 2H), 1.15–1.35 (m, 4H), 1.4–1.55 (m, 2H), 1.6–1.85 (m, 12H), 2.3 (m, 1H), 2.85 (s, 3H), 3.15–3.45 (m, 5H), 3.65 (bs, 2H), 4.0 (m, 1H), 4.65 (m, 1H), 5.08 (dd, 1H).

¹³C-NMR (75 MHz, D₂O): guanidine: δ 157.65; carbonyl carbons: δ 169.86 and 172.48.

Example 71

HOOC-(R,S)CH(Me)-(R)Cha-(R,S)Pic-Nag x 2 TFA

Alkylation as described in Example 4 using H-(R)Cha-Pic-Nag(Z) (See Example 65) and Br-CH(Me)-COOBn followed by deprotection procedure (a) gave the title compound as a mixture of four diastereomers.

Example 72

HOOC-(RorS)CH(Me)-(R)Cha-(RorS)Pic-Nag/c x 2 TFA

Obtained by separating the diastereomers formed in Example 71 using RPLC (CH₃CN/NH₄OAc (0.1M), ¼) followed by evaporation and freeze-drying from H₂O/TFA. This diastereomer came out as the third one of the four from the column.

¹H-NMR (300 MHz, D₂O, 2 rotamers ca: 5:1 ratio): δ 0.88 (m, minor rotamer), 0.98–1.63 (m, 7H), 1.63–2.02 (m, 16H; thereof 1.68 (d,3H), 2.28 (m, 1H), 3.10 (t, minor rotamer), 3.25–3.50 (m, 5H; thereof 3.33 (t,2H) and 3.43 (t, 2H)), 3.82 (bd, 1H), 4.02 (q, 1H), 4.55 (d, minor rotamer), 4.65 (d, minor rotamer), 4.72 (m, 1H), 5.10 (m, 1H).

Example 73

HOOC-(RorS)CH(Me)-(R)Cha-(RorS)Pic-Nag/d x 2 TFA

Obtained by separating the diastereomers formed in Example 71 using RPLC (CH₃CN/NH₄OAc (0.1M), 1:4) followed by evaporation and freeze-drying from H₂O/TFA. This diastereomer came out last of the four diastereomers from the column.

¹H-NMR (500 MHz, D₂O, 2 rotamers ca: 5:1 ratio): δ 0.80 (m, minor rotamer), 0.90 (m, minor rotamer), 1.03 (m, 2H), 1.10–1.33 (m, 3H), 1.42 (m, 2H), 1.51–1.92 (m, 16H; thereof 1.57 (d, 3H)), 2.18 (d, 1H), 2.24 (d, minor rotamer), 2.98 (t, minor rotamer), 3.21 (t, 2H), 3.28–3.40 (m, 3H; thereof 3.44 (t, 2H)), 3.82 (d, 1H), 4.02 (q, 1H), 4.42 (d, minor rotamer), 4.50 (t, minor rotamer), 4.62 (t, 1H), 4.67 (s, minor rotamer), 5.03 (s, 1H).

Example 74

HOOC—CH2—CH2—(R)Cha-Pic-Nag x 2 TFA

Prepared from H-(R)Cha-Pic-Nag(Z) (See Example 65) in the same way as described for HOOC—CH₂—CH₂—(R)Cha-Pro-Agm in Example 15 using 1.2 eq. of benzylacrylate insted of 1.1 eq.

¹H-NMR (500 MHz, D₂O, 2 rotamers ca: 4:1 ratio): δ 0.7–0.9 (m, minor rotamer), 0.9–1.0 (m, 2H), 1.05–1.3 (m, 3H), 1.3–1.45 (m, 2H), 1.5–1.8 (m, 13H), 2.10 (d, 1H), 2.20 (d, minor rotamer), 2.75 (t, 2H), 2.95 (t, minor rotamer), 3.15 (t, 2H), 3.2–3.35 (m, 5H), 3.75 (d, 1H), 4.55 (t, 1H), 4.95 (m, 1H).

¹³C-NMR (75 MHz, D₂O): guanidine: δ 157.57; carbonyl carbons: δ 170.16, 172.82, 174.75.

Example 75

HOOC—CH₂—(R)Cha-(R,S)Mor-Agm x 2 TFA (i) H-(R)Cha-Mor-Agm(Z)

Prepared from Boc-(R)Cha-Mor-OSu (See Prep. of starting materials) in the same way as described for H-(R)Cha-Pro-Agm(Z) in Example 3.

(ii) HOOC —CH₂—(R)Cha-(R,S)Mor-Agra x 2 TFA

Alkylation as in Example 4 using Br—CH₂COOBn followed by deprotection procedure (b) gave the title compound. An epimerization of Mor had occured somewhere during the synthesis and a mixture of about 9:1 of two diastereomers was observed in the final product.

$^1$H-NMR (300 MHz, MeOD): δ 0.92–1.95 (m, 17 H), 3.12–3.39 (m, 4H), 3.44–4.05 (m, 7H), 4.37 (d, 1H), 4.63 (m, 1H), 4.79 (bd, 1H).

$^{13}$C-NMR (75.47 MHz, MeOD): guanidine: δ 158.63; carbonyl carbons: δ 170.87, 170.82, 169.08 others: δ 69.06, 67.01 (C-O-C).

Example 76

HOOC—CH$_2$—(R)Cha-(RorS)Mor-Nag x 2 TFA (i) H-(R)Cha-Mor-Nag(Z)

Prepared from Boc-(R)Cha-Mor-OSu (See Prep. of starting materials) and Boc-Nag(Z) in the same way as described for H-(R)Cha-Pro-Agm(Z) in Example 3.

(ii) HOOC—CH$_2$—(R)Cha-(RorS)Mor-Nag x 2 TFA

Alkylation as described in Example 4 using Br—CH$_2$COOBn followed by deprotection procedure (b) gave the title compound.

$^1$H-NMR (300 MHz, MeOD): δ 0.92–1.13 (m, 2H), 1.15–1.42 (m, 3H), 1.50 (br.s, 1H), 1.62–1.95 (m, 9H), 3.14–3.40 (m, 4H), 3.46–4.13 (m, 7H), 4.41 (d, 1H), 4.63 (m, 1H), 4.80 (br.d, 1H).

$^{13}$C-NMR (75.47 MHz, MeOD): guanidine: δ 158.68; carbonyl carbons: δ 171.19, 170.90, 169.46. others: δ 68.81, 67.00 (C-O-C).

Example 77

H-(R)Cha-Aze-Nag x 2 HOAc (i) Boc-(R)Cha-Aze-Nag(Z)

Prepared from Boc-(R)Cha-Aze-OH in the same way as described for Boc-(R)Cha-Pic-Nag(Z) according to Example 65 (ic).

(ii) H-(R)Cha-Aze-Nag(Z)

Prepared in the same way as described for H-(R)Cha-Pro-Agm(Z) (See Example 3).

(iii) H-(R)Cha-Aze-Nag x 2 HOAc

Prepared by using the deprotection procedure (a) on the product (ii) above.

$^1$H-NMR (300 MHz, D$_2$O): δ 0.85–1.10 (m, 2H), 1.10–2.04 (m, 13H) 1.95 (s, acetate), 2.20–2.37 (m, 1H), 2.60–2.82 (m, 1H), 3.15–3.40 (m, 4H), 3.96–4.15 (m, 2H), 4.18–4.30 (m, 1H), 4.30–4.42 (m, 1H), signals of a minor rotamer appears at: δ 0.70, 3.90 and 5.10.

$^{13}$C-NMR (75 MHz, D$_2$O): guanidine: δ 157.39 and carbonyl carbons: δ 170.22 and 172.38.

Example 78

HOOC—CH$_2$—(R)Cha-Aze-Nag x HOAc (i) BnOOC—CH$_2$—(R)Cha-Aze-Nag (Z)

Prepared from H-(R)Cha-Aze-Nag(Z) (See Example 77) according to the procedure described in Example 4.

(ii) HOOC—CH$_2$—(R)Cha-Aze-Nag x HOAc

Prepared by using the the deprotection (a) on the product (i) above.

$^1$H-NMR (500 MHz, MeOD): δ 0.90–1.10 (m, 2H), 1.15–2.00 (m, 13H) 1.95 (s, acetate), 2.20–2.30 (m, 1H), 2.58–2.70 (m, 1H), 3.17–3.30 (m, 4H), 3.35–3.50 (m, 2H), 3.55–3.68 (m, 1H), 4.10–4.20 (m, 1H), 4.30–4.38 (m, 1H), 4.65–4.77 (m, 1H), signals of minor rotamer appears at: δ 3.75, 3.98, 4.03 and 5.08.

$^{13}$C-NMR (75 MHz, D$_2$O): guanidine: δ 157.40 and carbonyl carbons: δ 169.16, 171.92 and 172.13.

Example 79

H-(R)Cha-Pro(5-(S)Me)-Nag x 2 HCl (i) Boc-(R)Cha-Pro(5-(S)Me)-Nag(Z)

The same procedure as described for the coupling between Boc-(R)Cha-OH and H-Pic-OEt x HCl (See Preparation of Starting Materials) was used to accomplish the coupling between Boc-(R)Cha-Pro(5-(S)Me)-OH and H-Nag(Z) x 2 HCl.

(ii) H-(R)Cha-Pro(5-(S)Me)-Nag(Z)

The same procedure as described for the synthesis of H-(R)-Cgl-Pic-Nag(Z) (See Example 84 (ii) was used.

(iii) H-(R)Cha-Pro(5-(S)Me)-Nag x 2 HCl

Prepared by using the deprotection procedure (d) on the product (ii) above.

$^1$H-NMR (300 MHz, D$_2$O): δ 1.0–2.3 (m, 21H); thereof 1.47 (d, 3H), 2.4–2.55 (m, 1H), 3.3–3.6 (m, 4H), 4.30 (bt, 1H), 4.38 (dd, 1H), 4.47 (bt, 1H).

$^{13}$C-NMR (75 MHz, D$_2$O): guanidine: δ 157.6 carbonyl carbons: δ 174.6, 169.6.

Example 80

HOOC—CH$_2$—(R)Cha-Pro(5-(S)Me)-Nag x HOAc

Alkylation as in Example 4 using H-(R)Cha-Pro(5-(S)Me)-Nag(Z) (See Example 79) and Br—CH$_2$-COOBn followed by deprotection procedure (a) gave the title compound.

$^1$H-NMR (300 MHz, D$_2$O): δ 0.9–1.9 (m, 19H); thereof 1.34 (bd, 3H), 1.93 (s, acetate), 2.0–2.2 (m, 3H), 2.34 (m, 1H), 3.1–3.5 (m, 7H), 3.97 (m, 1H), 4.20 (m, 1H), 4.31 (bt, 1H).

$^{13}$C-NMR (75 MHz, D$_2$O): guanidine: δ 157.4.

Example 81

HOOC—CH$_2$—(R)Cha-(RorS)Pic(4,5-dehydro)-Nag/b x HOAc (i) Boc-(R)Cha-(R,S)Pic(4,5-dehydro)-Nag(Z)

Prepared from Boc-(R)Cha-(R,S)Pic(4,5-dehydro)-OH in the same way as described for Boc-(R)Cha-Pic-Nag(Z) (See Example 65 (ic)).

(ii) H-(R)Cha-(R,S)Pic(4,5-dehydro)-Nag(Z)

Prepared in the same way as described for H-(R)Cha-Pro-Agm(Z) (See Example 3).

(iii) BnOOC—CH$_2$—(R)Cha-(R,S)Pic(4,5-dehydro)-Nag(Z)

Prepared from H-(R)Cha-(R,S)Pic(4,5-dehydro)-Nag(Z) according to the procedure described in Example 4.

(iv) HOOC—CH$_2$—(R)Cha-(RorS)Pic(4,5-dehydro)-Nag/b x HOAc

A mixture of 356 mg (0.539 mmol) of BnOOC—CH$_2$—(R)Cha-(R,S) Pic(4,5-dehydro)-Nag(Z), 10.8 mL trifluoroaceticacid and 3.4 ml tioanisole was stirred at room temperature for 3.5 h. Water was added and the mixture was washed twice with CH$_2$Cl$_2$ evaporation of the solvent gave HOOC—CH$_2$-(R)Cha-(R,S)Pic(4,5-dehydro)-Nag. The title compound was obtained by separating the diastereomers by RPLC (CH$_3$CN/NH$_4$OAc (0.1M), ⅓) and freeze drying (H$_2$O) after evaporation of the solvent. The diastereomer came out last of the two from the column.

¹H-NMR (300 MHz, D₂O) δ 0.85–1.95 (m, 15H), 2.50–2.80 (m, 2H), 3.25 (t, 2H), 3.35 (t, 2H), 3.55 (bs, 2H), 3.85–4.6 (m, 3H), 4.92 (minor rotamer), 5.30 (d, 1H), 5.85–6.1 (m, 2H), ¹³C-NMR (75 MHz, D₂O): guanidine: δ 157.59; carbonyl carbons: δ 171.46, 172.58, 173.03.

Example 82

HOOC—CH₂—(R)Cha-Pic(4-(S)Me)-Nag x 2 HCl (i) Boc-(R)Cha-Pic(4-(S)Me)-Nag(Z)

Prepared from Boc-(R)Cha-Pic(4-(S)Me)-OH in the same way as described for Boc-(R)Cha-Pic-Nag(Z) according to method (ic) in Example 65.

(ii) H-(R)Cha-Pic(4-(S)Me)-Nag(Z)

Prepared in the same way as described for H-(R)Cha-Pro-Agm(Z) (See Example 3).

(iii) BnOOC—CH₂—(R)Cha-Pic(4-(S)Me)-Nag(Z)

Prepared from H-(R)Cha-Pic(4-(S)Me)-Nag(Z) according to the procedure described in Example 4.

(iv) HOOC—CH₂—(R)Cha-Pic(4-(S)Me)-Nag x 2 HCl

Prepared by using the deprotection procedure (d) on the product (iii) above.

¹H-NMR (500 MHz, D₂O): δ 0.95–2.05 (m, 22H; thereof 1.05 (d, 3H)), 2.30–2.38 (bd, 1H), 3.28–3.36 (m, 2H) 3.36–3.50 (m, 3H), 3.85–3.95 (m, 1H), 3.98 (s, 2H), 4.70–4.90 (m, 1H; partly hidden behind the HOD signal), 5.22–5.27 (d, 1H), signal of a minor rotamer appears at δ 0.93, 3.13 and 4.57.

¹³C-NMR (125 MHz, D₂O): guanidine: δ 157.58; carbonyl carbons: δ 170.12, 170.32 and 172.82.

Example 83

HOOC—CH₂—(R)Cha-(R)Pic(4-(R)Me)-Nag x 2 HCl (i) Boc-(R)Cha-(R)Pic(4-(R)Me)-Nag(Z)

Prepared from Boc-(R)Cha-(R)Pic(4-(R)Me)-OSu and Boc-Nag(Z) in the same way as described for Boc-(R)Cha-Pro-Agm(Z) (See Example 3).

(ii) H-(R)Cha-(R)Pic(4-(R)Me)-Nag(Z)

Prepared in the same way as described for H-(R)Cha-Pro-Agm(Z) (See Example 3).

(iii) BnOOC—CH₂—(R)Cha-(R)Pic(4-(R)Me)-Nag(Z)

Prepared from H-(R)Cha-(R)Pic(4-(R)Me)-Nag(Z) according to the procedure described in Example 4.

(iv) HOOC—CH₂—(R)Cha-(R)Pic(4-(R)Me)-Nag x 2 HCl

Prepared by using the deprotection procedure (d) on the product (iii) above.

¹H-NMR (500 MHz, D₂O): δ 1.00–2.05 (m, 22H), 2.18–2.26 (bd, 1H), 3.28–3.36 (m, 2H), 3.36–3.55 (m, 3H), 3.85–4.05 (m, 3H), 4.70–4.90 (m, 1H; partly hidden behind the HOD signal), 5.25–5.30 (d, 1H), signals of minor rotamer apppears at: δ 2.40, 2.90, 4.10, 4.42, 4.55 and 5.23.

¹³C-NMR (125 MHz, D₂O): guanidine: δ 157.56: carbonyl carbons: δ 169.69, 169.84 and 173.20.

Example 84

HOOC—CH₂—(R)Cgl-Pic-Nag x 2 HCl (i) Boc-(R)Cgl-Pic-Nag(Z)

Prepared from Boc-(R)Cgl-Pic-OH in the same way as described for Boc-(R)Cha-Pic-Nag(Z) according to method (ic) in Example 65.

¹H-NMR (300 MHz, CDCl₃): δ 0.9–1.8 (m, 27H), 2.4 (d, 1H), 3.1–3.3 (m, 5H), 3.9 (d, 1H), 4.2 (t, 1H), 5.1 (s, 2H), 5.2 (bd, 2H), 6.7–7.4 (m, 9H).

(ii) H-(R)Cgl-Pic-Nag(Z)

Gaseous hydrogen chloride was bubbled through a solution of Boc-(R)Cgl-Pic-Nag(Z) (1.38 g, 2.22 mmol) in ethyl acetate (25 ml). After 10 minutes the solvent was evaporated and the residue was dissolved in ethyl acetate and 10% Na₂CO₃. The organic phase was separated, washed with brine and dried (MgSO₄). Evaporation of the solvent gave 1.02 g (92%) of the title compound.

¹H-NMR (300 MHz, MeOD): δ 1.0–1.9 (m, 18H), 2.2–2.3 (m, 1H), 3.2–3.3 (m, 5H), 3.6 ( d, 1H), 3.8–3.9 (bd, 1H), 4.2 ( t, 1H), 4.7–4.8 (bs, 5H), 5.1 (s, 2H), 5.2 (s, 1H), 7.2–7.3 (m, 5H).

(iii) BnOOC—CH₂—(R)Cgl-Pic-Nag(Z)

A solution of the triflate ester of benzyl glycolate (291 mg, 0.98 mmol) in CH₂Cl₂ (2 ml) was added at −25° C. to a stirred mixture of H-(R)Cgl-Pic-Nag(Z) (0.52 g, 1.04 mmol) and K₂CO₃ (494 mg, 3.58 mmol) in acetonitrile (5 ml) and CH₂Cl₂ (1 ml). The temperature was allowed ro reach room temperature during a couple of hours and after 5 days the reaction mixture was diluted with water and extracted with EtOAc and toluene. Drying of the organic phase (MgSO₄) and concentration of the solution gave 319 mg (47%) of colorless crystals.

¹H-NMR (500 MHz, CDCl₃): δ 1.0–1.1 (m, 1H), 1.1–1.3 (m, 4H), 1.35–1.6 (m, 5H), 1.6–1.85 (m, 8H), 1.8–2.2 (bs, 1H), 2.23–2.5 (m, 2H), 2.9 ( t, 1H), 3.1–3.5 (m, 6H), 3.6–3.7 (m, 2H), 5.0–5.1 (m, 4H), 5.2 (s, 1H), 6.5–7.4 (m, 13H).

(iv) HOOC—CH2—(R)Cgl-Pic-Nag x 2 HCl

BnOOC—CH₂—(R)Cgl-Pic-Nag(Z) (319 mg, 0.49 mmol) was dissolved by heating in isopropanol (50 ml) and water (5 ml) and hydrogenated for 24 h over 10% Pd/C (228 mg). After filtration and evaporation of the solvent and susequent dissolution in dilute hydrochloric acid followed by freeze drying, the peptide (223 mg, 91%) was isolated as a white powder.

¹H-NMR (500 MHz, D₂O): δ 1.1–2.1 (m, 18H) 2.3 (d, 1H), 3.3 (t, 2H), 3.4 (t, 3H), 3.85–4.05 (m, 3H), 4.6 (d, 1H), 5.15 (s, 1H).

¹³C-NMR (75 MHz, D₂O): guanidine: δ 157.43 carbonyl carbons: δ 169.2, 172.94.

Example 85

H-(R)Hoc-Pro-Nag x 2 TFA (i) Boc-(R)Hoc-Pro-Nag(Z)

Prepared from Boc-(R)Hoc-Pro-OH in the same way as described for Boc-(R)Cha-Pic-Nag(Z) according to Example 65 (ic).

(ii) H-(R)Hoc-Pro-Nag(Z)

Prepared in the same way as described for H-(R)Cha-Pro-Agm(Z) (See Example 3).

(iii)H-(R)Hoc-Pro-Nag x TFA

Prepared by using the deprotection procedure (a) on the product (ii) above.

¹H-NMR (300 MHz, D₂O): δ 0.90–1.05 (m, 2H), 1.16–1.48 (m, 6H), 1.48–1.84 (m, 6H), 1.84–2.24 (m, 6H), 2.40 (m, 1H), 3.25–3.45 (m, 4H), 3,74 (m, 1H), 3.85 (m, 1H), 4.42 (m, 1H), 4.51 (m, 1H).

Example 86

HOOC—CH$_2$—(R)Hoc-Pro-Nag x HOAc (i) BnOOC—CH$_2$—(R)Hoc-Pro-Nag(Z)

Prepared from H-(R)Hoc-Pro-Nag(Z) (See Example 85) according to the procedure described in Example 4.

(ii) HOOC—CH$_2$—(R)Hoc-Pro-Nag x HOAc

Prepared by using the deprotection procedure (a) on the product (i) above.

$^1$H-NMR (300 MHz, D$_2$O): δ 0.76–0.97 (m, 2H), 1.00–1.37 (m, 6H), 1.50–2.12 (m, 12H) 1.89 (s, acetate), 2.27 (m, 1H), 3.10–3.33 (m, 4H), 3.41 (bs, 2H), 3.61 (m, 1H), 3.77 (m, 1H ), 4.12 (m, 1H), 4.37 (m, 1H).

$^{13}$C-NMR (75 MHz, D$_2$O): guanidine: δ 157.4; carbonyl carbons: δ 170.8, 173.9, 174.5.

Example 87

HOOC—CH$_2$—(R)Hoc-Pic-Nag x HOAc (i) Boc-(R)Hoc-Pic-Nag(Z)

Prepared from Boc-(R)Hoc-Pic-OH in the same way as described for Boc-(R)Cha-Pic-Nag(Z) according to method (ic) in Example 65.

(ii) H-(R)Hoc-Pic-Nag(Z)

Prepared in the same way as described for H-(R)Cha-Pro-Agm(Z) (See Example 3).

(iii) BnOOC—CH$_2$—(R)Hoc-Pic-Nag(Z)

Prepared according to the procedure described in Example 4.

(iv) HOOC—CH$_2$—(R)Hoc-Pic-Nag x HOAc

Prepared by using the deprotection procedure (a) on the product (iii) above.

$^1$H-NMR (300 MHz, D$_2$O): δ 0.75–0.95 (m, 2H), 1.00–1.30 (m, 6H), 1.30–1.50 (m, 2H), 1.50–1.82 (m, 12H), 1.82–1.95 (bs, acetate), 2.23 (bd, 1H), 3.08–3.32 (m, 6H), 3.52 (bs, 2H), 3.77 (bd, 1H), 4.50 (bs, 1H), 5.00 (bs, 1H).

Example 88

HOOC—CH$_2$—(R)DDh-Pic-Nag x 2 HCl (i) Boc-(R)Dph-Pic-Nag(Z)

Prepared from Boc-(R)Dph-Pic-OH in the same way as described for Boc-(R)Cha-Pic-Nag(Z) (See Example 65 (ic)).

(ii) H-(R)Dph-Pic-Nag(Z)

Prepared in the same way as described for H-(R)Cgl-Pic-Nag(Z) (See Example 84 (ii)).

(iii) BnOOC—CH$_2$—(R)Dph-Pic-Nag(Z)

Prepared from H-(R)Dph-Pic-Nag(Z) according to the procedure described in Example 4.

(iv) HOOC—CH$_2$—(R)Dph-Pic-Nag x 2 HCl

Prepared by using the deprotection procedure (d) on the product (iii) above.

$^1$H-NMR (500 MHz, D$_2$O): δ 0.46 (m, 1H), 1.2–1.35 (m, 2H), 1.45 (m, 1H), 1.53 (m, 1H), 1.89 (pentet, 2H), 2.03 (bd, 1H), 3.24 (bt, 1H), 3.29 (t, 2H), 3.38 (t, 2H), 3.72 (d, 1H), 3.78 (d, 1H), 3.79 (m, 1H), 4.68 (d, 1H), 4.89 (m, 1H), 5.73 (d, 1H), 7.4–7.6 (m, 6H), 7.65 (t, 2H), 7.81 (d, 2H).

Example 89

HOOC—CH$_2$—(R)Dch-Pic-Nag x HOAc (i) Boc-(R)Dch-Pic-Nag(Z)

Prepared from Boc-(R)Dch-Pic-OH in the same way as described for Boc-(R)Cha-Pic-Nag(Z) (in Example 65 (ic).

(ii) H-(R)Dch-Pic-Nag(Z)

Prepared in the same way as described for H-(R)Cgl-Pic-Nag(Z) (in Example 84 (ii).

(iii) BnOOC—CH$_2$—(R)Dch-Pic-Nag(Z)

Prepared from H-(R)Dch-Pic-Nag(Z) according to the procedure described in Example 4.

(iv) HOOC—CH$_2$—(R)Dch-Pic-Nag x HOAc

Prepared by using the deprotection procedure (a) on the product (iii) above.

$^1$H-NMR (500 MHz, D$_2$O): δ 1.2–2.0 (m, 30H), 2.09 (s, acetate), 2.30 (bd, 1H), 3.32 (t, 2H), 3.4–3.5 (m, 3H), 3.65 (d, 1H), 3.70 (d, 1H), 3.86 (bd, 1H), 4.86 (m, 1H), 5.09 (m, 1H).

$^{13}$C-NMR (125 MHz, D$_2$O): guanidine: δ 159.4, carbonyl carbons: δ 172.5, 173.3, 174.9.

Example P1

Solution for parenteral administration

A solution is prepared from the following ingredients:

| | |
|---|---|
| HOOC—CH2—(R)Cha—Pic—Nag x 2HBr | 5 g |
| Sodium chloride for injection | 9 g |
| Acetic acid | 3 g |
| Water for inj. up to 1000 ml | |

The active constituent, the sodium chloride and the acetic acid are dissolved in the water. The pH is adjusted with 2M NaOH to pH 3–7. The solution is filtered through a sterile 0.2 μm filter and is aseptically filled into sterile ampoules.

Example P2

Tablets for oral administration 1000 tablets are prepared from the following ingredients:

| | |
|---|---|
| Thrombin inhibitor | 100 g |
| Lactose | 200 g |
| Polyvinyl pyrrolidone | 30 g |
| Microcrystalline cellulose | 30 g |
| Magnesium stearate | 6 g |

The active constituent and lactose are mixed with an aqueous solution of polyvinyl pyrrolidone. The mixture is dried and milled to form granules. The microcrystalline cellulose and then the magnesium stearate are then admixed. The mixture is then compressed in a tablet machine giving 1000 tablets, each containing 100 mg of active constituent.

Biology

Determination of thrombin clotting time and IC$_{50}$TT:

Human thrombin (T 6769, Sigma Chem Co) in buffer solution, pH 7.4, 100 μl, and inhibitor solution, 100 μl, were incubated for one min. Pooled normal citrated human plasma, 100 μl, was then added and the clotting time measured in an automatic device (KC 10, Amelung).

The clotting time in seconds was plotted against the inhibitor concentration, and the IC$_{50}$TT was determined by interpolation.

IC$_{50}$TT is the concentration of inhibitor that doubles the thrombin clotting time for human plasma. pIC$_{50}$TT is the -log 10 of IC$_{50}$TT in mol/l. The preferred compounds of the invention have an pIC$_{50}$TT in the range 6.6–8.2.

Determination of Activated Partial Thromboplastin Time (APTT)

APTT was determined in pooled normal human citrated plasma with the reagent PTT Automated 5 manufactured by Stago. The inhibitors were added to the plasma (10 μl inhibitor solution to 90 μl plasma) and APTT was determined in the mixture by use of the coagulation analyser KC10 (Amelung) according to the instructions of the reagent producer. The clotting time in seconds was plotted against the inhibitor concentration in plasma and the $IC_{50}APTT$ was determined by interpolation.

$IC_{50}APTT$ is defined as the concentration of inhibitor in plasma that doubled the Activated Partial Thromboplastin Time. $pIC_{50}APTT$ is the -log 10 of $IC_{50}APTT$ in mol/l. Those of the preferred compounds of the invention that were tested showed a $pIC_{50}APTT$ of 5.1–6.4.

| ABBREVIATIONS | |
|---|---|
| Agm = | Agmatine |
| Agm(Z) = | ω-N-benzyloxycarbonyl agmatine |
| $AA_1$ = | Amino acid 1 |
| $AA_2$ = | Amino acid 2 |
| Aze = | (S)-Azetidine-2-carboxylic acid |
| Bla = | α-substituted butyrolactone |
| Boc = | tertiary butoxy carbonyl |
| Brine = | saturated water/NaCl solution |
| Bu = | butyl |
| Bn = | benzyl |
| Cgl = | (S)-Cyclohexyl glycine |
| Ch = | cyclohexyl |
| Cha = | (S)-β-cyclohexyl alanine |
| CME-CDI = | 1-Cyclohexyl-3-(2-morpholinoethyl) carbodiimide metho-p-toluenesulfonate |
| DCC = | dicyclohexyl carbodiimide |
| Dch = | (S)-Dicyclohexyl alanine |
| DMAP = | N,N-dimethyl amino pyridine |
| DMF = | dimethylformamide |
| DMSO = | dimethyl sulfoxide |
| Dph = | (S)-Diphenyl alanine |
| EDC = | 1-(3-Dimetylaminopropyl)-3-ethylcarbodiimide hydrochloride |
| Et = | ethyl |
| EtOAc = | ethyl acetate |
| HOAc = | acetic acid |
| HOBT = | N-hydroxybenzotriazole |
| Hoc = | (S)-Homocyclohexyl alanine |
| Hop = | (S)-Homophenyl alanine |
| HOSu = | N-hydroxysuccinimide |
| Mag = | miniagmatine |
| Me = | methyl |
| Mor = | (S)-morpholine-2-carboxylic acid |
| Mpa = | mega pascal |
| Nag = | noragmatine |
| Nag(Z) = | δ-N-benzyloxycarbonyl-noragmatine |
| NMM = | N-methyl morpholine |
| Pgl = | (S)-phenylglycine |
| Ph = | phenyl |
| Phe = | (S)-phenylalanine |
| Pic = | (S)-pipecolinic acid |
| Pr = | propyl |
| Pro = | (S)-proline |
| RPLC = | reverse phase high-performance liquid chromatography |
| Tf = | trifluoromethylsulfonyl |
| TFA = | trifluoracetic acid |
| THF = | tetrahydrofuran |
| p-TsOH = | para-toluenesulfonic acid |
| Val = | (S)-valine |
| Z = | benzyloxycarbonyl |

Prefixes n, s, i and t have their usual meanings: normal, iso, sec and tertiary.

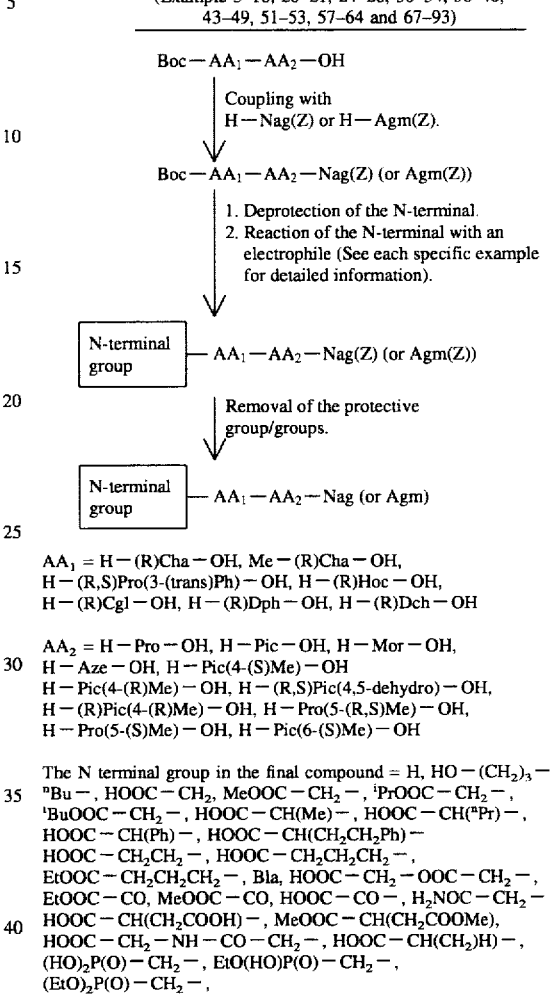

Scheme I
(Example 3–18, 20–21, 24–28, 30–34, 36–40, 43–49, 51–53, 57–64 and 67–93)

$AA_1$ = H—(R)Cha—OH, Me—(R)Cha—OH,
H—(R,S)Pro(3-(trans)Ph)—OH, H—(R)Hoc—OH,
H—(R)Cgl—OH, H—(R)Dph—OH, H—(R)Dch—OH $AA_2$ = H—Pro—OH, H—Pic—OH, H—Mor—OH,
H—Aze—OH, H—Pic(4-(S)Me)—OH
H—Pic(4-(R)Me)—OH, H—(R,S)Pic(4,5-dehydro)—OH,
H—(R)Pic(4-(R)Me)—OH, H—Pro(5-(R,S)Me)—OH,
H—Pro(5-(S)Me)—OH, H—Pic(6-(S)Me)—OH The N terminal group in the final compound = H, HO—$(CH_2)_3$—,
$^nBu$—, HOOC—$CH_2$—, MeOOC—$CH_2$—, $^iPrOOC$—$CH_2$—,
$^tBuOOC$—$CH_2$—, HOOC—CH(Me)—, HOOC—CH($^nPr$)—,
HOOC—CH(Ph)—, HOOC—CH($CH_2CH_2Ph$)—
HOOC—$CH_2CH_2$—, HOOC—$CH_2CH_2CH_2$—,
EtOOC—$CH_2CH_2CH_2$—, Bla, HOOC—$CH_2$—OOC—$CH_2$—,
EtOOC—CO, MeOOC—CO, HOOC—CO—, $H_2NOC$—$CH_2$—
HOOC—CH($CH_2COOH$)—, MeOOC—CH($CH_2COOMe$),
HOOC—$CH_2$—NH—CO—$CH_2$—, HOOC—CH($CH_2$)H)—,
$(HO)_2P(O)$—$CH_2$—, EtO(HO)P(O)—$CH_2$—,
$(EtO)_2P(O)$—$CH_2$—, Scheme II
(Example 55, 56, 65 and 66)
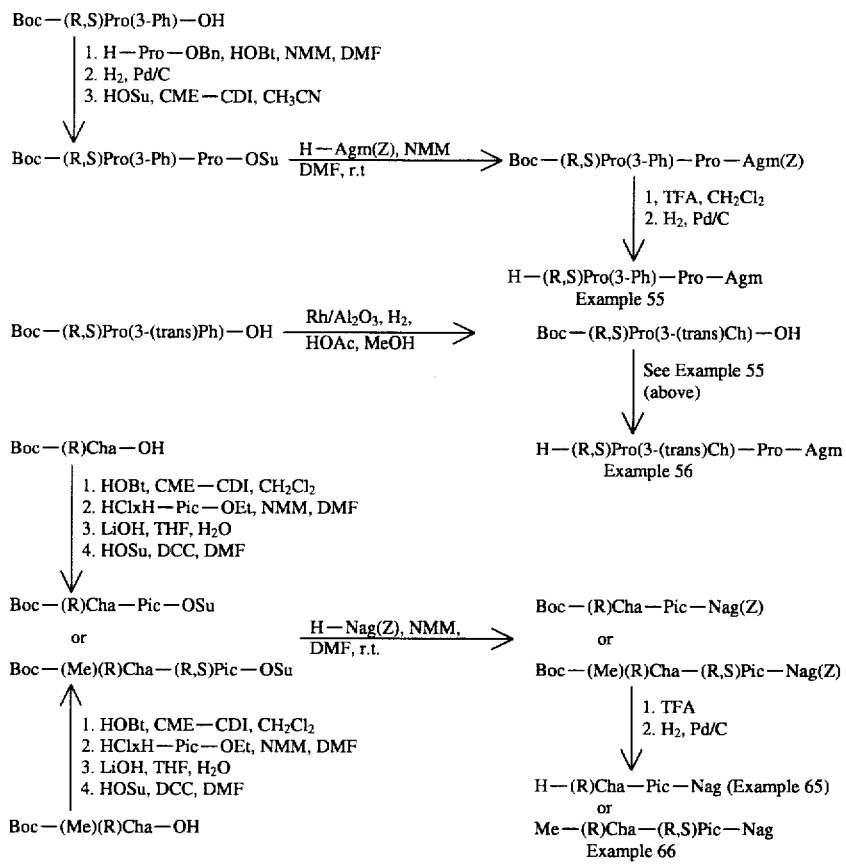
Scheme III
(Example 1 and 2)
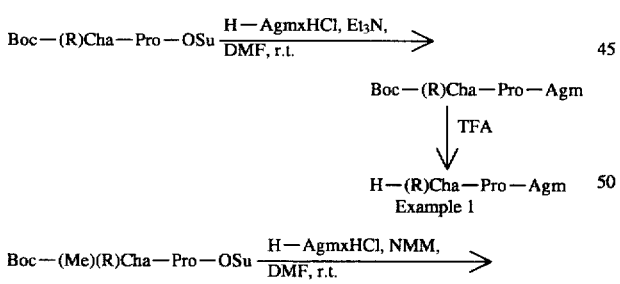
Scheme IV
(Example 19)
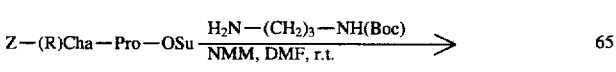
-continued
Scheme IV
(Example 19)
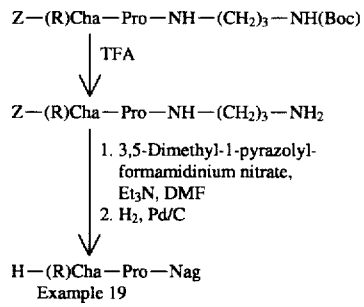
Scheme V
(Example 54)
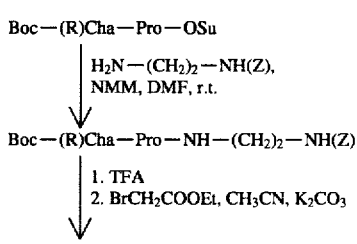

Scheme V
(Example 54)
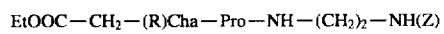
1. H₂, Pd/C
2. 3,5-Dimethyl-1-pyrazolyl-
   formamidinium nitrate, Et₃N, DMF
3. NaOH/EtOH
HOOC—CH₂—(R)Cha—Pro—Mag
Example 54
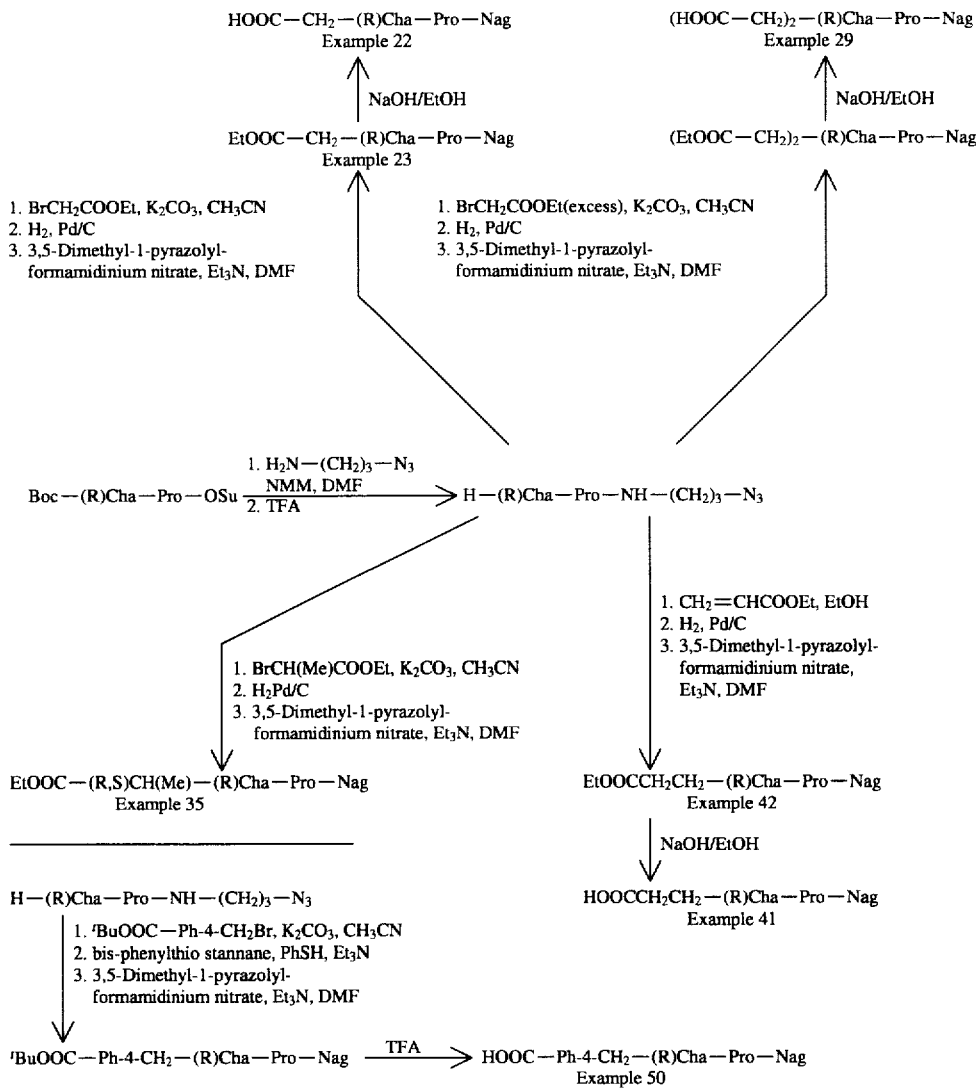

I claim:
1. A compound of the formula

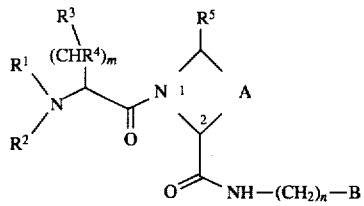

Formula I or a stereoisomer thereof wherein:

A represents an ethylene group and the resulting 5-membered ring is optionally unsaturated, or A represents —$CH_2$—O—, and the resulting 5-membered ring has the oxygen atom in position 4, or A represents a n-propylene group and the resulting 6-membered ring is optionally unsaturated in positions 4 and 5, or optionally bears in position 4 an alkyl group with 1 to 4 carbon atoms, or A represents —$CH_2$—O—$CH_2$—;

$R^1$ represents H, an alkyl group having 1 to 4 carbon atoms, a hydroxyalkyl group having 2–3 carbon atoms or $R^{11}$OOC-alkyl-, where the alkyl group has 1 to 4 carbon atoms and $R^{11}$ is H or an alkyl group having 1 to 4 carbon atoms or an alkylene group having 2–3 carbon atoms intramolecularly bonded alpha to the carbonyl group in $R^1$, or $R^1$ represents $R^{12}$OOC-1,4-phenyl—$CH_2$—, where $R^{12}$ is H or an alkyl group having 1 to 4 carbon atoms, or $R^1$ represents $R^{13}$-NH-CO-alkyl-, where the alkyl group has 1 to 4 carbon atoms and where $R^{13}$ is H or —$CH_2$COOR$^{12}$, where $R^{12}$ is as defined above, or $R^1$ represents $R^{12}$OOC—$CH_2$—OOC-alkyl-, where the alkyl group has 1 to 4 carbon atoms and where $R^{12}$ is as defined above, or $R^1$ represents $R^{12}$OCOCO- where $R^{12}$ is as defined above, or $R^1$ represents $R^{12}$OCOCO- where $R^{12}$ is as defined above, or $R^1$ represents $CH_2PO(OR^{14})_2$, where $R^{14}$ is, individually at each occurrence, H, methyl or ethyl;

$R^2$ represents H or an alkyl group having 1 to 4 carbon atoms or $R^{21}$OOC-alkyl-, where the alkyl group has 1 to 4 carbon atoms and is optionally substituted in the position which is alpha to the carbonyl group, and the alpha substituent is a group $R^{22}$—$(CH_2)_p$—, wherein p=0–2 and $R^{22}$ is methyl, phenyl, OH, or COOR$^{21}$, and $R^{21}$ is H or an alkyl group having 1 to 4 carbon atoms;

m is 0, 1 or 2, $R^3$ represents a cyclohexyl group and $R^4$ represents H, or m is 1, $R^3$ represents a cyclohexyl or phenyl group, $R^1$ is absent and $R^4$ is an ethylene group bonded to the nitrogen atom bearing $R^2$, or m is 1 and $R^3$ and $R^4$ each represents a cyclohexyl or phenyl group;

$R^5$ represents H or an alkyl group having 1 to 4 carbon atoms; n is an integer 2, 3 or 4;

B represents -N($R^6$)-C(NH)-$NH_2$, wherein R is H;
and wherein the amino acid bearing $R^3$ on its side chain is designated P3, and the amino acid containing A is designated P2;

or a physiologically acceptable salt thereof.

2. A compound according to claim 1 wherein $R^1$ represents $R^{11}$OOC-alkyl-, where the alkyl group has 1 to 4 carbon atoms and $R^{11}$ is H.

3. A compound according to claim 2 wherein A is ethylene and $R^5$ is H or an alkyl group having 1 to 4 carbon atoms.

4. A compound according to claim 2 wherein A is n-propylene and the resulting 6-membered ring optionally bears in position 4 an alkyl group with 1 to 4 carbon atoms, and $R^5$ is H or an alkyl group having 1 to 4 carbon atoms.

5. A compound according to claim 1 wherein $R^3$ is cyclohexyl, m is 1 or 2 and $R^4$ is H.

6. A compound according to any one of the preceding claims wherein n is 3.

7. A compound according to any one of claims 1–5 in which the α-carbon of the amino acid in the P2 position is of the S-configuration.

8. A compound according to claim 7 in which the α-carbon of the amino acid in the P3 position is of the R-configuration.

9. A compound or a stereoismer thereof selected from
H-(R)Cha-Pro-Agm
Me-(R)Cha-Pro-Agm
HO—(CH₂)₃—(R)Cha-Pro-Agm
ⁱPrOOC—CH₂—(R)Cha-Pro-Agm
HOOC-(R,S)CH(Me)-(R)Cha-Pro-Agm
HOOC-(RorS)CH(Me)-(R)Cha-Pro-Agm/a
HOOC-(RorS)CH(nPr)-(R)Cha-Pro-Agm/a
HOOC-(RorS)CH(nPr)-(R)Cha-Pro-Agm/b
HOOC-(RorS)CH(Ph)-(R)Cha-Pro-Agm/b
HOOC-(R,S)CH(CH₂CH₂Ph)-(R)Cha-Pro-Agm
HOOC-(RorS)CH(CH₂CH₂Ph)-(R)Cha-Pro-Agm/a
HOOC—CH₂—CH₂—(R)Cha-Pro-Agm
EtOOC-CO-(R)Cha-Pro-Agm
(R,S)Bla-(R)Cha-Pro-Agm
HOOC-(RorS)CH(CH₂CH₂Ph)-(R)Cha-Pro-Agm/b
H-(R)Cha-Pro-Nag
ⁿBu-(R)Cha-Pro-Nag
HO—(CH₂)₃—(R)Cha-Pro-Nag
EtOOC—CH₂—(R)Cha-Pro-Nag
ⁱPrOOC—CH₂—(R)Cha-Pro-Nag
ⁱBuOOC—CH₂—(R)Cha-Pro-Nag
HOOC—CH₂—OOC—CH₂—(R)Cha-Pro-Nag
H₂N-CO—CH₂—(R)Cha-Pro-Nag
HOOC—CH₂—NH—CO—CH₂—(R)Cha-Pro-Nag
(HOOC—CH₂)₂—(R)Cha-Pro-Nag
HOOC—CH₂—(nBu)(R)Cha-Pro-Nag
HOOC-(R,S)CH(Me)-(R)Cha-Pro-Nag
HOOC-(RorS)CH(Me)-(R)Cha-Pro-Nag/a
EtOOC-(R,S)CH(Me)-(R)Cha-Pro-Nag
HOOC-(RorS)CH(ⁿPr)-(R)Cha-Pro-Nag/a
HOOC-(R)CH(CH₂—OH)-(R)Cha-Pro-Nag
HOOC-(R,S)CH(Ph)-(R)Cha-Pro-Nag
HOOC-(S)CH(CH₂CH₂Ph)-(R)Cha-Pro-Nag
HOOC-(R)CH(CH₂CH₂Ph)-(R)Cha-Pro-Nag
HOOC—CH₂—CH₂—(R)Cha-Pro-Nag
EtOOC—CH₂—CH₂—(R)Cha-Pro-Nag
HOOC—(CH₂)₃—(R)Cha-Pro-Nag
EtOOC—(CH₂)₃—(R)Cha-Pro-Nag
HOOC-CO-(R)Cha-Pro-Nag
MeOOC-CO-(R)Cha-Pro-Nag
(R,S)Bla-(R)Cha-Pro-Nag
HOOC (R,S)CH(CH₂COOH)-(R)Cha-Pro-Nag
MeOOC-(R,S)CH(CH₂COOMe)-(R)Cha-Pro-Nag
HOOC-Ph-4—CH₂—(R)Cha-Pro-Nag
(HO)₂P(O)—CH₂—(R)Cha-Pro-Nag
EtO(HO)P(O)—CH₂—(R)Cha-Pro-Nag
(EtO)₂P(O)—CH₂—(R)Cha-Pro-Nag
HOOC—CH₂—(R)Cha-Pro-Mag
H-(R,S)Pro(3-Ph)-Pro-Agm
H-(R,S)Pro(3-(trans)Ch)-Pro-Agm
HOOC—CH₂—(R,S)Pro(3-(trans)Ph)-Pro-Agm
HOOC—CH₂—(R,S)Pro(3-(trans)Ph)-Pro-Nag
HOOC—CH₂—(Me)(R)Cha-(R,S)Pic-Agm
HOOC-(R,S)CH(Me)-(R)Cha-Pic-Agm
HOOC-(RorS)CH(Me)-(R)Cha-Pic-Agm/a
HOOC—CH₂—CH₂—(R)Cha-Pic-Agm
H-(R)Cha-Pic-Nag
Me-(R)Cha-(R,S)Pic-Nag
MeOOC—CH₂—(R)Cha-Pic-Nag
ⁱPrOOC—CH₂—(R)Cha-Pic-Nag
HOOC—CH₂—(Me)(R)Cha-(RorS)Pic-Nag/b
HOOC-(R,S)CH(Me)-(R)Cha-(R,S)Pic-Nag
HOOC-(RorS)CH(Me)-(R)Cha-(RorS)Pic-Nag/c
HOOC—CH₂—CH₂—(R)Cha-Pic-Nag
HOOC—CH₂—(R)Cha—(R,S)Mor-Agm
HOOC—CH₂—(R)Cha-(RorS)Mor-Nag
H-(R)Cha-Aze-Nag
HOOC—CH₂—(R)Cha-Aze-Nag
H-(R)Cha-Pro(5-(S)Me)-Nag
HOOC—CH₂—(R)Cha-(RorS)Pic(4,5-dehydro)-Nag/b
HOOC—CH₂—(R)Cha-(R)Pic(4-(R)Me)-Nag
HOOC—CH₂—(R) Cgl-Pic-Nag
H-(R)Hoc-Pro-Nag
HOOC—CH₂—(R)Hoc-Pro-Nag
HOOC—CH₂—(R)Hoc-Pic-Nag
HOOC—CH₂—(R)Dph-Pic-Nag
HOOC—CH₂—(R)Dch-Pic-Nag
HOOC—CH₂—(R)Cha-Pic(4-(R)Me)-Nag
H-(R)Cha-Pic(4-(R)Me)-Nag
or a physiologically acceptable salt thereof.

10. A compound or a stereoismer thereof selected from
HOOC—CH₂—(R)Cha-Pro-Agm
HOOC—CH₂—(Me)(R)Cha-Pro-Agm
HOOC-(RorS)CH(Me)-(R)Cha-Pro-Agm/b
HOOC—CH₂—(R)Cha-Pro-Nag
HOOC—CH₂—(R)Cha-Pic-Agm
HOOC-(RorS)CH(Me)-(R)Cha-Pic-Agm/b
HOOC-(RorS)CH(Me)-(R)Cha-(RorS)Pic-Nag/d
HOOC—CH₂—(R)Cha-Pro(5-(S)Me)-Nag
HOOC—CH₂—(R)Cha-Pic(4-(S)Me)-Nag
either as such or in the form of a physiologically acceptable salt and including stereoisomers.

11. The compound HOOC—CH₂—(Me)(R)Cha-Pro-Nag, a stereoisomer thereof or a physiologically acceptable salt thereof.

12. The compound HOOC-(RorS)CH(Me)-(R)Cha-Pro-Nag/b, a stereoisomer thereof or a physiologically acceptable salt thereof.

13. The compound HOOC—CH₂—(R)Cha-Pic-Nag, a stereoisomer thereof or a physiologically acceptable salt thereof.

14. A compound according to any one of claims 2–4 wherein $R^3$ is cyclohexyl, m is 1 or 2 and $R^4$ is H.

15. A compound according to claim 14 wherein n is 3.

16. A compound according to claim 14, in which the α-carbon of the amino acid in the P2 position is of the S-configuration.

17. A compound according to claim 15 in which the α-carbon of the amino acid in the P2 position is of the S-configuration.

18. A compound according to claim 14 in which the α-carbon of the amino acid in the P3 position is of the R-configuration.

19. A compound according to claim 15 in which the α-carbon of the amino acid in the P3 position is of the R-configuration.

20. A compound according to claim 16 in which the α-carbon of the amino acid in the P3 position is of the R-configuration.

21. A compound according to claim 17 in which the α-carbon of the amino acid in the P3 position is of the R-configuration.

22. A compound according to claim 6 in which the α-carbon of the amino acid in the P2 position is of the S-configuration.

23. A compound according to claim 22 in which the α-carbon of the amino acid in the P3 position is of the R-configuration.

24. A pharmaceutical composition for use as an anticoagulant or antithrombotic agent, comprising an effective amount of a compound of any one of claims 1 and 11–13 in combination with one or more pharmaceutical carriers.

25. A method for inhibiting thrombin in a mammal in need of such inhibition, comprising administering to the mammal an effective amount of a compound of any one of claims 1 and 11–13.

26. A method of treatment or prophylaxis of thrombosis and hypercoaguability in blood and tissues in a mammal in need of such treatment or prophylaxis, comprising administering to the mammal an effective amount of a compound of any one of claims 1 and 11–13.

27. The method of claim 25 wherein the compound is administered perorally and the effective amount of the compound is in the range from 0.001 to 100 mg/kg body weight.

28. The method of claim 26 wherein the compound is administered perorally and the effective amount of the compound is in the range from 0.001 to 100 mg/kg body weight.

29. The method of claim 25 wherein the compound is administered parenterally and the effective amount of the compound is in the range from 0.001 to 50 mg/kg body weight.

30. The method of claim 26 wherein the compound is administered parenterally and the effective amount of the compound is in the range from 0.001 to 50 mg/kg body weight.

* * * * *

UNITED STATES PATENT AND TRADEMARK OFFICE
CERTIFICATE OF CORRECTION

PATENT NO. : 5,614,499
DATED : March 25, 1997
INVENTOR(S) : Bylund et al

It is certified that error appears in the above-identified patent and that said letters patent is hereby corrected as shown below:

Column 57, line 38, insert after "wherein:"

--A represents a methylene group, or --

Signed and Sealed this

Twenty-second Day of July, 1997

Attest:

BRUCE LEHMAN

Attesting Officer

Commissioner of Patents and Trademarks